United States Patent [19]

Ikeda et al.

[11] 4,159,328
[45] Jun. 26, 1979

[54] TETRAHYDRO-1,3,5-THIADIAZIN-4-ONE DERIVATIVE

[75] Inventors: Kenichi Ikeda, Toyonaka; Hideo Kanno, Nishinomiya; Michihiro Yasui, Osaka; Tatsuo Harada, Kawachinagano, all of Japan

[73] Assignee: Nihon Nohyaku Co., Ltd., Tokyo, Japan

[21] Appl. No.: 911,755

[22] Filed: Jun. 2, 1978

[30] Foreign Application Priority Data

Jun. 9, 1977 [JP] Japan .................................. 52-68138
Jun. 29, 1977 [JP] Japan .................................. 52-77594
Feb. 28, 1978 [JP] Japan .................................. 53-22550

[51] Int. Cl.$^2$ ........................ C07D 285/34; A01N 9/12
[52] U.S. Cl. ............................................ 424/246; 544/8
[58] Field of Search .................................. 544/8; 424/246

[56] References Cited

U.S. PATENT DOCUMENTS 3,741,964  6/1973  Chupp ............................. 260/243 R

FOREIGN PATENT DOCUMENTS 1912225 11/1970 Fed. Rep. of Germany.
50-142731 11/1975 Japan.

OTHER PUBLICATIONS

Chupp, J. of Heterocyclic Chemistry, vol. 8, pp. 677-679 (1971).
Tsuge et al., Bull. Chemical Soc., Japan, vol. 45, pp. 2877-2882 (1972).

Primary Examiner—John M. Ford
Attorney, Agent, or Firm—Cushman, Darby & Cushman

[57] ABSTRACT

A tetrahydro-1,3,5-thiadiazin-4-one represented by the general formula,

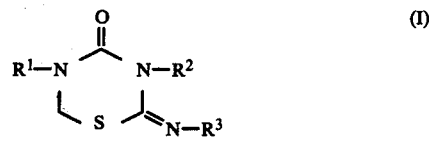

wherein $R^1$, $R^2$ and $R^3$, which may be the same or different, represent each an alkyl group, allyl group, cycloalkyl group, alkoxyalkyl group, benzyl group, phenyl group or substituted phenyl group having as substituents alkyl groups, nitro group, halogen atoms, alkoxy groups, or trifluoromethyl group and $R^2$ and $R^3$ may also represent hydrogen atoms, is a new compound and useful for controlling insects and mites.

24 Claims, No Drawings

TETRAHYDRO-1,3,5-THIADIAZIN-4-ONE DERIVATIVE

This invention relates to tetrahydro-1,3,5-thiadiazin-4-ones represented by the genral formula:

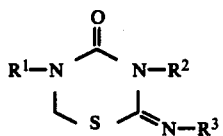

wherein $R^1$, $R^2$ and $R^3$, which may be the same or different, represent each an alkyl group of $C_1$ to $C_8$, allyl group, cycloalkyl group of $C_3$ to $C_6$, alkoxyalkyl group having a total of 3 to 6 carbon atoms, benzyl group, phenyl group or substituted phenyl group having as substituents one or two alkyl groups of $C_1$ to $C_4$, nitro group, halogen atoms, alkoxy groups of $C_1$ to $C_4$, or trifluoromethyl groups and $R^2$ and $R^3$ may represent hydrogen atoms; or acid addition salts thereof. Further, this invention relates also to a process for producing the compounds represented by the above general formula or acid addition salts thereof. Furthermore, this invention relates also to insecticides and miticides containing as active ingredients the compounds represented by the above general formula or the acid addition salts thereof.

The compounds represented by the general formula (I) and the acid addition salts thereof are novel compounds.

The compounds represented by the general formula (I) may be readily synthesized by reacting carbamoyl chlorides represented by the general formula,

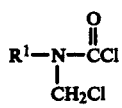

wherein $R^1$ is the same as defined above, with thioureas represented by the general formula,

wherein $R^2$ and $R^3$ are the same as defined above, in the presence of a base. This reaction may be represented by the following equation and the compounds represented by the general formula (I) can be obtained in free state:

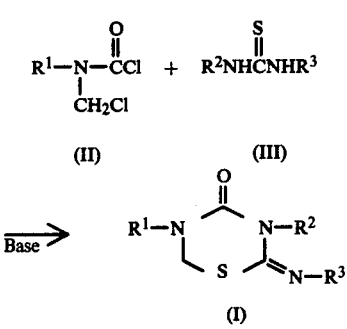

wherein $R^1$, $R^2$ and $R^3$ are as defined above.

On the other hand, a carbamoyl chloride represented by the general formula (II) and a thiourea represented by the general formula (III) can react without the addition of a base. In this case, the compound represented by the general formula (I) is obtained in the form of hydrochloride. The reaction is advantageously carried out under application of heat. Therefore, if it is desirable to obtain the compound represented by the general formula (I) in the form of hydrochloride, it is convenient to carry out the reaction in this way. When the compound represented by the general formula (I) in free state is desired, it is obtained by dissolving the hydrochloride in water and adjusting pH of the solution to neutral or slightly alkaline. The reaction may be represented by the following equation:

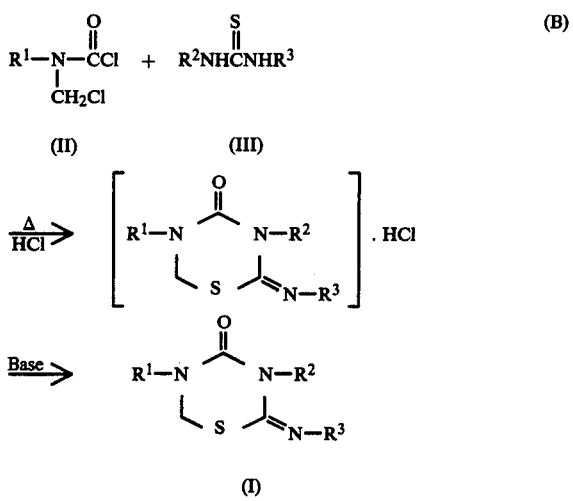

wherein $R^1$, $R^2$ and $R^3$ are as defined above.

Thus, the compound represented by the general formula (I) can be synthesized by either of the procedures (A) and (B). It is also possible to convert the compound represented by the general formula (I) into its salt by treating the compound with an acid of the desired type. All of these procedures are included within the scope of this invention.

The carbamoyl chloride used as one of the reactants in this invention can be synthesized, for example, by the following or similar procedures:

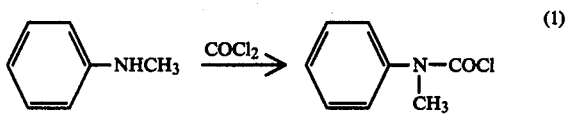

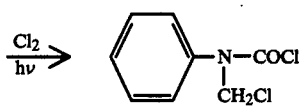

J. Org. Chem., 39, 2897 (1974)

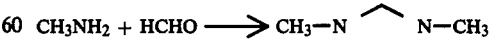

Chem. Abst., 59, 9816f

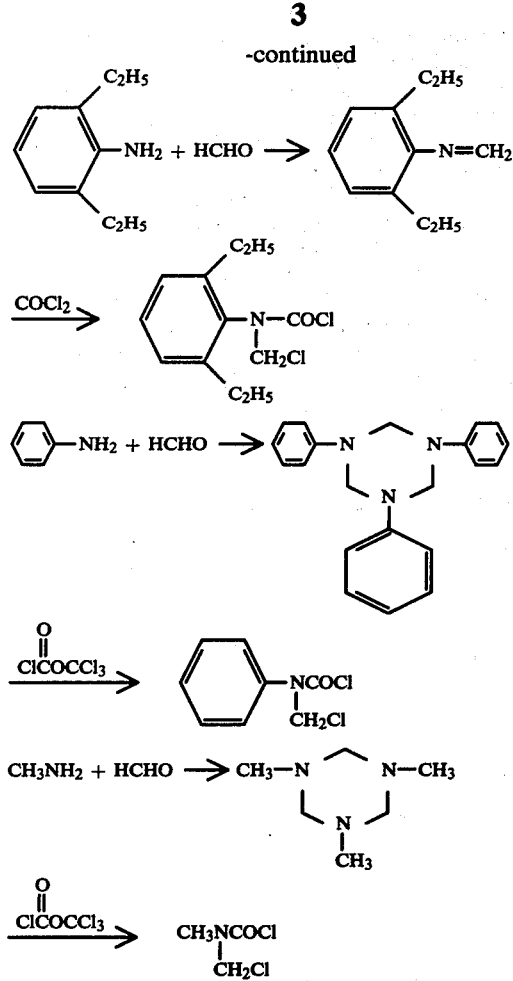

The above procedures (4) and (5) are improvement worked out by the present inventors on the procedure (2).

The procedure (1) cannot be applied to the chlorination of aniline derivatives having on their benzene nuclei substituents sensitive to chlorination. In such a case, it is necessary to follow the route of addition reaction in which a dehydration-condensation product (for example, azomethine or hexahydro-s-triazine) of an aniline derivative and formaldehyde is reacted with phosgene or trichloromethyl chloroformate, as shown in the above procedures (2) to (5). The resulting carbamoyl chloride is not necessarily isolated but the reaction mixture can be used as such in the subsequent reaction with thiourea.

The studies conducted by the present inventors revealed several interesting features of the ringforming reaction in this invention. When the substituents in the thiourea molecule are different from each other, there is a certain tendency with respect to the position occupied by the substituents $R^2$ and $R^3$ in the ultimate compound of the formula (I). When both $R^2$ and $R^3$ of the thiourea are alkyl groups, the substituent which occupies the position $R^3$ in the compound (I) is generally an alkyl group having a longer carbon chain or a bulky alkyl group having a more branched carbon chain attached to the nitrogen atom, the bulkiness having preference to the chain length of the substituent. Accordingly, if a 1,3-dialkyl-thiourea having straight chain alkyl groups is used, the alkyl group with larger number of carbon atoms occupies generally the position $R^3$ in the compound of the formula (I). If a thiourea with substituents of approximately the same bulkiness is used, there is sometimes formed a mixture of the compounds having the fomulas:

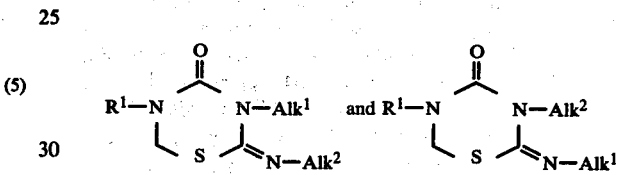

wherein $Alk^1$ and $Alk^2$ represent alkyl groups having approximately the same degree of branching. In this respect, a phenylalkyl group exhibits similar tendency to the alkyl group.

In another case where the ring-forming reaction is carried out using a 1-alkyl-3-arylthiourea, the aryl group is introduced in the position $R^2$ of the compound (I). However, even when such a thiourea is used, if the alkyl group is methyl, there is obtained sometimes a mixture of the compound (I) with the methyl group at the position $R^2$ and that with the methyl group at the position $R^3$.

Such a mixture can be separated, in some cases, into both compounds utilizing the difference in solubility.

Some typical examples wherein a mixture is obtained are shown below.

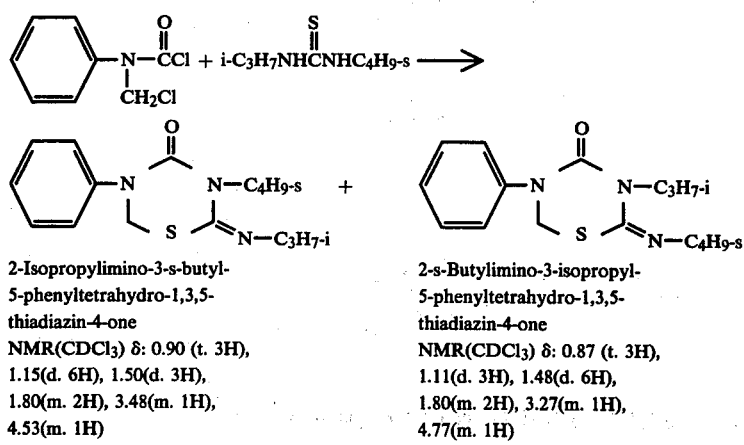

2-Isopropylimino-3-s-butyl-
5-phenyltetrahydro-1,3,5-
thiadiazin-4-one
NMR(CDCl$_3$) δ: 0.90 (t. 3H),
1.15(d. 6H), 1.50(d. 3H),
1.80(m. 2H), 3.48(m. 1H),
4.53(m. 1H)

2-s-Butylimino-3-isopropyl-
5-phenyltetrahydro-1,3,5-
thiadiazin-4-one
NMR(CDCl$_3$) δ: 0.87 (t. 3H),
1.11(d. 3H), 1.48(d. 6H),
1.80(m. 2H), 3.27(m. 1H),
4.77(m. 1H)

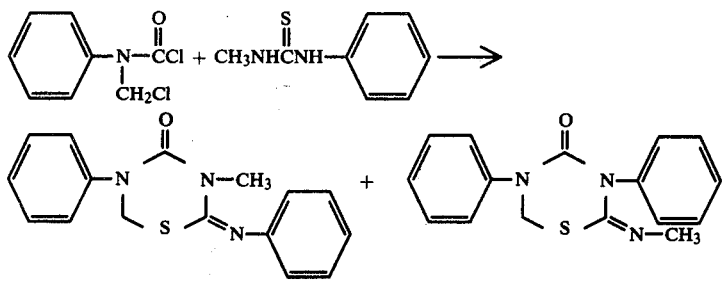

2-Phenylimino-3-methyl-5-
phenyltetrahydro-1,3,5-
thiadiazin-4-one
NMR(CDCl₃) δ:

3.44(s. 3H: —N—CH₃)
           |

4.58(s. 2H: —N—CH₂—S—)
           |

2-Methylimino-3,5-
diphenyltetrahydro-
1,3,5-thiadiazin-4-one
NMR(CDCl₃) δ:

3.04(s. 3H: =N—CH₃)

4.83(s. 2H: —N—CH₂—S—)
           |

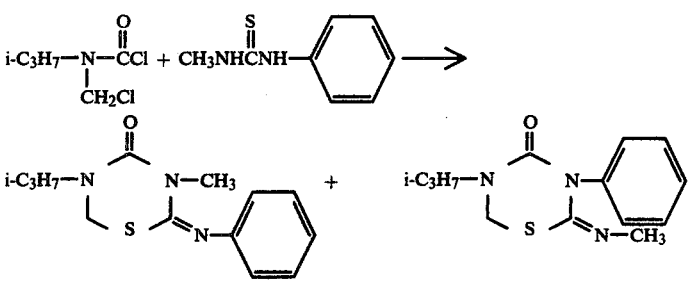

2-Phenylimino-3-methyl-5-
isopropyltetrahydro-1,3,5-
thiadiazin-4-one
NMR(CDCl₃) δ: 3.35(3H . S: —N—CH₃),
                              |

4.02(2H . S: —N—CH₂—S—)
            |

2-Methylimino-3-phenyl-
5-isopropyltetrahydro-
1,3,5-thiadiazin-4-one
NMR(CDCl₃) δ:

2.95(3H . S: =N—CH₃), 4.25(2H . S: —N—CH₂—S—)
            | m.p. 174°–176° C.

It is interesting that as described above, the ring-forming reaction in this invention seems to be associated with the steric structural bulkiness of R² and R³ groups.

The starting compounds represented by the formulae (II) and (III) are explained hereafter. R¹, R² and R³ are defined as previously described. The alkyl groups having 1 to 8 carbon atoms include straight chain and branched chain alkyl groups and can be shown by, for example, methyl, ethyl, n-propyl, isopropyl, n-butyl, isobutyl, t-butyl, s-butyl, n-pentyl, 3-methylbutyl, n-hexyl, heptyl, n-octyl, 1,1,3,3-tetramethylbutyl (t-octyl) and 2-ethylhexyl. The cycloalkyl groups having 3 to 6 carbon atoms include cyclohexyl, cyclopentyl, cyclopropyl and cyclobutyl. Examples of alkoxyalkyl groups having each a total of 3 to 6 carbon atoms are methoxyethyl, methoxypropyl, ethoxyethyl, propoxyethyl and butoxyethyl.

In the substituted phenyl groups represented by R¹, R² and R³, which may be the same or different, the substituent halogens are fluorine, chlorine, bromine and iodine; and the substituent alkyl or alkoxy groups of C₁ to C₄ include straight chain and branched chain groups. Typical examples of such substituted phenyl groups are chlorophenyl, dichlorophenyl, fluorophenyl, methoxyphenyl, ethoxyphenyl, isopropoxyphenyl, trifluoromethylphenyl, chlorotolyl, chloromethoxyphenyl, tolyl and dimethylphenyl groups.

The reaction in this invention is preferably carried out in a solvent which may not seriously interfere with the progress of reaction. Suitable solvents for use are water; aromatic hydrocarbons such as benzene, toluene and xylene; ketones such as acetone, cyclohexanone and methyl ethyl ketone; ethers such as tetrahydrofuran, dioxane and ethyl ether; halogenated hydrocarbons such as chloroform, carbon tetrachloride and chlorobenzene; alcohols such as ethanol and propanol; esters of aliphatic acids such as ethyl acetate; aliphatic amides such as dimethylformamide and dimethylacetamide; dimethyl sulfoxide and other solvents which do not severely interfere with the reaction. These solvents can also be used in combinations such as mixtures of water and organic solvents and mixtures of organic solvents.

The bases for use in the reaction include inorganic bases such as potassium hydroxide, sodium hydroxide, aqueous ammonia, potassium carbonate, sodium carbonate and sodium hydrogen carbonate; and organic bases such as triethylamine, pyridine, and 1,8-diazabicyclo-[5,4,0]-7-undecene. These bases are used, in most of the cases, in the form of aqueous solution, although they can be used in powder form, if available.

The reaction temperature can be selected from a wide range of −10° to 200° C., but the preferable temperature range is from room temperature to about 100° C. for the procedure (A) and from 60° to 130° C. for the procedure (B).

Since the reaction between a thiourea and N-chloromethyl-N-phenylcarbamoyl chloride is equimolar, the reactants are used in an equimolar ratio or in a slight excess of either reactant. The amount to be used of the base for 1 mole of either reactant is 2 moles or in slight excess for the procedure (A) and 1 mole or in slight excess for the procedure (B).

After completion of the reaction, the reaction mixture is treated with a suitable solvent to extract the compound represented by the formula (I) and the extract solution is washed, dried and freed from the solvent to obtain the compound (I) in the form of crystals or oil which, if necessary, is further purified.

When the compound represented by the formula (I) is desired to be recovered in the form of salt, either the procedure (B) is followed or the compound (I) is treated with a desired acid. The acids for use in preparing the salt are common inorganic or organic acids including HCl, HBr, $H_2SO_4$, $H_3PO_4$, $HNO_3$, $HClO_4$, $CH_3COOH$, $CCl_3COOH$, formic acid and benzenesulfonic acid.

Typical examples of the compounds represented by the formula (I) are given below.

In the case of 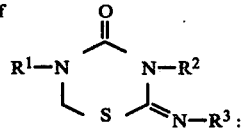 :

| Compound No. | Substituent group $R^1$ | $R^2$ | $R^3$ | Physical property |
|---|---|---|---|---|
| 1 | $CH_3$ | $C_2H_5$ | $C_2H_5$ | m.p. 82°–84° C. |
| 2 | $CH_3$ | $i$-$C_3H_7$ | $i$-$C_3H_7$ | m.p. 76°–77° C. |
| 3 | $CH_3$ | $n$-$C_3H_7$ | $t$-$C_4H_9$ | m.p. 81°–82° C. |
| 4 | $CH_3$ | $n$-$C_6H_{13}$ | $n$-$C_6H_{13}$ | m.p. 63°–65° C. |
| 5 | $C_2H_5$ | $CH_3$ | $CH_3$ | m.p. 43°–44° C. |
| 6 | $C_2H_5$ | $CH_3$ | $t$-$C_4H_9$ | m.p. 68°–69° C. |
| 7 | $C_2H_5$ | $C_2H_5$ | $C_2H_5$ | m.p. 68°–70° C. |
| 8 | $C_2H_5$ | $i$-$C_3H_7$ | $i$-$C_3H_7$ | m.p. 61°–62° C. |
| 9 | $CH_2CH=CH_2CH_3$ | $CH_3$ | $CH_3$ | $n_D^{20}$ 1.5615 |
| 10 | $CH_2CH=CH_2$ | $CH_3$ | $i$-$C_3H_7$ | $n_D^{20}$ 1.5380 |
| 11 | $CH_2CH=CH_2$ | $C_2H_5$ | $C_2H_5$ | $n_D^{20}$ 1.5397 |
| 12 | $CH_2CH=CH_2$ | $n$-$C_3H_7$ | $n$-$C_3H_7$ | $n_D^{20}$ 1.5285 |
| 13 | $n$-$C_3H_7$ | $CH_3$ | $i$-$C_3H_7$ | $n_D^{20}$ 1.5310 |
| 14 | $n$-$C_3H_7$ | $i$-$C_3H_7$ | $i$-$C_3H_7$ | $n_D^{20}$ 1.5166 |
| 15 | $n$-$C_3H_7$ | Benzyl | $i$-$C_3H_7$ | $n_D^{20}$ 1.5185 |
| 16 | $i$-$C_3H_7$ | $CH_3$ | $CH_3$ | m.p. 92°–93° C. |
| 17 | $i$-$C_3H_7$ | $CH_3$ | $C_2H_5$ | m.p. 93°–95° C. |
| 18 | $i$-$C_3H_7$ | $CH_3$ | $i$-$C_3H_7$ | m.p. 87°–88° C. |
| 19 | $i$-$C_3H_7$ | $CH_3$ | Benzyl | m.p. 106°–108° C. |
| 20 | $i$-$C_3H_7$ | $CH_3$ | $n$-$C_6H_{13}$ | $n_D^{20}$ 1.5199 |
| 21 | $i$-$C_3H_7$ | $CH_3$ | 2-Ethylhexyl | $n_D^{20}$ 1.5180 |
| 22 | $i$-$C_3H_7$ | $CH_3$ | $n$-$C_8H_{17}$ | $n_D^{20}$ 1.5167 |
| 23 | $i$-$C_3H_7$ | $C_2H_5$ | $C_2H_5$ | $n_D^{20}$ 1.5264 |
| 24 | $i$-$C_3H_7$ | $n$-$C_3H_7$ | $n$-$C_3H_7$ | $n_D^{20}$ 1.5160 |
| 25 | $n$-$C_4H_9$ | $CH_3$ | $i$-$C_3H_7$ | m.p. 84°–85° C. |
| 26 | $n$-$C_4H_9$ | $C_2H_5$ | $s$-$C_4H_9$ | m.p. 81°–82° C. |
| 27 | $i$-$C_4H_9$ | $i$-$C_3H_7$ | $i$-$C_3H_7$ | m.p. 93°–94° C. |
| 28 | $i$-$C_3H_7$ | $CH_3$ | Cyclohexyl | m.p. 98°–99° C. |
| 29 | $s$-$C_4H_9$ | $CH_3$ | $i$-$C_3H_7$ | m.p. 82°–83° C. |
| 30 | $s$-$C_4H_9$ | $C_2H_5$ | $i$-$C_3H_7$ | m.p. 89°–90° C. |
| 31 | $t$-$C_4H_9$ | $CH_3$ | $CH_3$ | m.p. 51°–52° C. |
| 32 | $t$-$C_4H_9$ | $CH_3$ | $n$-$C_3H_7$ | $n_D^{20}$ 1.5273 |
| 33 | $t$-$C_4H_9$ | $CH_3$ | $i$-$C_3H_7$ | m.p. 62°–63° C. |
| 34 | $t$-$C_4H_9$ | $CH_3$ | $n$-$C_4H_9$ | $n_D^{20}$ 1.5185 |
| 35 | $t$-$C_4H_9$ | $CH_3$ | $s$-$C_4H_9$ | m.p. 83°–84° C. |
| 36 | $t$-$C_4H_9$ | $CH_3$ | $i$-$C_4H_9$ | m.p. 77°–78° C. |
| 37 | $t$-$C_4H_9$ | $CH_3$ | $t$-$C_4H_9$ | m.p. 107°–108° C. |
| 38 | $t$-$C_4H_9$ | $CH_3$ | Benzyl | m.p. 125°–127° C. |
| 39 | $t$-$C_4H_9$ | $CH_3$ | $n$-$C_6H_{13}$ | $n_D^{20}$ 1.5122 |
| 40 | $t$-$C_4H_9$ | $CH_3$ | $n$-$C_8H_{17}$ | m.p. 58°–59° C. |
| 41 | $t$-$C_4H_9$ | $C_2H_5$ | $C_2H_5$ | $n_D^{20}$ 1.5235 |
| 42 | $t$-$C_4H_9$ | $C_2H_5$ | $t$-$C_4H_9$ | $n_D^{20}$ 1.5189 |
| 43 | $t$-$C_4H_9$ | $n$-$C_3H_7$ | $i$-$C_3H_7$ | $n_D^{20}$ 1.5160 |
| 44 | $t$-$C_4H_9$ | $n$-$C_3H_7$ | $n$-$C_4H_9$ | $n_D^{20}$ 1.5096 |
| 45 | $t$-$C_4H_9$ | $n$-$C_4H_9$ | $n$-$C_4H_9$ | $n_D^{20}$ 1.5065 |
| 46 | $t$-$C_4H_9$ | $n$-$C_4H_9$ | $t$-$C_4H_9$ | $n_D^{20}$ 1.5085 |
| 47 | $t$-$C_4H_9$ | Benzyl | $t$-$C_4H_9$ | m.p. 75°–76° C. |
| 48 | $t$-$C_4H_9$ | $i$-$C_3H_7$ | $t$-$C_8H_{17}$ | m.p. 89°–91° C. |
| 49 | $t$-$C_4H_9$ | $n$-$C_8H_{17}$ | $n$-$C_8H_{17}$ | $n_D^{20}$ 1.5003 |
| 50 | $n$-$C_6H_{13}$ | $CH_3$ | $i$-$C_3H_7$ | $n_D^{20}$ 1.5195 |
| 51 | $n$-$C_6H_{13}$ | $i$-$C_3H_7$ | $i$-$C_3H_7$ | $n_D^{20}$ 1.5188 |
| 52 | Cyclohexyl | $i$-$C_3H_7$ | $i$-$C_3H_7$ | $n_D^{20}$ 1.5205 |
| 53 | Cyclohexyl | $CH_3$ | $t$-$C_4H_9$ | $n_D^{20}$ 1.5210 |
| 54 | Benzyl | $CH_3$ | $CH_3$ | m.p. 93°–95° C. |

-continued

In the case of:

$$R^1-N\underset{S}{\overset{\underset{\displaystyle\|}{O}}{\diagdown}}N-R^2$$
$$\phantom{xxxxxx}=N-R^3$$

| Compound No. | R¹ | R² | R³ | Physical property |
|---|---|---|---|---|
| 55 | Benzyl | $C_2H_5$ | $C_2H_5$ | $n_D^{20}$ 1.5630 |
| 56 | Benzyl | $n$-$C_3H_7$ | $n$-$C_3H_7$ | $n_D^{20}$ 1.5653 |
| 57 | Benzyl | Benzyl | $i$-$C_3H_7$ | $n_D^{20}$ 1.5780 |
| 58 | $t$-$C_8H_{17}$ | $CH_3$ | $CH_3$ | m.p. 66°–68° C. |
| 59 | $t$-$C_8H_{17}$ | $CH_3$ | $i$-$C_3H_7$ | $n_D^{20}$ 1.5100 |
| 60 | $t$-$C_8H_{17}$ | $CH_3$ | $CH_2\!=\!CHCH_2$ | $n_D^{20}$ 1.5210 |
| 61 | $t$-$C_8H_{17}$ | $CH_3$ | $n$-$C_4H_9$ | $n_D^{20}$ 1.5112 |
| 62 | $t$-$C_8H_{17}$ | $CH_3$ | $i$-$C_4H_9$ | $n_D^{20}$ 1.5110 |
| 63 | $t$-$C_8H_{17}$ | $CH_3$ | $t$-$C_4H_9$ | m.p. 91°–93° C. |
| 64 | $n$-$C_8H_{17}$ | $CH_3$ | $CH_3$ | $n_D^{20}$ 1.5190 |
| 65 | $n$-$C_8H_{17}$ | $CH_3$ | $i$-$C_3H_7$ | $n_D^{20}$ 1.5185 |
| 66 | $i$-$C_3H_7$ | Phenyl | $CH_3$ | m.p. 174°–176° C. |
| 67 | $i$-$C_3H_7$ | $CH_3$ | 2-methyl-5-chlorophenyl | m.p. 91°–92° C. |
| 68 | $i$-$C_3H_7$ | 2-methyl-5-chlorophenyl | $CH_3$ | m.p. 139°–141° C. |
| 69 | $t$-$C_4H_9$ | Phenyl | $CH_3$ | m.p. 125°–127° C. |
| 70 | $t$-$C_4H_9$ | 4-chlorophenyl | $CH_3$ | m.p. 165°–166° C. |
| 71 | $t$-$C_4H_9$ | 4-fluorophenyl | $CH_3$ | m.p. 150°–151° C. |
| 72 | $t$-$C_4H_9$ | $CH_3$ | 4-methylphenyl | m.p. 113°–115° C. |
| 73 | $t$-$C_4H_9$ | Phenyl | $C_2H_5$ | m.p. 117°–120° C. |
| 74 | $t$-$C_4H_9$ | Phenyl | $n$-$C_3H_7$ | m.p. 109°–110° C. |
| 75 | $t$-$C_4H_9$ | Phenyl | $i$-$C_3H_7$ | m.p. 136°–137° C. |
| 76 | $t$-$C_4H_9$ | Phenyl | $n$-$C_4H_9$ | m.p. 115°–116° C. |
| 77 | $t$-$C_4H_9$ | Phenyl | $t$-$C_4H_9$ | m.p. 133°–134° C. |
| 78 | $t$-$C_4H_9$ | Phenyl | Phenyl | m.p. 111°–112° C. |
| 79 | $t$-$C_4H_9$ | Phenyl | $n$-$C_8H_{17}$ | m.p. 59° C. |
| 80 | $t$-$C_4H_9$ | 4-methylphenyl | $C_2H_5$ | m.p. 157°–158° C. |
| 81 | $t$-$C_4H_9$ | 2,4-dimethylphenyl | $C_2H_5$ | m.p. 103°–104° C. |
| 82 | $t$-$C_4H_9$ | 2-methyl-4-chlorophenyl | $CH_3$ | m.p. 124°–125° C. |
| 83 | $t$-$C_4H_9$ | 3,4-dichlorophenyl | $CH_3$ | m.p. 140°–141° C. |
| 84 | $t$-$C_4H_9$ | 4-methoxyphenyl | $C_2H_5$ | m.p. 116°–117° C. |
| 85 | Benzyl | Phenyl | $CH_3$ | m.p. 109°–110° C. |
| 86 | Benzyl | Phenyl | Cyclohexyl | m.p. 101°–102° C. |
| 87 | Benzyl | 2-methoxy-5-chlorophenyl | $i$-$C_3H_7$ | m.p. 1131°–132° C. |
| 88 | $t$-$C_8H_{17}$ | Phenyl | $CH_3$ | m.p. 121°–122° C. |
| 89 | $t$-$C_8H_{17}$ | 2-methoxyphenyl | $n$-$C_3H_7$ | m.p. 118°–119° C. |

-continued

In the case of

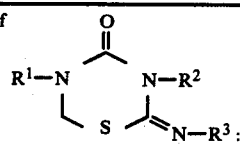

| Compound No. | R¹ | R² | R³ | Physical property |
|---|---|---|---|---|
| 90 | t-C$_8$H$_{17}$ | (3-CF$_3$-phenyl) | s-C$_4$H$_9$ | m.p. 93°–94° C. |
| 91 | i-C$_3$H$_7$ | CH$_3$ | Phenyl | NMR spectrum (described before) |
| 92 | i-C$_3$H$_7$ | CH$_3$ | H | n$_D^{20}$ 1.5095 |
| 93 | t-C$_4$H$_9$ | CH$_2$=CHCH$_2$ | CH$_2$=CHCH$_2$ | m.p. 62°–63° C. |
| 94 | t-C$_4$H$_9$ | n-C$_3$H$_7$ | Benzyl | m.p. 45°–46° C. |
| 95 | t-C$_4$H$_9$ | (CH$_3$)$_2$CHCH$_2$CH$_2$ | t-C$_4$H$_9$ | n$_D^{20}$ 1.5477 |
| 96 | t-C$_4$H$_9$ | Cyclohexyl | Cyclohexyl | n$_D^{20}$ 1.5610 |
| 97 | n-C$_6$H$_{13}$ | CH$_3$ | CH$_3$ | n$_D^{20}$ 1.5265 |
| 98 | n-C$_6$H$_{13}$ | n-C$_4$H$_9$ | i-C$_3$H$_7$ | n$_D^{20}$ 1.5265 |
| 99 | Cyclohexyl | i-C$_4$H$_9$ | t-C$_4$H$_9$ | n$_D^{20}$ 1.5565 |
| 100 | Cyclohexyl | n-C$_6$H$_{13}$ | i-C$_3$H$_7$ | n$_D^{20}$ 1.5781 |
| 101 | t-C$_8$H$_{17}$ | C$_2$H$_5$ | C$_2$H$_5$ | n$_D^{20}$ 1.5116 |
| 102 | n-C$_4$H$_9$—CH(C$_2$H$_5$)CH$_2$ | CH$_3$ | i-C$_3$H$_7$ | n$_D^{20}$ 1.5102 |
| 103 | n-C$_4$H$_9$—CH(C$_2$H$_5$)CH$_2$ | CH$_2$=CHCH$_2$ | i-C$_3$H$_7$ | n$_D^{20}$ 1.5178 |
| 104 | s-C$_4$H$_9$ | Cyclopentyl | t-C$_4$H$_9$ | m.p. 130°–130.5° C. |
| 105 | s-C$_4$H$_9$ | C$_2$H$_5$OCH$_2$CH$_2$ | i-C$_3$H$_7$ | n$_D^{26}$ 1.5019 |
| 106 | s-C$_4$H$_9$ | (4-Cl-phenyl) | (4-Cl-phenyl) | m.p. 130°–131° C. |
| 107 | t-C$_4$H$_9$ | H | s-C$_4$H$_9$ | m.p. 98°–100° C. |
| 108 | t-C$_4$H$_9$ | C$_2$H$_5$ | H | m.p. 221°–222° C. |
| 109 | t-C$_4$H$_9$ | H | H | m.p. 123°–125° C. |
| 110 | Cyclopentyl | CH$_3$ | CH$_3$ | n$_D^{24}$ 1.5370 |
| 111 | Cyclopentyl | i-C$_3$H$_7$ | i-C$_3$H$_7$ | n$_D^{24}$ 1.5156 |
| 112 | CH$_3$OCH$_2$CH$_2$CH$_2$ | CH$_3$ | i-C$_3$H$_7$ | n$_D^{24}$ 1.5043 |
| 113 | CH$_3$OCH$_2$CH$_2$CH$_2$ | CH$_3$ | Benzyl | n$_D^{24}$ 1.5590 |
| 114 | Cyclopentyl | Benzyl | Benzyl | m.p. 85°–86° C. |

In the case of

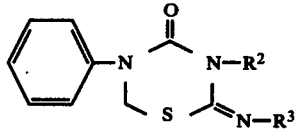

| Compound No. | R² | R³ | Physical property |
|---|---|---|---|
| 115 | CH$_3$ | CH$_3$ | m.p. 68°–70° C. |
| 116 | CH$_3$ | C$_2$H$_5$ | n$_D^{20}$ 1.6034 |
| 117 | CH$_3$ | n-C$_3$H$_7$ | n$_D^{20}$ 1.5902 |
| 118 | CH$_3$ | i-C$_3$H$_7$ | m.p. 72°–73.5° C. |
| 119 | CH$_3$ | n-C$_4$H$_9$ | m.p. 30°–35° C. |
| 120 | CH$_3$ | t-C$_4$H$_9$ | m.p. 87°–90° C. |
| 121 | CH$_3$ | Benzyl | m.p. 90°–92° C. |
| 122 | CH$_3$ | n-C$_8$H$_{17}$ | n$_D^{20}$ 1.5551 |
| 123 | CH$_3$ | H | m.p. 101°–103° C. |
| 124 | CH$_3$ | (2-CH$_3$-phenyl) | m.p. 113°–114° C. |
| 125 | C$_2$H$_5$ | C$_2$H$_5$ | m.p. 55°–58° C. |
| 126 | C$_2$H$_5$ | n-C$_3$H$_7$ | n$_D^{20}$ 1.5800 |
| 127 | C$_2$H$_5$ | i-C$_3$H$_7$ | m.p. 69°–71° C. |
| 128 | C$_2$H$_5$ | n-C$_4$H$_9$ | n$_D^{20}$ 1.5709 |
| 129 | C$_2$H$_5$ | i-C$_4$H$_9$ | m.p. 85°–88° C. |
| 130 | C$_2$H$_5$ | s-C$_4$H$_9$ | m.p. 88°–89° C. |
| 131 | C$_2$H$_5$ | t-C$_4$H$_9$ | m.p. 93°–94° C. |
| 132 | C$_2$H$_5$ | Cyclohexyl | m.p. 133°–135° C. |

-continued

In the case of

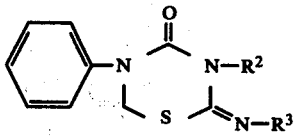

| Compound No. | R² | R³ | Physical property |
|---|---|---|---|
| 133 | C$_2$H$_5$ | n-C$_8$H$_{17}$ | n$_D^{20}$ 1.5468 |
| 134 | n-C$_3$H$_7$ | n-C$_3$H$_7$ | n$_D^{20}$ 1.5090 |
| 135 | n-C$_3$H$_7$ | i-C$_3$H$_7$ | n$_D^{20}$ 1.5646 |
| 136 | n-C$_3$H$_7$ | s-C$_4$H$_9$ | n$_D^{20}$ 1.5579 |
| 137 | n-C$_3$H$_7$ | t-C$_4$H$_9$ | m.p. 65°–67° C. |
| 138 | n-C$_3$H$_7$ | Cyclohexyl | n$_D^{20}$ 1.5697 |
| 139 | CH$_2$=CHCH$_2$ | CH$_2$=CHCH$_2$ | n$_D^{20}$ 1.5941 |
| 140 | CH$_2$=CHCH$_2$ | n-C$_3$H$_7$ | n$_D^{26}$ 1.5753 |
| 141 | CH$_2$=CHCH$_2$ | i-C$_3$H$_7$ | n$_D^{26}$ 1.5722 |
| 142 | CH$_2$=CHCH$_2$ | s-C$_4$H$_9$ | n$_D^{26}$ 1.5719 |
| 143 | CH$_2$=CHCH$_2$ | t-C$_4$H$_9$ | m.p. 46°–47° C. |
| 144 | i-C$_3$H$_7$ | i-C$_3$H$_7$ | m.p. 92°–94° C. |
| 145 | i-C$_3$H$_7$ | t-C$_4$H$_9$ | m.p. 104°–106° C. |
| 146 | n-C$_4$H$_9$ | n-C$_4$H$_9$ | n$_D^{20}$ 1.5604 |
| 147 | n-C$_4$H$_9$ | i-C$_3$H$_7$ | n$_D^{20}$ 1.5580 |
| 148 | i-C$_4$H$_9$ | i-C$_4$H$_9$ | m.p. 82°–83° C. |
| 149 | i-C$_4$H$_9$ | i-C$_3$H$_7$ | m.p. 80°–82° C. |
| 150 | i-C$_4$H$_9$ | t-C$_4$H$_9$ | m.p. 75°–77° C. |
| 151 | s-C$_4$H$_9$ | s-C$_4$H$_9$ | n$_D^{20}$ 1.5561 |
| 152 | s-C$_4$H$_9$ | t-C$_4$H$_9$ | n$_D^{20}$ 1.5544 |
| 153 | n-C$_6$H$_{13}$ | i-C$_3$H$_7$ | n$_D^{26}$ 1.5464 |

-continued

In the case of

Ph-N(C(=O)-N-R²)-CH₂-S-C(=N-R³)

| Compound No. | R² | R³ | Physical property |
|---|---|---|---|
| 154 | n-C₆H₁₃ | n-C₆H₁₃ | $n_D^{20}$ 1.5420 |
| 155 | Cyclohexyl | t-C₄H₉ | m.p. 86°–89° C. |
| 156 | i-C₃H₇ | t-C₈H₁₇ | $n_D^{25}$ 1.5382 |
| 157 | s-C₄H₉ | t-C₈H₁₇ | $n_D^{20}$ 1.5461 |
| 158 | Benzyl | i-C₃H₇ | m.p. 124°–125° C. |
| 159 | Benzyl | t-C₄H₉ | $n_D^{26}$ 1.5910 |
| 160 | n-C₈H₁₇ | i-C₃H₇ | $n_D^{20}$ 1.5400 |
| 161 | n-C₈H₁₇ | s-C₄H₉ | $n_D^{20}$ 1.5351 |
| 162 | Phenyl | C₂H₅ | m.p. 113°–115° C. |
| 163 | Phenyl | s-C₄H₉ | m.p. 134°–135.5° C. |
| 164 | 4-Cl-C₆H₄ | i-C₃H₇ | m.p. 175°–177° C. |
| 165 | 2-CH₃O-5-CH₃-C₆H₃ | C₂H₅ | m.p. 116°–117° C. |
| 166 | 5-Cl-2-CH₃-C₆H₃ | CH₃ | m.p. 121°–123° C. |
| 167 | 4-F-C₆H₄ | i-C₃H₇ | m.p. 182°–184° C. |
| 168 | 3-CF₃-C₆H₄ | s-C₄H₉ | $n_D^{20}$ 1.5538 |
| 169 | Phenyl | Phenyl | m.p. 193°–194° C. |
| 170 | 3-OCH₃-4-Cl-C₆H₃ | C₂H₅ | m.p. 136°–137° C. |
| 171 | 3,4-(CH₃)₂-C₆H₃ | CH₃ | m.p. 111°–112° C. |
| 172 | 3,4-Cl₂-C₆H₃ | n-C₃H₇ | m.p. 146°–147° C. |
| 173 | s-C₄H₉ | i-C₃H₇ | NMR spectrum } described before |
| 174 | i-C₃H₇ | s-C₄H₉ | NMR spectrum |
| 175 | CH₃ | Phenyl | NMR spectrum |
| 176 | Phenyl | CH₃ | NMR spectrum |
| 177 | CH₃ | 5-Cl-2-CH₃-C₆H₃ | Obtained as a mixture with compound No. 166 |
| 178 | H | H | m.p. 176° C. (decomp.) |
| 179 | CH₃OCH₂CH₂ | i-C₃H₇ | $n_D^{20}$ 1.5640 |
| 180 | CH₃OCH₂CH₂ | t-C₄H₉ | $n_D^{20}$ 1.5559 |
| 181 | C₂H₅OCH₂CH₂ | i-C₃H₇ | $n_D^{20}$ 1.5572 |
| 182 | C₂H₅OCH₂CH₂ | t-C₄H₉ | m.p. 74°–75.5° C. |
| 183 | Cyclopentyl | t-C₄H₉ | m.p. 103°–104° C. |
| 184 | t-C₄H₉ | t-C₄H₉ | m.p. 109°–115° C. |
| 185 | 4-Cl-C₆H₄ | 4-Cl-C₆H₄ | m.p. 172°–175° C. |

In the case of X-C₆H₄-N(C(=O)-N-R²)-CH₂-S-C(=N-R³)

| Compound No. | X | R² | R³ | Physical property |
|---|---|---|---|---|
| 186 | 4-Cl | H | i-C₃H₇ | m.p. 190°–197° C. (decomp.) |
| 187 | 4-Cl | H | t-C₄H₉ | m.p. 210°–214° C. (decomp.) |
| 188 | 4-Cl | CH₃ | CH₃ | m.p. 98°–100° C. |
| 189 | 4-Cl | CH₃ | i-C₃H₇ | m.p. 106°–108° C. |
| 190 | 4-Cl | C₂H₅ | C₂H₅ | m.p. 123°–125° C. |
| 191 | 4-Cl | C₂H₅ | t-C₄H₉ | m.p. 154°–157° C. |
| 192 | 4-Cl | n-C₃H₇ | n-C₃H₇ | m.p. 81°–82° C. |
| 193 | 4-Cl | n-C₃H₇ | i-C₃H₇ | m.p. 61°–63° C. |
| 194 | 4-Cl | i-C₃H₇ | i-C₃H₇ | m.p. 127°–129° C. |
| 195 | 4-Cl | n-C₃H₇ | t-C₄H₉ | m.p. 68°–69° C. |
| 196 | 4-Cl | i-C₃H₇ | t-C₄H₉ | m.p. 123°–125° C. |
| 197 | 4-Cl | s-C₄H₉ | s-C₄H₉ | m.p. 102°–103° C. |
| 198 | 4-Cl | s-C₄H₉ | t-C₄H₉ | m.p. 99°–100° C. |
| 199 | 4-Cl | CH₂=CHCH₂ | CH₂=CHCH₂ | $n_D^{30}$ 1.6003 |
| 200 | 4-Cl | CH₂=CHCH₂ | i-C₃H₇ | $n_D^{30}$ 1.5833 |
| 201 | 4-Cl | CH₃ | —CH₂—C₆H₅ | $n_D^{28}$ 1.6293 |
| 202 | 4-Cl | CH₂=CHCH₂ | —CH₂—C₆H₅ | $n_D^{28}$ 1.6221 |

-continued

In the case of $$X-\text{C}_6\text{H}_4-N(\text{CH}_2\text{S})-C(=O)-N(R^2)-C(=N-R^3)$$

| Compound No. | X | $R^2$ | $R^3$ | Physical property |
|---|---|---|---|---|
| 203 | 4-Cl | $-CH_2-C_6H_5$ | i-$C_3H_7$ | $n_D^{28}$ 1.5978 |
| 204 | 4-Cl | $-CH_2-C_6H_5$ | t-$C_4H_9$ | m.p. 87°–89° C. |
| 205 | 4-Cl | $-C_6H_4-F$ | i-$C_3H_7$ | m.p. 153°–155° C. |
| 206 | 4-Cl | i-$C_3H_7$ | t-$C_8H_{17}$ | m.p. 124°–125° C. |
| 207 | 4-Cl | $CH_3OC_2H_4$ | i-$C_3H_7$ | $n_D^{20}$ 1.5728 |
| 208 | 4-Cl | cyclohexyl | t-$C_4H_9$ | m.p. 147°–148° C. |
| 209 | 4-Cl | $C_6H_5$ | $CH_3$ | m.p. 187°–188° C. |
| 210 | 4-Cl | $CH_3$ (2,4-diCH$_3$-C$_6$H$_3$)* | $CH_3$ | m.p. 148°–149° C. |
| 211 | 4-Cl | $-C_6H_4-OCH_3$ | $C_2H_5$ | m.p. 149°–150° C. |
| 212 | 4-Cl | $CH_3$ | n-$C_6H_{13}$ | m.p. 75°–76° C. |
| 213 | 3-Cl | $CH_3$ | $CH_3$ | m.p. 111°–112° C. (HCl salt: m.p. 180°–183° C. decomp.) |
| 214 | 3-Cl | $CH_3$ | i-$C_3H_7$ | m.p. 108°–111° C. |
| 215 | 3-Cl | $C_2H_5$ | $C_2H_5$ | m.p. 106°–108° C. (HCl salt: m.p. 199°–200° C.) |
| 216 | 3-Cl | $C_2H_5$ | t-$C_4H_9$ | m.p. 62°–63° C. |
| 217 | 3-Cl | $CH_2CH=CH_2$ | i-$C_3H_7$ | $n_D^{19}$ 1.5857 (HCl salt: m.p. 179° C. decomp.) |
| 218 | 3-Cl | $CH_2CH=CH_2$ | t-$C_4H_9$ | $n_D^{19}$ 1.5796 |
| 219 | 3-Cl | $CH_2CH=CH_2$ | $-CH_2-C_6H_5$ | $n_D^{19}$ 1.6107 |
| 220 | 3-Cl | i-$C_3H_7$ | i-$C_3H_7$ | m.p. 81°–82° C. |
| 221 | 3-Cl | i-$C_3H_7$ | t-$C_4H_9$ | m.p. 113°–115° C. (HCl salt: m.p. 152° C. decomp.) |
| 222 | 3-Cl | i-$C_3H_7$ | t-$C_8H_{17}$ | $n_D^{19}$ 1.5406 |
| 223 | 3-Cl | i-$C_4H_9$ | t-$C_4H_9$ | $n_D^{20}$ 1.5542 |
| 224 | 3-Cl | s-$C_4H_9$ | s-$C_4H_9$ | $n_D^{20}$ 1.5652 |
| 225 | 3-Cl | s-$C_4H_9$ | t-$C_4H_9$ | m.p. 75°–76° C. (HCl salt: m.p. 186° C. decomp.) |
| 226 | 3-Cl | $-C_6H_4-CH_3$ | $CH_3$ | m.p. 185°–186° C. |
| 227 | 3-Cl | $CH_3$ (2-CH$_3$-5-Cl-C$_6$H$_3$)* | $CH_3$ | m.p. 148°–149° C. |
| 228 | 3-Cl | $CH_3OC_4H_9$ | i-$C_3H_7$ | $n_D^{20}$ 1.5731 |
| 229 | 3-Cl | $CH_3OC_2H_4$ | t-$C_4H_9$ | $n_D^{20}$ 1.5711 |
| 230 | 3-Cl | i-$C_3H_7$ | cyclohexyl | m.p. 105°–106° C. |
| 231 | 3-Cl | $C_6H_5$ | $C_6H_5$ | m.p. 158°–159° C. |
| 232 | 3-Cl | n-$C_3H_7$ | t-$C_4H_9$ | $n_D^{22}$ 1.5740 |
| 233 | 3-Cl | cyclohexyl | i-$C_3H_7$ | $n_D^{20}$ 1.5750 |
| 234 | 3-Cl | n-$C_6H_{13}$ | i-$C_3H_7$ | $n_D^{20}$ 1.5635 |

-continued

In the case of:

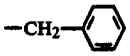

| Compound No. | X | R² | R³ | Physical property |
|---|---|---|---|---|
| 235 | 3-Cl | —CH₂CH₂CH(CH₃)CH₃ | s-C₄H₉ | $n_D^{20}$ 1.5518 |
| 236 | 3-Cl | n-C₄H₉ | t-C₄H₉ | $n_D^{23}$ 1.5600 |
| 237 | 3-Cl | —CH(CH₃)—C₆H₅ | i-C₃H₇ | m.p. 158°–159° C. |
| 238 | 2-Cl | CH₃ | CH₃ | m.p. 142°–144° C. (HCl salt: m.p. 198°–200° C. decomp.) |
| 239 | 2-Cl | C₂H₅ | C₂H₅ | m.p. 90°–92° C. (HCl salt: m.p. 167°–170° C. decomp.) |
| 240 | 2-Cl | CH₃ | i-C₃H₇ | $n_D^{22}$ 1.5725 |
| 241 | 2-Cl | C₂H₅ | t-C₄H₉ | m.p. 94°–96° C. |
| 242 | 2-Cl | CH₂=CHCH₂ | i-C₃H₇ | $n_D^{13}$ 1.5831 |
| 243 | 2-Cl | CH₂=CHCH₂ | t-C₄H₉ | m.p. 105°–107° C. |
| 244 | 2-Cl | i-C₃H₇ | i-C₃H₇ | m.p. 95°–96° C. |
| 245 | 2-Cl | i-C₃H₇ | t-C₄H₉ | m.p. 88°–89° C. (HCl salt: m.p. 201° C. decomp.) |
| 246 | 2-Cl | i-C₃H₇ | n-C₆H₁₃ | $n_D^{13}$ 1.5581 |
| 247 | 2-Cl | i-C₃H₇ | t-C₈H₁₇ | $n_D^{13}$ 1.5822 |
| 248 | 2-Cl | s-C₄H₉ | s-C₄H₉ | m.p. 89°–90° C. |
| 249 | 2-Cl | s-C₄H₉ | t-C₄H₉ | m.p. 67°–68° C. |
| 250 | 2-Cl | —CH₂—C₆H₅ | i-C₃H₇ | m.p. 95°–97° C. |
| 251 | 2-Cl | —CH₂—C₆H₅ | —CH₂—C₆H₅ | (HCl salt: m.p. 127°–130° C. decomp.) |
| 252 | 2-Cl | i-C₃H₇ | cyclohexyl | m.p. 123°–125° C. |
| 253 | 2-Cl | i-C₄H₉ | s-C₄H₉ | $n_D^{21}$ 1.5582 |
| 254 | 2-Cl | n-C₆H₁₃ | i-C₃H₇ | $n_D^{13}$ 1.5581 |
| 255 | 2-Cl | —CH₂-furyl | i-C₃H₇ | m.p. 75°–77° C. |
| 256 | 2-Cl | —C₆H₅ | C₂H₅ | m.p. 77°–79° C. |
| 257 | 2-Cl | —C₆H₄—Cl | CH₃ | m.p. 167°–168° C. |
| 258 | 2-Cl | CH₃OCH₂CH₂CH₂ | t-C₄H₉ | m.p. 87°–88° C. |
| 259 | 3-CF₃ | CH₃ | i-C₃H₇ | $n_D^{30}$ 1.5264 |
| 260 | 3-CF₃ | C₂H₅ | C₂H₅ | $n_D^{30}$ 1.5268 |
| 261 | 3-CF₃ | C₂H₅ | t-C₄H₉ | $n_D^{30}$ 1.5165 |
| 262 | 3-CF₃ | CH₂=CHCH₂ | i-C₃H₇ | $n_D^{24}$ 1.5357 |
| 263 | 3-CF₃ | n-C₃H₇ | n-C₃H₇ | $n_D^{30}$ 1.5233 |
| 264 | 3-CF₃ | n-C₃H₇ | i-C₃H₇ | $n_D^{24}$ 1.5262 |
| 265 | 3-CF₃ | i-C₃H₇ | i-C₃H₇ | m.p. 67°–68° C. |
| 266 | 3-CF₃ | i-C₃H₇ | t-C₈H₁₇ | $n_D^{24}$ 1.5089 |
| 267 | 3-CF₃ | CH₂=CHCH₂ | s-C₄H₉ | $n_D^{24}$ 1.5392 |
| 268 | 3-CF₃ | CH₂=CHCH₂ | t-C₄H₉ | $n_D^{24}$ 1.5262 |
| 269 | 3-CF₃ | i-C₃H₇ | s-C₄H₉ | $n_D^{24}$ 1.5219 |
| 270 | 3-CF₃ | i-C₃H₉ | t-C₃H₇ | m.p. 52°–53° C. (HCl salt: m.p. 160°–164° C.) |
| 271 | 3-CF₃ | i-C₄H₉ | s-C₄H₉ | $n_D^{24}$ 1.5140 |
| 272 | 3-CF₃ | s-C₄H₉ | s-C₄H₉ | $n_D^{24}$ 1.5238 |
| 273 | 3-CF₃ | i-C₄H₉ | t-C₄H₉ | $n_D^{24}$ 1.5130 |
| 274 | 3-CF₃ | s-C₄H₉ | t-C₄H₉ | (HCl salt: m.p. 186.4° C. decomp.) |
| 275 | 4-F | H | i-C₃H₇ | m.p. 188°–190° C. |
| 276 | 4-F | H | t-C₄H₉ | m.p. 205°–212° C. decomp. |
| 277 | 4-F | CH₃ | CH₃ | m.p. 105°–106° C. (HCl salt: m.p. 221° C. decomp.) |

-continued

In the case of 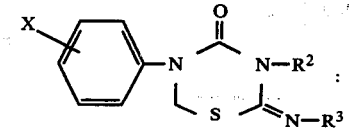

| Compound No. | X | R² | R³ | Physical property |
|---|---|---|---|---|
| 278 | 4-F | C₂H₅ | C₂H₅ | m.p. 99°–100° C. (HCl salt: m.p. 185° C. decomp.) |
| 279 | 4-F | CH₃ | i-C₃H₇ | m.p. 119°–120° C. (HCl salt: m.p. 202° C. decomp.) |
| 280 | 4-F | C₂H₅ | t-C₄H₉ | m.p. 99°–100° C. |
| 281 | 4-F | n-C₃H₇ | n-C₆H₁₃ | n_D²⁰ 1.5596 |
| 282 | 4-F | i-C₃H₇ | t-C₄H₉ | m.p. 109°–110° C. |
| 283 | 4-F | s-C₄H₉ | s-C₄H₉ | m.p. 55°–56° C. |
| 284 | 4-F | s-C₄H₉ | t-C₄H₉ | m.p. 61°–62° C. |
| 285 | 4-F | i-C₃H₇ | i-C₃H₇ | m.p. 119°–120° C. |
| 286 | 4-F | CH₃ (o-tolyl) | i-C₃H₇ | m.p. 141°–142° C. |
| 287 | 4-F | C₂H₅ | H | m.p. 88°–91° C. |
| 288 | 4-F | cyclopentyl | t-C₄H₉ | m.p. 103°–104° C. |
| 289 | 4-F | CH₃ | CH₂CH=CH₂ | m.p. 81°–82° C. |
| 290 | 4-F | 3-Cl-phenyl | C₂H₅ | m.p. 162°–163° C. |
| 291 | 4-Br | CH₃ | CH₃ | m.p. 136°–137° C. |
| 292 | 4-Br | C₂H₅ | t-C₄H₉ | m.p. 131°–132° C. |
| 293 | 4-Br | i-C₃H₇ | i-C₃H₇ | m.p. 121°–122° C. |
| 294 | 4-Br | i-C₃H₇ | t-C₄H₉ | m.p. 117°–118° C. |
| 295 | 4-Br | s-C₄H₉ | t-C₄H₉ | m.p. 68°–69° C. |
| 296 | 2-CH₃ | CH₃ | CH₃ | m.p. 116°–117° C. |
| 297 | 2-CH₃ | CH₃ | i-C₃H₇ | n_D²⁰ 1.5703 |
| 298 | 2-CH₃ | C₂H₅ | C₂H₅ | m.p. 75°–76° C. |
| 299 | 2-CH₃ | C₂H₅ | t-C₄H₉ | m.p. 92° C. |
| 300 | 2-CH₃ | CH₂=CHCH₂ | t-C₄H₉ | m.p. 90.8° C. |
| 301 | 2-CH₃ | i-C₃H₇ | i-C₃H₇ | n_D²⁰ 1.5587 |
| 302 | 2-CH₃ | i-C₃H₇ | t-C₄H₉ | m.p. 97.5°–99° C. |
| 303 | 2-CH₃ | s-C₄H₉ | t-C₄H₉ | n_D²⁰ 1.5483 |
| 304 | 2-CH₃ | n-C₆H₁₃ | i-C₃H₇ | n_D²⁰ 1.5421 |
| 305 | 2-CH₃ | i-C₃H₇ | cyclohexyl | m.p. 87° C. |
| 306 | 2-CH₃ | —CH₂—phenyl | i-C₃H₇ | m.p. 91.1° C. |
| 307 | 2-CH₃ | cyclohexyl | cyclohexyl | n_D²⁰ 1.5568 |
| 308 | 2-CH₃ | —CH₂—phenyl | —CH₂—phenyl | n_D²⁰ 1.5568 |
| 309 | 4-CH₃ | CH₃ | CH₃ | m.p. 80°–81° C. |
| 310 | 4-CH₃ | CH₃ | i-C₃H₇ | m.p. 90°–91° C. |
| 311 | 4-CH₃ | CH₃ | t-C₄H₉ | m.p. 102°–105° C. |
| 312 | 4-CH₃ | C₂H₅ | t-C₄H₉ | m.p. 83°–85° C. |
| 313 | 4-CH₃ | n-C₃H₇ | n-C₃H₇ | m.p. 62°–64° C. |
| 314 | 4-CH₃ | n-C₃H₇ | i-C₃H₇ | m.p. 89°–90° C. |
| 315 | 4-CH₃ | CH₂=CHCH₂ | i-C₃H₇ | n_D²⁰ 1.5722 |
| 316 | 4-CH₃ | i-C₃H₇ | i-C₃H₇ | m.p. 118°–119° C. |
| 317 | 4-CH₃ | n-C₃H₇ | t-C₄H₉ | m.p. 89°–90° C. |
| 318 | 4-CH₃ | i-C₃H₇ | t-C₄H₉ | m.p. 118°–120° C. |
| 319 | 4-CH₃ | s-C₄H₉ | t-C₄H₉ | m.p. 85°–87° C. |
| 320 | 4-CH₃ | —CH₂—phenyl | i-C₃H₇ | m.p. 100°–101° C. |
| 321 | 4-CH₃ | —CH₂—phenyl | —CH₂—phenyl | m.p. 152°–153° C. |
| 322 | 4-CH₃ | 4-Cl-phenyl | i-C₃H₇ | m.p. 201°–203° C. |

-continued

In the case of 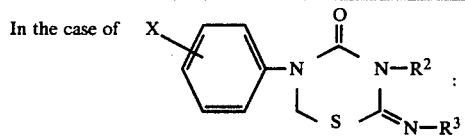

| Compound No. | X | R² | R³ | Physical property |
|---|---|---|---|---|
| 323 | 4-CH₃ | —C₆H₅ (phenyl) | t-C₄H₉ | m.p. 158°–160° C. |
| 324 | 3-CH₃ | C₂H₅ | C₂H₅ | $n_D^{20}$ 1.5814 |
| 325 | 3-CH₃ | i-C₃H₇ | i-C₃H₇ | m.p. 71.0° C. |
| 326 | 3-CH₃ | i-C₃H₇ | t-C₄H₉ | m.p. 104.3° C. |
| 327 | 3-CH₃ | s-C₄H₉ | s-C₄H₉ | $n_D^{20}$ 1.5528 |
| 328 | 3-CH₃ | s-C₄H₉ | t-C₄H₉ | $n_D^{20}$ 1.5546 |
| 329 | 3-CH₃ | —CH₂—C₆H₅ | i-C₃H₇ | m.p. 82°–84° C. |
| 330 | 3-CH₃ | n-C₆H₁₃ | i-C₃H₇ | $n_D^{20}$ 1.5465 |
| 331 | 4-C₂H₅ | CH₃ | CH₃ | $n_D^{20}$ 1.5922 |
| 332 | 4-C₂H₅ | i-C₃H₇ | i-C₃H₇ | m.p. 81°–82.5° C. |
| 333 | 4-C₂H₅ | i-C₃H₇ | t-C₄H₉ | m.p. 70°–72° C. |
| 334 | 4-C₂H₅ | s-C₄H₉ | t-C₄H₉ | m.p. 67.5° C. |
| 335 | 2-C₂H₅ | CH₃ | CH₃ | m.p. 122.0° C. |
| 336 | 2-C₂H₅ | CH₂=CHCH₂ | i-C₃H₇ | $n_D^{20}$ 1.5601 |
| 337 | 2-C₂H₅ | i-C₃H₇ | i-C₃H₇ | $n_D^{20}$ 1.5510 |
| 338 | 2-C₂H₅ | i-C₃H₇ | t-C₄H₉ | $n_D^{20}$ 1.5463 |
| 339 | 2-C₂H₅ | s-C₄H₉ | t-C₄H₉ | $n_D^{20}$ 1.5401 |
| 340 | 2-C₃H₇-i | CH₃ | CH₃ | m.p. 101°–102° C. |
| 341 | 2-C₃H₇-i | C₂H₅ | t-C₄H₉ | m.p. 84°–85° C. |
| 342 | 2-C₃H₇-i | i-C₃H₇ | i-C₃H₇ | m.p. 85°–86° C. |
| 343 | 2-C₃H₇-i | i-C₃H₇ | t-C₄H₉ | m.p. 108°–109° C. |
| 344 | 2-C₃H₇-i | s-C₄H₉ | t-C₄H₉ | m.p. 74°–76° C. |
| 345 | 2-C₃H₇-i | CH₂=CHCH₂ | CH₂=CHCH₂ | m.p. 93°–95° C. |
| 346 | 2-C₃H₇-i | CH₂=CHCH₂ | i-C₃H₇ | $n_D^{20}$ 1.5526 |
| 347 | 4-CH₃O | CH₃ | i-C₃H₇ | m.p. 69.5° C. |
| 348 | 4-CH₃O | C₂H₅ | C₂H₅ | m.p. 100° C. |
| 349 | 4-CH₃O | C₂H₅ | t-C₄H₉ | $n_D^{20}$ 1.5591 |
| 350 | 4-CH₃O | CH₂=CHCH₂ | i-C₃H₇ | m.p. 80.1° C. |
| 351 | 4-CH₃O | n-C₃H₇ | i-C₃H₇ | m.p. 96°–97° C. |
| 352 | 4-CH₃O | i-C₃H₇ | i-C₃H₇ | m.p. 67°–68° C. |
| 353 | 4-CH₃O | i-C₃H₇ | t-C₄H₉ | m.p. 99°–101.5° C. |
| 354 | 4-CH₃O | n-C₃H₇ | —C₆H₁₁ (cyclohexyl) | m.p. 85.5° C. |
| 355 | 4-CH₃O | s-C₄H₉ | t-C₄H₉ | m.p. 63° C. |
| 356 | 4-CH₃O | —CH₂—C₆H₅ | i-C₃H₇ | m.p. 114° C. |
| 357 | 4-CH₃O | n-C₈H₁₇ | s-C₄H₉ | $n_D^{20}$ 1.5296 |
| 358 | 4-CH₃O | —C₆H₅ (phenyl) | t-C₄H₉ | m.p. 167°–168° C. |
| 359 | 4-CH₃O | —C₆H₃Cl₂ (2,3-dichlorophenyl) | i-C₃H₇ | m.p. 159.1° C. |
| 360 | 2-CH₃O | i-C₃H₇ | t-C₄H₉ | m.p. 88.7° C. |
| 361 | 4-F | s-C₄H₉ | i-C₃H₇ | NMR spectrum given hereinafter |
| 362 | 4-F | i-C₃H₇ | s-C₄H₉ | NMR spectrum given hereinafter |

In case of 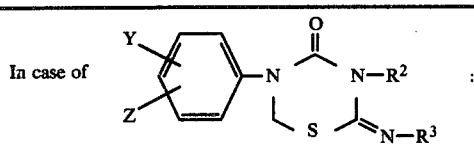

| Compound No. | Y | Z | R² | R³ | Physical property |
|---|---|---|---|---|---|
| 363 | H | 4-NO₂ | i-C₃H₇ | H | m.p. 160°–163° C. |
| 364 | H | 4-NO₂ | i-C₃H₇ | t-C₄H₉ | m.p. 130°–131° C. |

-continued

In case of structure with Y, Z on phenyl ring attached to N, C(=O)–N–R², and S–C=N–R³ in a ring:

| Compound No. | Y | Z | R² | R³ | Physical property |
|---|---|---|---|---|---|
| 365 | H | 4-OH | i-C$_3$H$_7$ | t-C$_4$H$_9$ | m.p. 197°–198° C. |
| 366 | 2-NO$_2$ | 4-NO$_2$ | i-C$_3$H$_7$ | i-C$_3$H$_7$ | m.p. 130°–133° C. |
| 367 | H | 4-C$_2$H$_5$O | i-C$_3$H$_7$ | t-C$_4$H$_9$ | m.p. 79°–80° C. |
| 368 | H | 4-C$_2$H$_5$O | s-C$_4$H$_9$ | t-C$_4$H$_9$ | m.p. 66°–67° C. |
| 369 | H | 4-C$_2$H$_5$O | n-C$_6$H$_{13}$ | i-C$_3$H$_7$ | m.p. 78°–79° C. |
| 370 | H | 4-i-C$_3$H$_7$O | CH$_3$ | i-C$_3$H$_7$ | m.p. 112°–113° C. |
| 371 | H | 4-i-C$_3$H$_7$O | C$_2$H$_5$ | C$_2$H$_5$ | n$_D^{20}$ 1.5649 |
| 372 | H | 4-i-C$_3$H$_7$O | i-C$_3$H$_7$ | i-C$_3$H$_7$ | m.p. 60°–61° C. |
| 373 | H | 4-i-C$_3$H$_7$O | i-C$_3$H$_7$ | t-C$_4$H$_9$ | m.p. 88°–89° C. |
| 374 | H | 4-i-C$_3$H$_7$O | s-C$_4$H$_9$ | t-C$_4$H$_9$ | n$_D^{20}$ 1.5402 |
| 375 | H | 4-i-C$_3$H$_7$O | –CH$_2$–C$_6$H$_5$ | –CH$_2$–C$_6$H$_5$ | m.p. 141°–142° C. |
| 376 | 2-CH$_3$ | 4-CH$_3$ | CH$_3$ | CH$_3$ | n$_D^{20}$ 1.5900 |
| 377 | 2-CH$_3$ | 4-CH$_3$ | CH$_3$ | i-C$_3$H$_7$ | n$_D^{20}$ 1.5674 |
| 378 | 2-CH$_3$ | 4-CH$_3$ | i-C$_3$H$_7$ | i-C$_3$H$_7$ | n$_D^{20}$ 1.5589 |
| 379 | 2-CH$_3$ | 4-CH$_3$ | i-C$_3$H$_7$ | t-C$_4$H$_9$ | m.p. 99°–100° C. |
| 380 | 2-CH$_3$ | 4-CH$_3$ | s-C$_4$H$_9$ | t-C$_4$H$_9$ | n$_D^{20}$ 1.5478 |
| 381 | 2-CH$_3$ | 3-CH$_3$ | CH$_3$ | CH$_3$ | m.p. 78°–79° C. |
| 382 | 2-CH$_3$ | 3-CH$_3$ | C$_2$H$_5$ | –C$_6$H$_{11}$ (cyclohexyl) | m.p. 151°–152° C. |
| 383 | 2-CH$_3$ | 3-CH$_3$ | i-C$_3$H$_7$ | i-C$_3$H$_7$ | m.p. 71°–72° C. |
| 384 | 2-CH$_3$ | 3-CH$_3$ | i-C$_3$H$_7$ | t-C$_4$H$_9$ | m.p. 91°–92° C. |
| 385 | 2-CH$_3$ | 3-CH$_3$ | s-C$_4$H$_9$ | t-C$_4$H$_9$ | n$_D^{20}$ 1.5465 |
| 386 | 2-CH$_3$ | 3-CH$_3$ | –CH$_2$–C$_6$H$_5$ | t-C$_4$H$_9$ | n$_D^{20}$ 1.5769 |
| 387 | 2-CH$_3$ | 4-Cl | i-C$_3$H$_7$ | t-C$_4$H$_9$ | m.p. 122°–123° C. |
| 388 | 2-CH$_3$ | 6-CH$_3$ | i-C$_3$H$_7$ | t-C$_4$H$_9$ | m.p. 103°–104° C. |
| 389 | 2-CH$_3$ | 6-CH$_3$ | CH$_3$ | CH$_3$ | n$_D^{20}$ 1.5967 |
| 390 | 2-CH$_3$ | 6-CH$_3$ | C$_2$H$_5$ | C$_2$H$_5$ | m.p. 77°–78° C. |
| 391 | 2-C$_2$H$_5$ | 6-C$_2$H$_5$ | CH$_3$ | CH$_3$ | m.p. 88°–89° C. |
| 392 | 2-C$_2$H$_5$ | 6-C$_2$H$_5$ | C$_2$H$_5$ | C$_2$H$_5$ | n$_D^{20}$ 1.5644 |
| 393 | 2-C$_2$H$_5$ | 6-C$_2$H$_5$ | CH$_3$ | i-C$_3$H$_7$ | m.p. 106°–107° C. |
| 394 | 2-C$_2$H$_5$ | 6-C$_2$H$_5$ | CH$_2$=CHCH$_2$ | CH$_2$=CHCH$_2$ | n$_D^{20}$ 1.5583 |
| 395 | 2-C$_2$H$_5$ | 6-C$_2$H$_5$ | i-C$_3$H$_7$ | i-C$_3$H$_7$ | m.p. 89°–90° C. |
| 396 | 2-Cl | 4-Cl | CH$_3$ | i-C$_3$H$_7$ | m.p. 109°–111° C. |
| 397 | 2-Cl | 4-Cl | C$_2$H$_5$ | t-C$_4$H$_9$ | m.p. 110°–112° C. |
| 398 | 2-Cl | 4-Cl | i-C$_3$H$_7$ | i-C$_3$H$_7$ | m.p. 121°–123° C. |
| 399 | 2-Cl | 4-Cl | i-C$_3$H$_7$ | t-C$_4$H$_9$ | m.p. 130°–132° C. |
| 400 | 2-Cl | 4-Cl | s-C$_4$H$_9$ | s-C$_4$H$_9$ | n$_D^{25}$ 1.5634 |
| 401 | 2-Cl | 4-Cl | s-C$_4$H$_9$ | t-C$_4$H$_9$ | n$_D^{20}$ 1.5602 |
| 402 | 2-Cl | 3-Cl | i-C$_3$H$_7$ | i-C$_3$H$_7$ | m.p. 93°–94° C. |
| 403 | 3-Cl | 5-Cl | CH$_3$ | CH$_3$ | m.p. 145°–147° C. |
| 404 | 3-Cl | 5-Cl | C$_2$H$_5$ | C$_2$H$_5$ | m.p. 100°–102° C. |
| 405 | 3-Cl | 5-Cl | n-C$_3$H$_7$ | i-C$_3$H$_7$ | m.p. 80°–82° C. |
| 406 | 3-Cl | 5-Cl | i-C$_3$H$_7$ | i-C$_3$H$_7$ | m.p. 81°–83° C. |
| 407 | 3-Cl | 5-Cl | i-C$_3$H$_7$ | t-C$_4$H$_9$ | m.p. 113°–115° C. |
| 408 | 3-Cl | 5-Cl | –CH$_2$–C$_6$H$_5$ | i-C$_3$H$_7$ | m.p. 90°–92° C. |
| 409 | 3-Cl | 5-Cl | i-C$_3$H$_7$ | t-C$_8$H$_{17}$ | m.p. 78°–81° C. |
| 410 | 3-Cl | 5-Cl | n-C$_6$H$_{13}$ | i-C$_3$H$_7$ | n$_D^{23}$ 1.5699 |
| 411 | 3-Cl | 5-Cl | s-C$_4$H$_9$ | s-C$_4$H$_9$ | n$_D^{19}$ 1.5822 |
| 412 | 3-Cl | 5-Cl | CH$_2$=CHCH$_2$ | i-C$_3$H$_7$ | n$_D^{19.5}$ 1.5962 |
| 413 | 3-Cl | 4-Cl | C$_2$H$_5$ | C$_2$H$_5$ | m.p. 86°–88° C. |
| 414 | 3-Cl | 4-Cl | n-C$_3$H$_7$ | n-C$_3$H$_7$ | n$_D^{20}$ 1.5848 |
| 415 | 3-Cl | 4-Cl | i-C$_3$H$_7$ | i-C$_3$H$_7$ | m.p. 104°–107° C. |
| 416 | 3-Cl | 4-Cl | i-C$_3$H$_7$ | t-C$_4$H$_9$ | m.p. 114.5°–117.5° C. |
| 417 | 3-Cl | 4-Cl | n-C$_3$H$_7$ | s-C$_4$H$_9$ | n$_D^{19}$ 1.5772 |
| 418 | 3-Cl | 4-Cl | C$_2$H$_5$ | t-C$_4$H$_9$ | m.p. 105°–107° C. |
| 419 | 3-Cl | 4-Cl | C$_2$H$_5$ | i-C$_4$H$_9$ | n$_D^{19}$ 1.5912 |
| 420 | 3-Cl | 4-Cl | n-C$_3$H$_7$ | i-C$_4$H$_9$ | n$_D^{19}$ 1.5769 |
| 421 | 3-Cl | 4-Cl | CH$_2$=CHCH$_2$ | i-C$_3$H$_7$ | n$_D^{19}$ 1.5920 |
| 422 | 3-Cl | 4-Cl | –CH$_2$–C$_6$H$_5$ | i-C$_3$H$_7$ | n$_D^{19}$ 1.6156 |
| 423 | 3-Cl | 4-Cl | –CH$_2$–C$_6$H$_5$ | –CH$_2$–C$_6$H$_5$ | m.p. 118°–120° C. |
| 424 | 3-Cl | 4-Cl | CH$_3$ | i-C$_3$H$_7$ | m.p. 145°–147° C. |

-continued

In case of:

$$\underset{Z}{\overset{Y}{\diagdown}}\text{—N}\underset{S}{\overset{\text{O}}{\diagup}}\text{N—R}^2, \text{N—R}^3$$

| Compound No. | Y | Z | R² | R³ | Physical property |
|---|---|---|---|---|---|
| 425 | 3-Cl | 4-Cl | i-C₃H₇ | —⟨H⟩ | m.p. 127°–128° C. |
| 426 | 2-Cl | 5-Cl | C₂H₅ | t-C₄H₉ | m.p. 91°–92° C. |
| 427 | 2-Cl | 5-Cl | i-C₃H₇ | t-C₄H₉ | m.p. 145°–146° C. |
| 428 | 2-Cl | 5-Cl | s-C₄H₉ | t-C₄H₉ | m.p. 111°–112° C. |
| 429 | 2-Cl | 5-Cl | —CH₂—⟨⟩ | —CH₂—⟨⟩ | m.p. 119°–120° C. |
| 430 | 2-Cl | 3-Cl | C₂H₅ | t-C₄H₉ | m.p. 144°–145° C. |
| 431 | 3-CH₃ | 4-CH₃ | i-C₃H₇ | i-C₃H₇ | m.p. 66°–67° C. |
| 432 | 3-CH₃ | 4-CH₃ | i-C₃H₇ | t-C₄H₉ | m.p. 109°–110° C. |
| 433 | 3-CH₃ | 4-CH₃ | s-C₄H₉ | t-C₄H₉ | m.p. 92°–93° C. |

The compounds represented by the formula (I) exhibit strong physiological activity against insects, particularly larvae. The larva treated with the compound or ingested the diet treated with the compound dies from abnormal moulting. The insects sensitive to the compound (I) are those of, for example, Hemiptera, Coleoptera, Diptera, Lepidoptera and Orthoptera. Further, many of the compounds (I) have activity to mites; some of them retain miticidal activity to citrus red mite (*Panonychus citri* McGregor) and two-spotted spider mite (*Tetranychus urticae* Koch) even at a concentration of 1,000 ppm, the mortality being 80% or more. Accordingly, the compound of this invention is useful as a physiologically active substance to control the pests by applying to plants, grains and others to protect them from injuries inflicted by the above-noted insects and mites.

For instance, the compound of this invention is useful as an active substance to protect rice, corn an other cereals, vegetables, flowers and ornamental plants, tree, cotton, fruit trees, timbers, harvested grains, grasses, lawns and wood products from the attack of pests. The compound is also useful in controlling the insect pests undesirable for life-environment such as mosquitos and flies. It is particularly useful in controlling paddy field pests such as, for example, brown planthopper (*Nilaparvata lugens* Stal), smaller brown planthopper (*Laodelphax striatellus* Fall'en), white-backed planthopper (*Sogatella furcifera* Horvath), green rice leafhopper (*Nephotettix cincticeps* Uhler) and other plant- and leafhoppers.

Further, as compared with conventional insecticides such as phosphorus compounds and carbamate compounds, the compound of this invention is far lower in mammalian acute toxicity and, hence, is far safer. For example, 2-t-butylimino-3-isopropyl-5-phenyltetrahydro-1,3,5-thiadiazin-4-one (compound No. 145) and 2-t-butylimino-3-isopropyl-5-p-tolyltetrahydro-1,3,5-thiadiazin-4-one (compound No. 318) have LD₅₀ (mice, male) of 10,000 mg/kg or higher. Many other compounds of this invention have LD₅₀ (mice, male) of 5,000 mg/kg or higher. As compared with conventional phosphorus insecticides and carbamate insecticides, the compound of this invention exhibits insecticidal activity at lower concentrations, although the activity value varies with particular target insect. For instance, when the mortality in 7 days after spraying the compound on 5th-instar larvae of brown planthopper is compared, 1-naphthyl N-methylcarbamate (commercial insecticide NAC) showed a mortality of only 30% at 200 ppm concentration, whereas the compound of this invention, for example compound No. 145 or No. 318, showed a mortality of 100% at 100 ppm concentration.

This invention provides also the technique for eradicating or controlling injurious insectes and mites on the basis of physiological activity of the compound of this invention. In one of the embodiments of the invention, the compound is directly applied as such to the objects to be protected or to the pests to be controlled (undiluted spray). For instance, the compound of this invention in the form of liquid of 95% or higher purity can be sprayed from an aeroplane, forming a fog of extremely fine liquid particles. The compound of this invention can also be used in treating ponds and pools inhabited by larvae or treating environmental water or irrigation water grown with a host to render the inhabitation environment or the feed (host) toxic to larvae.

However, as is customary in the art, the compound of this invention is applied, in most of the cases, in the form suitable for use by supporting on or diluted with an inert carrier and, if necessary, admixing with auxiliary agents to eradicate or control injurious insects and mites by the physiological activity of the compound.

General suggestions regarding the formulation of insecticidal compositions based on the compound of this invention are described below.

The compound of this invention is blended with a suitable proportion of a suitable inert carrier and, if necessary, auxiliary agents to allow the compound to dissolve, disperse, suspend, mix, impregnate, adsorb or adhere and formed into a suitable preparation such as, for example, solution, suspension, emulsifiable concentrate, oil spray, wettable powder, dust, granule, tablet, pellet, paste or aerosol.

The inert carrier may be solid, liquid or gas. The materials for the solid carrier include plant powders such as, for example, soybean flour, grain flour, wood flour, bark flour, sawdust, tobacco stalk flour, walnut shell flour, wheat bran, powdered cellulose, and extraction residue of plants; fibrous materials such as paper, corrugated fiberboard, and waste cloth; synthetic polymers such as powdered synthetic resins and polymer granules (for example, urea-formaldehyde polymer); inorganic or mineral substances in the form of powder or granule of a suitable particle size such as clays (for example, kaolin, bentonite and acid clay), talcs (for example, talc and pyrophillite), silicic materials (for example, diatomaceous earth, silica sand, mica, synthetic silicates, finely dispersed synthetic silicic acid, etc.), powdered sulfur, activated carbon, pumice, calcined diatomaceous earth, ground brick, fly ash, sand, calcium carbonate and calcium phosphate; chemical fertilizers such as ammonium sulfate, ammonium phosphate, ammonium nitrate, urea and ammonium chloride; compost, sodium sulfate, sugars and other soluble substances. These solid carriers are used each alone or in mixtures of two or more. Materials for the liquid carrier are selected from not only solvents for the active compound but also nonsolvents which can disperse the active compound in the presence of a suitable auxiliary agent. Such liquid materials are used each alone or in mixtures of two or more. Examples are water, alcohols (for example, methanol, ethanol, butanol and ethylene glycol), ketones (for example, acetone, methyl ethyl ketone, diisobutyl ketone and cyclohexanone), ethers (for example, ethyl ether, dioxane, Cellosolves, dipropyl ether and tetrahydrofuran), aliphatic hydrocarbons (for example, gasoline and mineral oils), aromatic hydrocarbons (for example, benzene, xylene, solvent naphtha, and alkylnaphthalenes), halogenated hydrocarbons (for example, dichloroethane, chlorobenzenes and carbon tetrachloride), esters (for example, ethyl acetate, dibutyl phthalate and dioctyl phthalate), acid amides (for example, diethylformamide, and dimethylformamide), nitriles (for example, acetonitrile) and dimethyl sulfoxide. Gaseous carriers include Freons and other aerosol propellants which are gas under ordinary conditions.

The auxiliary agents include the following materials which are used in accordance with the purpose of use. Combinations of two or more auxiliary agents are frequently used and in some cases no auxiliary agent is used. Surface active agents are used to emulsify, disperse, solubilize and/or wet the active compound. Examples are polyoxyethylene alkylaryl ethers, polyoxyethylene alkyl ethers, polyoxyethylene higher fatty acid esters, polyoxyethylene resin acid esters, polyoxyethylene sorbitan monolaurate, polyoxyethylene sorbitan monooleate, alkylarylsulfonates, naphthalenesulfonic acid condensation products, ligninsulfonate, and higher alcohol sulfate esters. The following substances are used as dispersion stabilizers, spreaders and binders for the active compound: casein, gelatin, starch, alginic acid, methylcellulose, carboxymethylcellulose, gum arabic, polyvinyl alcohol, dry-distilled wood turpentine, rice bran oil, bentonite and ligninsulfonates.

For the purpose of improving the flow property of solid preparations, may be used waxes, stearates and alkyl phosphates. Naphthalenesulfonates and polyphosphates are used as peptizing agents for dispersions. Defoamers such as silicone oil may also be included in the formulation.

The proportion of the active compound in the insecticidal formulation may be varied as required. Suitable proportion of the active compound is generally 0.5 to 20% by weight in dust or granule preparations and 0.1 to 90% by weight in emulsifiable concentrates and wettable powders.

For the purpose of eradicating various insect pests or protecting plants from the attack of various pests, the insecticidal preparation of this invention is used as such or after being suitably diluted with or suspended in water or other media and an effective quantity of the preparation is applied to the plants or environment thereof or to the area inhabited by insect pests. For instance, in order to control the insect pests inhabiting a padding field, the insecticidal preparation of this invention is applied to leaves and stems of rice plant or to the paddy soil or water of the submerged paddy field.

Application rate of the insecticidal preparation of this invention varies depending on various factors such as, for example, the type of target insect, condition and trend of emergence of pests, weather, environmental conditions, form of the insecticidal preparation, mode of application, site being applied, and time of the year. In the case of emulsifiable concentrate and wettable powder, which are applied generally in liquid form, a general practice is to dilute to a final concentration of 0.001% by weight or higher in terms of active ingredient to prepare a spray preparation. Dust and granule are generally applied at a rate of 1 to 10 kg per 10 ares. However, the above-noted application rates do not limit the scope of this invention.

The insecticidal preparation of this invention can be applied, if necessary, in admixture with or jointly with other pesticides, fertilizers, plant nutrients, and plant growth regulators. Examples of insecticides usable in admixture with the insecticide of this invention are:

O,O-dimethyl O-(4-nitro-3-methylphenyl) thiophosphate (Phenitrothion)

O,O-dimethyl O-(3-methyl-4-methylthiophenyl) thiophosphate (Baycid)

O,O-dimethyl S-(carbethoxyphenylmethyl) dithiophosphate (Elsan)

O,O-diethyl O-(2-isopropyl-4-methylpyrimidyl-6) thiophosphate (Diazinon)

O,O-dimethyl 2,2,2-trichloro-1-hydroxyethyl phosphonate (Dipterex)

O-ethyl O-p-cyanophenyl phenylphosphonothioate (Surecide)

O-ethyl O-p-nitrophenyl phenylthiophosphonate (EPN)

O,O-dipropyl O-4-methylthiophenylphosphate (Propaphos)

O,O-dimethyl S-phthalimidomethyl dithiophosphate (Imidan)

O,O-dimethyl O-dichlorovinyl phosphate (DDVP)

O,O-dimethyl S-(N-methylcarbamoylmethyl) dithiophosphate (dimethoate)

O,O-dimethyl S-(1,2-dicarbethoxyethyl) dithiophosphate (malathon)

1-Naphthyl N-methylcarbamate (NAC)

m-Tolyl N-methylcarbamate (MTMC)

2-Isopropoxyphenyl N-methylcarbamate (PHC)

Ethyl N-(diethyl-dithiophosphorylacetyl)-N-methylcarbamate (Mecarbam)

3,4-Xylyl N-methylcarbamate (MPMC)

2-s-Butylphenyl N-methylcarbamate (BPMC)

2-Isopropylphenyl N-methylcarbamate (MIPC)

2-Chlorophenyl N-methylcarbamate (CPMC)

3,5-Xylyl N-methylcarbamate (XMC)

2-(1,3-Dioxolan-2-yl)phenyl N-methylcarbamate (Dioxacarb)

3-t-Butylphenyl N-methylcarbamate (Terbam)

4-Diallylamino-3,5-dimethylphenyl N-methylcarbamate (APC)

S-methyl-N-(methylcarbamoyloxy) thioacetoimidate (Methomil)

N-(2-methyl-4-chlorophenyl)-N,N-dimethylformamidine hydrochloride (chlorphenamidine)

1,3-bis(Carbamoylthio)-2-(N,N-dimethylamino)propane hydrochloride (Cartap)

Diisopropyl-1,3-dithiolan-2-ylidene malonate (Isoprothiolan)

N-[[(4-chlorophenyl)amino]carbonyl]-2,6-difluorobenzamide (Diflubenzuron)

O,O-dimethyl-S-[2-(isopropylthio)ethyl]phosphorodithioate (Isothioate)

O,O-diethyl-S-[2-(ethylthio)ethyl]-phosphorodithioate (Disulfoton)

2,3-dihydro-2,2-dimethylbenzofuran-7-yl N-methylcarbamate (Carbofuran)

EXAMPLE 1

2-Methylimino-3-phenyl-5-isopropyltetrahydro-1,3,5-thiadiazin-4-one (compound No. 66).

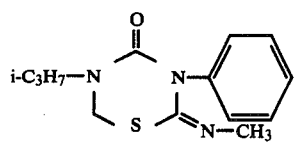

In 50 ml of benzene, were dissolved 3.4 g (0.02 mole) of N-isopropyl-N-chloromethylcarbamoyl chloride and 3.3 g (0.02 mole) of 1-methyl-3-phenylthiourea. The resulting solution was heated under reflux with stirring for 2 hours. After cooling, the precipitated crystals were collected by filtration, washed with benzene and dissolved in 200 ml of water. The resulting aqueous solution was admixed with 20 ml of saturated aqueous sodium carbonate solution and extracted with 100 ml of benzene. The benzene layer was washed with water, dried, and concentrated under reduced pressure to obtain crystals which were recrystallized from isopropyl alcohol. M.p. 174°–176° C.; yield 2.1 g (40%).

NMR(CDCl$_3$)δ; 1.19(d. 6H), 3.00(S. 3H), 4.42(S. 2H), 4.30–4.80(m. 1H), 7.0–7.6(m. 5H)

EXAMPLE 2

2-p-Tolylimino-3-methyl-5-t-butyl-tetrahydro-1,3,5-thiadiazin-4-one (compound No. 72):

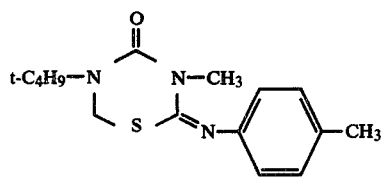

In 50 ml of toluene, were dissolved 3.7 g (0.02 mole) of N-t-butyl-N-chloromethylcarbamoyl chloride and 3.6 g (0.02 mole) of 1-methyl-3-p-tolylthiourea. The resulting solution was heated under reflux for 2 hours. The precipitated crystals were collected by filtration and washed with acetone (m.p. 189°–190° C. decomp.). The crystals were dissolved in 100 ml of water, admixed with 10 ml of a 20% sodium hydroxide solution, and extracted with 50 ml of benzene. The crystals obtained on removal of the benzene under vacuum were recrystallized from isopropyl alcohol. Yield 4.3 g (73%); m.p. 113°–115° C.

NMR(CDCl$_3$)δ: 1.48(S. 9H), 2.30(S. 3H), 3.35(S. 3H), 4.48(S. 2H), 6.65–7.25(m. 4H)

In a similar manner, 2-(2-methyl-4-chloro)-phenylimino-3-methyl-5-isopropyl-tetrahydro-1,3,5-thiadiazin-4-one (compound No. 67):

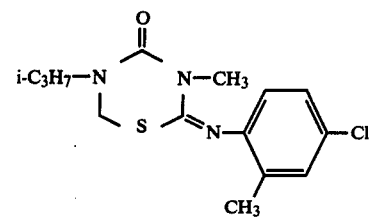

was obtained from 3.4 g of N-isopropyl-N-chloromethylcarbamoyl chloride and 4.2 g of 1-methyl-3-(2-methyl-4-chloro)phenylthiourea. m.p. 91°–92° C.; yield 3.2 g.

NMR(CDCl$_3$)δ: 1.20(d. 6H), 2.10(S. 3H), 3.45(S. 3H), 4.30(S. 2H), 4.45–4.95 (m. 1H), 6.55–7.20(m. 3H)

EXAMPLE 3

2-t-Butylimino-3-phenyl-5-t-butyl-tetrahydro-1,3,5-thiadiazin-4-one (compound No. 77):

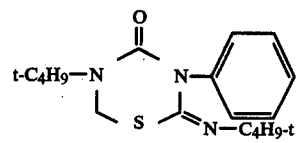

In 50 ml of acetone, were dissolved 3.7 g (0.02 mole) of N-t-butyl-N-chloromethylcarbamoyl chloride and 3.9 g (0.02 mole) of 1-t-butyl-3-phenylthiourea. While stirring, 2.8 g of powdered potassium carbonate was added to the resulting solution and heated under reflux for 2 hours. The reaction mixture was poured into water and extracted with 50 ml of benzene. The benzene layer was washed with water, dried, and concentrated under reduced pressure. The crystals obtained were recrystallized from isopropyl alcohol. Yield 4.1 g (66%); m.p. 133°–134° C.

NMR(CDCl$_3$)δ: 1.10(S. 9H), 1.46(S. 9H), 4.60(S. 2H), 7.0–7.4(m. 5H)

EXAMPLE 4

2-Ethylimino-3-o-tolyl-5-t-butyl-tetrahydro-1,3,5-thiadiazin-4-one (compound No. 80):

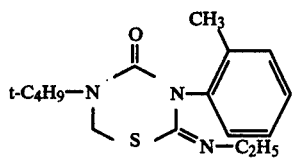

In 50 ml of benzene, were dissolved 3.7 g (0.02 mole) of N-t-butyl-N-chloromethylcarbamoyl chloride and 3.8 g of 1-ethyl-3-O-tolylthiourea. While stirring, 8 g of a 20% sodium hydroxide solution was added to the above solution and stirring was continued for further 4 hours at 30° to 50° C. The reaction mixture was poured into water and extracted with 50 ml of benzene. The benzene layer was washed with water and dried. The crystals obtained on removal of the benzene by distillation were recrystallized from isopropyl alcohol. Yield 3.8 g (63%); m.p. 157°–158° C.

EXAMPLE 5

2-Phenylimino-3-phenyl-5-t-butyl-tetrahydro-1,3,5-thiadiazin-4-one (compound No. 78):

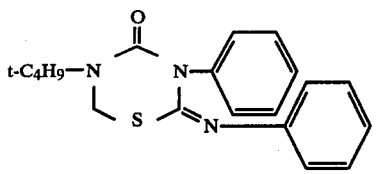

In a mixture of 50 ml of benzene and 10 ml of dimethyl sulfoxide, were dissolved 3.7 g (0.02 mole) of N-t-butyl-N-chloromethylcarbamoyl chloride and 4.6 g of 1,3-diphenylthiourea. While stirring at room temperature, 6.1 g of 1,8-diazabicyclo[5,4,0]-7-undecene was added to the above solution and stirring was continued for further 5 hours. The reaction mixture was poured into water and extracted with benzene. The benzene layer was washed with water and dried. The crystals obtained on removal of the benzene by distillation were recrystallized from isopropyl alcohol. Yield 4.4 g (65%); m.p. 142°–143° C.

EXAMPLE 6

2-Isopropylimino-3-isopropyl-5-methyl-tetrahydro-1,3,5-thiadiazin-4-one (compound No. 1):

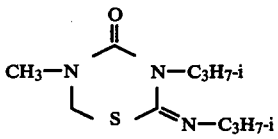

To 2.8 g (0.02 mole) of N-methyl-N-chloromethylcarbamoyl chloride dissolved in 50 ml of benzene, was added 3.2 g (0.02 mole) of 1,3-diisopropylthiourea. The mixture was heated under reflux with stirring for 2 hours. After cooling, 10 g of a 30% potassium hydroxide solution and 50 ml of benzene were added to the mixture and the mixture was shaken thoroughly. The separated benzene layer was washed with water, dried, and the benzene was distilled off under vacuum. The crystals thus obtained were recrystallized from ether. Yield 3.0 g (66%); m.p. 76°–77° C.

NMR(CDCl$_3$)δ: 1.15(d. 6H), 1.40(d. 6H), 3.10(S. 3H) 4.45(S. 2H), 4.50–4.80(m. 1H), 3.30–3.80(m. 1H)

EXAMPLE 7

2-Ethylimino-3,5-diethyl-tetrahydro-1,3,5-thiadiazin-4-one (compound No. 7):

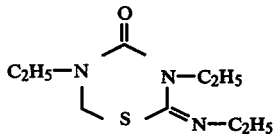

To a mixture of 3.1 g (0.02 mole) of N-ethyl-N-chloromethylcarbamoyl chloride and 2.6 g (0.02 mole) of 1,3-diethylthiourea dissolved in 50 ml of benzene, was added with stirring at room temperature 8 g of a 20% sodium hydroxide solution. After stirring for 5 hours, the reaction mixture was poured into water and extracted with 50 ml of benzene. The benzene layer was washed with water, dried, and the benzene was distilled off under vacuum. The oily substance thus obtained was crystallized from ether. Yield 2.8 g (66%); m.p. 68°–70° C.

NMR(CDCl$_3$)δ; 1.20(t. 9H), 3.20–3.70(m. 4H), 3.75–4.10(q. 2H), 4.40(S. 2H)

EXAMPLE 8

2-Isopropylimino-3-methyl-5-isopropyl-tetrahydro-1,3,5-thiadiazin-4-one (compound No. 18):

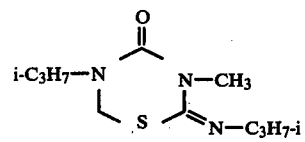

In 50 ml of benzene, were dissolved 3.4 g (0.02 mole) of N-isopropyl-N-chloromethylcarbamoyl chloride and 2.6 g (0.02 mole) of 1-isopropyl-3-methylthiourea. The solution was heated under reflux for 2 hours. After cooling, the precipitated crystals (m.p. 198°–200° C. decomp.) were collected by filtration, washed with a small quantity of acetone, again dissolved in 100 ml of water, admixed with 10 ml of a 30% potassium hydroxide solution, and extracted with 100 ml of benzene. The benzene layer was washed with water, dried, and freed from the benzene by distillation. The crystals thus obtained were recrystallized from ether. Yield 3.8 g (83%).

NMR(CDCl$_3$)δ: 1.10(d. 6H), 1.16(d. 6H), 3.20(S. 3H), 4.33(S. 2H), 4.40–4.85(m. 1H), 3.30–3.70(m. 1H)

EXAMPLE 9

2-Methylimino-3-methyl-5-t-butyl-tetrahydro-1,3,5-thiadiazin-4-one (compound No. 31):

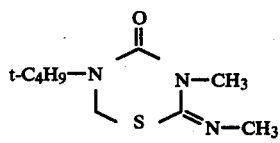

In 50 ml of toluene, were dissolved 3.7 g (0.02 mole) of N-t-butyl-N-chloromethylcarbamoyl chloride and 2.0 g (0.02 mole) of 1,3-dimethylthiourea. The solution was heated under reflux with stirring for one hour. After cooling, the precipitated crystals (m.p. >220° C. decomp.) were collected by filtration, washed with a small quantity of acetone, dissolved again in 100 ml of water, admixed with 10 ml of a 20% sodium hydroxide solution, and extracted with 50 ml of benzene. The benzene layer was dried and concentrated under reduced pressure to obtain 3.5 g (83% yield) of crystals melting at 51°–52° C.

NMR(CDCl$_3$)δ: 1.47(S. 9H), 3.03(S. 3H), 3.14(S. 3H), 4.53(S. 2H)

EXAMPLE 10

2-t-Butylimino-3-benzyl-5-t-butyl-tetrahydro-1,3,5-thiadiazin-4-one (compound No. 47):

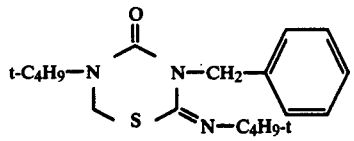

In 50 ml of xylene, were dissolved 3.7 g (0.02 mole) of N-t-butyl-N-chloromethylcarbamoyl chloride and 4.4 g (0.02 mole) of 1-t-butyl-3-benzylthiourea. To the solution, while being stirred at room temperature, was added 8 g of a 30% potassium hydroxide solution. The mixture was stirred for further 4 hours while heating at 30° to 50° C. The reaction mixture was poured into water and extracted with 100 ml of benzene. The benzene layer was washed with water, dried, and the benzene was removed by distillation. The oily substance thus obtained was crystallized from ether. Yield 4.5 g (68%); m.p. 75°–76° C.

EXAMPLE 11

2-Methylimino-3-methyl-5-benzyl-tetrahydro-1,3,5-thiadiazin-4-one (compound No. 54):

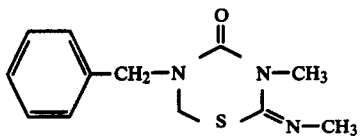

A mixture of 4.4 g (0.02 mole) of N-benzyl-N-chloromethylcarbamoyl chloride and 2.0 g (0.02 mole) of 1,3-dimethylthiourea was dissolved in 50 ml of ethyl alcohol and heated under reflux with stirring for 2 hours. After addition of 20 ml of a saturated aqueous potassium carbonate solution, the mixture was extracted with 100 ml of benzene. The benzene layer was washed with water, dried, and freed from the benzene by distillation under reduced pressure to obtain 4.0 g of crude crystals which were recrystallized from ether. Yield 3.2 g (63%); m.p. 93°–95° C.

EXAMPLE 12

2-t-Butylimino-3-methyl-5-(1,1,3,3-tetramethyl)-butyl-tetrahydro-1,3,5-thiadiazin-4-one (compound No. 63):

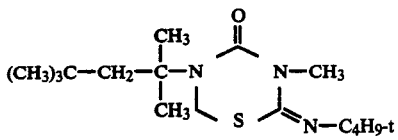

In a mixture of 50 ml of benzene and 10 ml of dimethyl sulfoxide, were dissolved 4.8 g (0.02 mole) of N-(1,1,3,3-tetramethyl)butyl-N-chloromethylcarbamoyl chloride and 2.9 g (0.02 mole) of 1-methyl-3-t-butylthiourea. To the solution, was added with stirring 2.8 g of powdered potassium carbonate and stirring was continued for further 4 hours at 30° to 50° C. The reaction mixture was poured into water and extracted with 50 ml of benzene. The benzene layer was washed with water, dried, and the benzene was removed by distillation under reduced pressure. The oily substance thus obtained was crystallized from ether. Yield 5.1 g (82%); m.p. 91°–93° C.

NMR(CDCl$_3$)δ: 0.97 (S. 9H), 1.20 (S. 9H), 1.50 (S. 6H), 1.90 (S. 2H), 3.18 (S. 3H), 4.54 (S. 2H)

EXAMPLE 13

2-s-Butylimino-3H-5-t-butyl-tetrahydro-1,3,5-thiadiazin-4-one (compound No. 107):

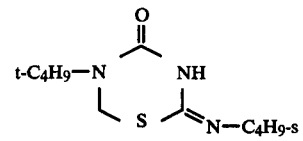

To 1.4 g (0.01 mole) of s-butylthiourea dissolved in 20 ml of acetone, was added 8 g of a 15% potassium hydroxide solution. To the resulting mixture, was added dropwise 1.9 g of N-chloromethyl-N-t-butylcarbamoyl chloride with stirring at room temperature. After stirring for 30 minutes, the reaction mixture was poured into water and extracted with 100 ml of benzene. The benzene layer was dried and concentrated to obtain crude crystals which were recrystallized from ether-isopropyl alcohol. There were obtained 1.6 g (63% yield) of crystals melting at 98°–100° C.

EXAMPLE 14

2-Imino-3H-5-t-butyl-tetrahydro-1,3,5-thiadiazin-4(3H)-one (compound No. 109):

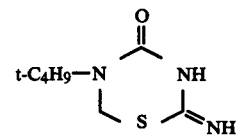

To a suspension of 0.8 g (0.01 mole) of thiourea and 8 g of a 15% potassium hydroxide solution in 50 ml of benzene, was added dropwise 1.9 g (0.01 mole) of N-chloromethyl-N-t-butylcarbamoyl chloride with stirring at room temperature. After stirring for one hour at room temperature, the crystals formed were collected by filtration and recrystallized from chloroform to obtain 0.75 g (41% yield) of crystals melting at 123°–125° C.

EXAMPLE 15

2-Methylimino-3-methyl-5-phenyl-tetrahydro-1,3,5-thiadiazin-4-one (compound No. 115):

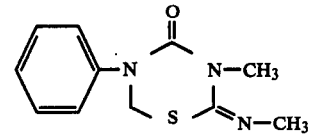

In 50 ml of benzene, were dissolved 2.1 g (0.01 mole) of N-chloromethyl-N-phenylcarbamoyl chloride and 1.0 g (0.01 mole) of 1,3-dimethylthiourea. The resulting solution was heated under reflux with stirring for 3 hours. After cooling, the benzene layer was removed from the reaction mixture by decantation. The residual layer was washed with a small quantity of benzene. The residue (hydrochloride, m.p. 168°–170° C. decomp.) was dissolved in water, admixed with 10 ml of a 10% (W/W) aqueous sodium hydroxide solution and extracted with 100 ml of benzene. The benzene layer was washed with water, dried, and freed from the benzene by distillation under reduced pressure to obtain crude crystals which were recrystallized from isopropyl alcohol. Yield 1.3 g (51%); m.p. 68°–70° C.

NMR(CDCl₃)δ: 3.15 (S. 3H), 3.30 (S. 3H), 4.80 (S. 2H), 7.33 (S. 5H)

EXAMPLE 16

2-Isopropylimino-3-methyl-5-phenyl-tetrahydro-1,3,5-thiadiazin-4-one (compound No. 118):

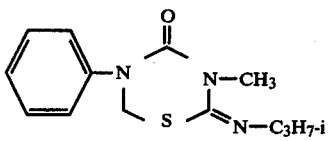

In 50 ml of toluene, were dissolved 2.1 g (0.01 mole) of N-chloromethyl-N-phenylcarbamoyl chloride and 1.3 g (0.01 mole) of 1-isopropyl-3-methylthiourea. To the solution, was added with stirring at room temperature 4 ml of a 20% (W/W) aqueous sodium hydroxide solution and the mixture was stirred for 6 hours. The reaction mixture was poured into water and extracted with 50 ml of benzene. The benzene layer was washed with water, dried and concentrated to obtain crude crystals which were recrystallized from isopropyl alcohol. Yield 1.3 g (50%); m.p. 72°–73.5° C.

NMR(CDCl₃)δ: 1.15 (d. 6H), 3.29 (S. 3H), 3.25–3.85 (m. 1H), 4.73 (S. 2H), 7.28 (S. 5H)

EXAMPLE 17

2-Isopropylimino-3-isopropyl-5-phenyltetrahydro-1,3,5-thiadiazin-4-one (compound No. 144):

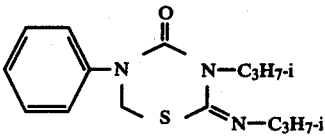

In 50 ml of benzene, were dissolved 2.1 g (0.01 mole) of N-chloromethyl-N-phenylcarbamoyl chloride and 1.6 g (0.01 mole) of 1,3-diisopropylthiourea. The solution was heated under reflux with stirring for 2 hours. The crystals which were formed were collected by filtration. The crystals (hydrochloride, m.p. 188°–190° C. decomp.) were washed with a small quantity of cold acetone, dissolved in water, admixed with 2.8 g of powdered sodium carbonate, and extracted with 100 ml of benzene. The benzene layer was washed with water, dried, and the benzene was removed by distillation to obtain crude crystals which were recrystallized from isopropyl alcohol. Yield 1.8 g (62%); m.p. 92°–94° C.

NMR spectrum (CDCl₃)δ: 1.15 (d. 6H), 1.49 (d. 6H), 3.25–3.68 (m. 1H), 4.82–4.99 (m. 1H), 4.75 (S. 2H), 7.30 (S. 5H).

IR spectrum (KBr): νc=0 1660 cm⁻¹

EXAMPLE 18

2-t-Butylimino-3-isopropyl-5-phenyl-tetrahydro-1,3,5-thiadiazin-4-one (compound No. 145):

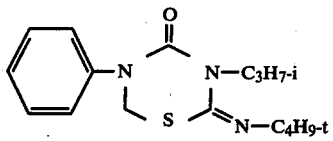

In a mixture of 50 ml of acetone and 10 ml of dimethylformamide, were dissolved 2.1 g (0.01 mole) of N-chloromethyl-N-phenylcarbamoyl chloride and 1.7 g (0.01 mole) of 1-isopropyl-3-t-butylthiourea. To the solution, while stirring at room temperature, was added 4 ml of a 30% (W/W) aqueous potassium hydroxide solution and the mixture was stirred for further 5 hours. The reaction mixture was poured into water and extracted with 100 ml of benzene. The benzene layer was washed with water, dried, and concentrated to obtain a viscous oily substance which was crystallized from isopropyl alcohol. Yield 2.0 g (65%); m.p. 104°–106° C.

NMR(CDCl₃)δ: 1.33 (S. 9H), 1.45 (d. 6H), 4.70 (S. 2H), 4.32–5.00 (m. 1H), 7.30 (S. 5H)

EXAMPLE 19

2-Isopropylimino-3-isobutyl-5-phenyl-tetrahydro-1,3,5-thiadiazin-4-one (compound No. 149):

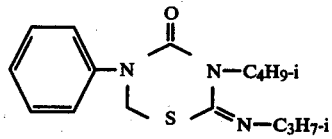

In a mixture of 50 ml of tetrahydrofuran and 10 ml of dimethyl sulfoxide, were dissolved 2.1 g (0.01 mole) of N-chloromethyl-N-phenylcarbamoyl chloride and 1.7 g (0.01 mole) of 1-isopropyl-3-isobutylthiourea. To the solution, while stirring at room temperature, was added 2.1 g of triethylamine and the mixture was stirred for further 6 hours. The reaction mixture was poured into water and extracted with 100 ml of benzene. The benzene layer was washed with water, dried, and concentrated to obtain a viscous oily substance which was crystallized from isopropyl alcohol. Yield 2.4 g (78%); m.p. 80°–82° C.

NMR(CDCl₃)δ: 0.90 (d. 6H), 1.15 (d. 6H), 1.70–2.30 (m. 1H), 3.35–3.75 (m. 1H), 4.05 (d. 2H), 4.75 (S. 2H), 7.30 (S. 5H)

EXAMPLE 20

2-t-Butylimino-3-cyclohexyl-5-phenyl-tetrahydro-1,3,5-thiadiazin-4-one (compound No. 155):

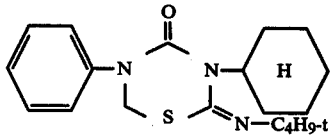

In 50 ml of ether, were dissolved 2.1 g (0.01 mole) of N-chloromethyl-N-phenylcarbamoyl chloride and 2.1 g (0.01 mole) of 1-cyclohexyl-3-t-butylthiourea followed by 1.6 g of pyridine. The resulting solution was stirred for 4 hours at room temperature. The reaction mixture was poured into water and extracted with 100 ml of benzene. The benzene layer was washed with water, dried, and concentrated to obtain an oily substance which was crystallized from isopropyl alcohol. Yield 1.6 g (45%); m.p. 86°–89° C.

NMR(CDCl$_3$)δ: 1.35 (S. 9H), 1.0–2.5 (m. 11H), 4.75 (S. 2H), 7.33 (S. 5H)

EXAMPLE 21

2-Benzylimino-3-methyl-5-phenyl-tetrahydro-1,3,5-thiadiazin-4-one (compound No. 121):

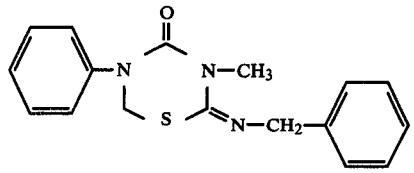

In 20 ml of a 6% (W/W) aqueous potassium hydroxide solution, was suspended 1.8 g (0.01 mole) of 1-methyl-3-benzylthiourea. To the suspension, was added with stirring at room temperature 2.1 g of N-chloromethyl-N-phenylcarbamoyl chloride and the mixture was vigorously stirred for one hour at room temperature. The reaction mixture was poured into water and extracted with 100 ml of benzene. The benzene layer was washed with water, dried, and concentrated to obtain an oily substance which was crystallized from isopropyl alcohol. Yield 2.0 g (63%); m.p. 90°–92° C.

NMR(CDCl$_3$)δ: 3.35 (S. 3H), 4.50 (S. 2H), 4.65 (S. 2H), 7.0–7.5 (m. 10H)

EXAMPLE 22

2-n-Octylimino-3-methyl-5-phenyl-tetrahydro-1,3,5-thiadiazin-4-one (compound No. 122):

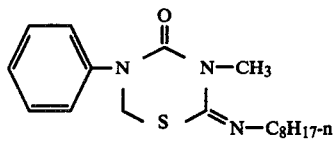

In ethyl alcohol, were dissolved 2.1 g (0.01 mole) of N-chloromethyl-N-phenylcarbamoyl chloride and 2.0 g (0.01 mole) of 1-methyl-3-n-octylthiourea. The solution was heated under reflux with stirring for 3 hours. After cooling, the reaction mixture was poured into water, admixed with 5 ml of a 20% (W/W) aqueous sodium hydroxide solution, and extracted with 100 ml of benzene. The benzene layer was washed with water, dried, and concentrated to obtain a viscous oily substance which was dissolved in 6 N hydrochloric acid and freed from the insoluble matter by extraction with benzene. The aqueous layer was made slightly alkaline by addition of a 20% (W/W) aqueous sodium hydroxide solution and extracted with 50 ml of benzene. The benzene layer was washed with water, dried, and concentrated to obtain a viscous oily substance. Yield 1.2 g (36%); n$_D^{20}$ 1.5551.

EXAMPLE 23

2-s-Butylimino-3,5-diphenyl-tetrahydro-1,3,5-thiadiazin-4-one (compound No. 163):

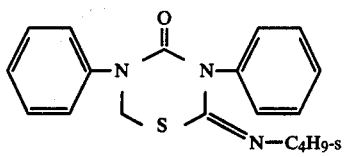

In a mixture of 50 ml of ethyl acetate and 10 ml of dimethyl sulfoxide, were dissolved 2.1 g (0.01 mole) of N-chloromethyl-N-phenylcarbamoyl chloride and 1.9 g (0.01 mole) of 1-s-butyl-3-phenylthiourea. To the solution, was added 1.1 g of powdered sodium carbonate and the mixture was stirred for 3 hours at 50° C. The reaction mixture was poured into water and extracted with 50 ml of ethyl acetate. The ethyl acetate layer was washed with water, dried, and concentrated to obtain crude crystals which were recrystallized from isopropyl alcohol. Yield 1.9 g (57%); m.p. 134°–135.5° C.

NMR(CDCl$_3$)δ: 0.5–1.5 (m. 8H), 3.0–3.5 (m. 1H), 4.85 (S. 2H), 7.25 (S. 10H)

EXAMPLE 24

2-(2-Methyl)phenylimino-3-methyl-5-phenyltetrahydro-1,3,5-thiadiazin-4-one (compound No. 124):

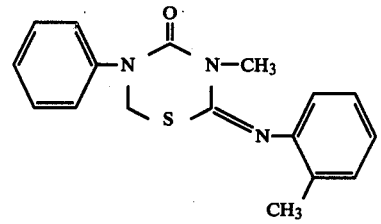

In 50 ml of benzene, were dissolved 2.1 g (0.01 mole) of N-chloromethyl-N-phenylcarbamoyl chloride and 1.8 g (0.01 mole) of 1-methyl-3-o-tolylthiourea. To the solution, while stirring at room temperature, was added 3.1 g of 1,8-diazabicyclo-[5,4,0]-7-undecene and the mixture was stirred for 4 hours. The reaction mixture was poured into water and extracted with 100 ml of benzene. The benzene layer was washed with water, dried, and concentrated to obtain crude crystals which were recrystallized from isopropyl alcohol. Yield 2.0 g (63%); m.p. 113°–114° C.

NMR(CDCl$_3$)δ: 2.18 (S. 3H), 3.50 (S. 3H), 4.68 (S. 2H), 7.0–7.5 (m. 9H).

EXAMPLE 25

2-Methylimino-3-(2-methyl-4-chloro)phenyl-5-phenyl-tetrahydro-1,3,5-thiadiazin-4-one (compound No. 166):

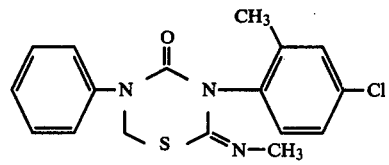

In a mixture of 10 ml of benzene and 10 ml of tetrahydrofuran, were dissolved 1.4 g (1/150 mole) of N-chloromethyl-N-phenylcarbamoyl chloride and 1.4 g (1/150 mole) of 1-methyl-3-(2-methyl-4-chloro)phenylthiourea. To the solution, was added with stirring 5.5 g of a 10% (W/W) aqueous sodium hydroxide solution and the mixture was vigorously stirred for 4 hours, while maintaining the reaction temperature at 40° C. After completion of the reaction, the benzene layer was washed with water and concentrated to obtain an oily mixture of 2-methylimino-3-(2-methyl-4-chloro)phenyl-5-phenyl-tetrahydro-1,3,5-thiadiazin-4-one and 2-(2-methyl-4-chloro)phenylimino-3-methyl-5-phenyltetrahydro-1,3,5-thiadiazin-4-one.

The compound No. 166 could be separated from the above mixture in the following manner.

The above oily mixture was dissolved in 3 N hydrochloric acid and the insoluble matter was removed by washing with ethyl acetate. The aqueous layer was made slightly alkaline to precipitate crystals which were recrystallized from isopropyl alcohol-n-hexane to obtain 1.2 g (52% yield) of the compound No. 166 melting at 121°–123° C.

NMR(CDCl$_3$)δ: 2.18 (S. 3H), 3.07 (S. 3H: =N—CH$_3$), 4.92 (S. 2H).

EXAMPLE 26

2-Methylimino-3-methyl-5-(p-chlorophenyl)tetrahydro-1,3,5-thiadiazin-4-one (compound No. 188):

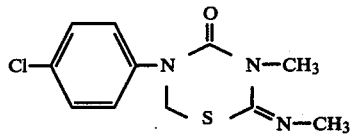

In 50 ml of benzene, were dissolved 2.4 g (0.01 mole) of N-chloromethyl-N-(p-chlorophenyl)carbamoyl chloride and 1.0 g (0.01 mole) of 1,3-dimethylthiourea. The solution was heated under reflux for one hour. The crystals which were formed were collected by filtration and washed with acetone. The resulting white crystals (hydrochloride, m.p. 205° C.) were dissolved in water, admixed with 5 ml of a 20% sodium hydroxide solution, shaken thoroughly, and extracted with benzene. The crystals obtained on removal of the benzene by distillation were recrystallized from isopropyl alcohol to obtain 1.6 g (60% yield) of crystals melting at 98°–100° C.

EXAMPLE 27

2-Isopropylimino-3-methyl-5-(p-chlorophenyl)tetrahydro-1,3,5-thiadiazin-4-one (compound No. 189):

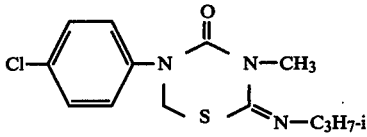

In 50 ml of benzene, were dissolved 2.4 g (0.01 mole) of N-chloromethyl-N-(p-chlorophenyl)carbamoyl chloride and 1.3 g (0.01 mole) of 1-isopropyl-3-methylthiourea. To the solution, was added dropwise with stirring 8 ml of a 10% sodium hydroxide solution and the mixture was further stirred for 4 hours at 40° C. The reaction mixture was poured into water and extracted with benzene. The benzene layer was washed with water, dried, and the benzene was removed by distillation to obtain crystals which were recrystallized from isopropyl alcohol. There were obtained 2.4 g (82% yield) of crystals melting at 106°–108° C.

NMR(CDCl$_3$)δ: 1.18 (d. 6H), 3.32 (S. 3H), 3.55 (m. 1H) 4.80 (S. 2H), 7.25 (S. 4H)

In a manner similar to that described above, 2.3 g (0.01 mole) of i-isopropyl-3-t-octylthiourea and 2.7 g (0.01 mole) of N-chloromethyl-N-m-trifluoromethylphenylcarbamoyl chloride were treated to obtain 2-t-octylimino-3-isopropyl-5-(m-trifluoromethylphenyl)-tetrahydro-1,3,5-thiadiazin-4-one (compound No. 266) as an oily substance:

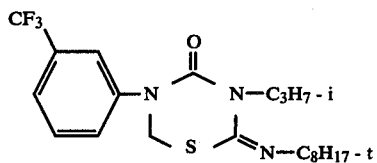

n$_D^{24}$ 1.5089

NMR(CDCl$_3$)δ: 4.70 (s. 2H,

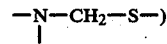

)

EXAMPLE 28

2-t-Butylimino-3-isopropyl-5-(p-chlorophenyl)-tetrahydro-1,3,5-thiadiazin-4-one (compound No. 196):

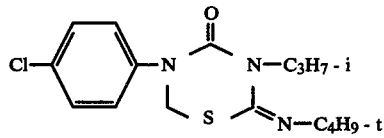

In 50 ml of benzene, were dissolved 2.4 g (0.01 mole) of N-chloromethyl-N-(p-chlorophenyl)-carbamoyl chloride and 1.7 g (0.01 mole) of 1-isopropyl-3-t-butylthiourea. After addition of 8 ml of a 15% potassium hydroxide solution, the mixture was allowed to react by heating at 40° to 50° C. with stirring for 4 hours. The reaction mixture was poured into water and extracted with benzene. The benzene layer was washed with water, dried, and the benzene was removed by distillation to obtain crude crystals which were recrystallized from ethanol. There were obtained 2.0 g (62% yield) of crystals melting at 123°–125° C.

EXAMPLE 29

2-t-Butylimino-3-benzyl-5-(p-chlorophenyl)-tetrahydro-1,3,5-thiadiazin-4-one (compound No. 204):

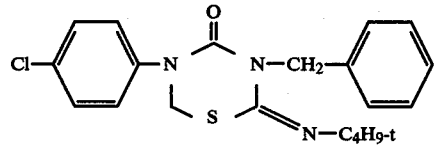

In 50 ml of toluene, were dissolved 2.4 g (0.01 mole) of N-chloromethyl-N-(p-chlorophenyl)-carbamoyl chloride and 2.2 g (0.01 mole) of 1-t-butyl-3-benzylthiourea. After addition of 8 ml of a 10% sodium hydroxide solution, the mixture was allowed to react by heating at 40° to 50° C. with stirring for 4 hours. The reaction mixture was washed with water and the toluene layer was dried and freed from the toluene by distillation to obtain crude crystals which were recrystallized from isopropyl alcohol. There were obtained 2.8 g (73% yield) of crystals melting at 87°–89° C.

EXAMPLE 30

2-t-Butylimino-3-ethyl-5-(m-chlorophenyl)-tetrahydro-1,3,5-thiadiazin-4-one (compound No. 216):

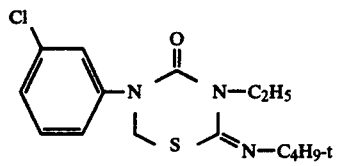

In 50 ml of tetrahydrofuran, were dissolved 2.4 g (0.01 mole) of N-chloromethyl-N-(m-chlorophenyl)-carbamoyl chloride and 1.6 g (0.01 mole) of 1-ethyl-3-t-butylthiourea. After addition of 8 ml of a 15% potassium hydroxide solution, the mixture was allowed to react by heating at 40° to 50° C. with stirring for 4 hours. The reaction mixture was poured into water and extracted with benzene. The benzene layer was dried and concentrated to obtain a viscous oily substance. $n_D^{20}$ 1.5683

NMR(CDCl$_3$)δ: 3.90

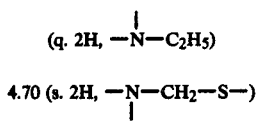

EXAMPLE 31

2-t-Butylimino-3-s-butyl-5-(m-chlorophenyl)-tetrahydro-1,3,5-thiadiazin-4-one (compound No. 225):

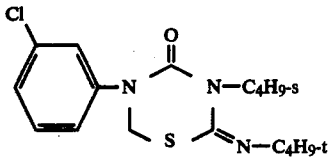

In 50 ml of xylene, were dissolved 2.4 g (0.01 mole) of N-chloromethyl-N-(m-chlorophenyl)-carbamoyl chloride and 1.8 g (0.01 mole) of 1-s-butyl-3-t-butylthiourea. After addition of 8 ml of a 10% sodium hydroxide solution, the mixture was allowed to react by heating at 40°–50° C. with stirring for 4 hours. The reaction mixture was washed with water, dried, and dry gaseous hydrogen chloride was introduced into this xylene solution at room temperature until no more crystals had been precipitated. The crystals were collected by filtration and washed with acetone. The crystals (hydrochloride, m.p. 186° C. decomp.) were suspended in water, admixed with 10 ml of a 15% potassium hydroxide solution, shaken well, and extracted with benzene. The benzene layer was dried and freed from the benzene by distillation to obtain 1.9 g (60% yield) of white crystals melting at 75°–76° C.

EXAMPLE 32

2-Isopropylimino-3-isopropyl-5-(o-chlorophenyl)-tetrahydro-1,3,5-thiadiazin-4-one (compound No. 244):

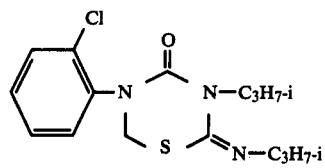

In 50 ml of benzene, were dissolved 2.4 g (0.01 mole) of N-chloromethyl-N-(o-chlorophenyl)-carbamoyl chloride and 1.6 g (0.01 mole) of 1,3-diisopropylthiourea. After addition of 8 ml of a 10% sodium hydroxide solution, the mixture was allowed to react by heating at 50° to 60° C. with stirring for 4 hours. The reaction mixture was washed with water, dried, and freed from the benzene by distillation to obtain crude crystals which were recrystallized from isopropyl alcohol to obtain 1.8 g (56% yield) of crystals melting at 95°–96° C.

NMR(CDCl$_3$)δ: 1.15 (d. 6H), 1.45 (d. 6H), 4.68 (s. 2H), 3.50 (m. 1H), 4.73 (m. 1H), 7.15 (m. 4H)

The above procedure was followed using 1.7 g (0.01 mole) of 1-isopropyl-3-t-butylthiourea to obtain white crystals (m.p. 88°–89° C.) of 2-t-butylimino-3-isopropyl-5-(o-chlorophenyl)-tetrahydro-1,3,5-thiadiazin-4-one (compound No. 245):

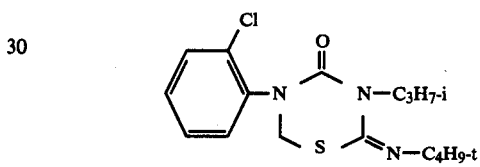

Yield 2.3 g (70%). The crystals were dissolved in benzene and gaseous hydrogen chloride was introduced into the solution. The precipitated crystals were collected by filtration and washed with acetone to obtain crystalline hydrochloride melting at 201° C. (decomp.).

In a similar manner, 1.7 g (0.01 mole) of 1-isopropyl-3-s-butylthiourea and 2.2 g (0.01 mole) of N-chloromethyl-N-(p-fluorophenyl)-carbamoyl chloride were allowed to react to yield crystals melting at 81°–82° C. The crystals gave single spot on a thin-layer chromatogram using a hexane-acetone mixture (8:2) as developing solvent. However, the NMR spectrum revealed that the crystals were approximately 1:1 mixture of the compounds No. 361 and No. 362:

2-Isopropylimino-3-s-butyl-5-(p-fluorophenyl)-tetrahydro-1,3,5-thiadiazin-4-one:

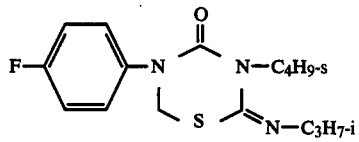

NMR(CDCl$_3$)δ:

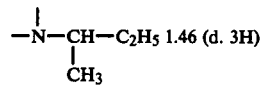

2-s-Butylimino-3-isopropyl-5-(p-fluorophenyl)-tetrahydro-1,3,5-thiadiazin-4-one:

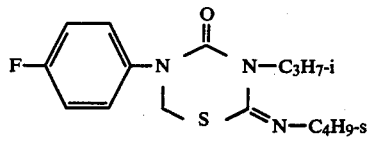

NMR(CDCl₃)δ:

δ: = N—CH—C₂H₅ 1.15 (d. 3H)
          |
          CH₃

EXAMPLE 33

2-Methylimino-3-methyl-5-(p-fluorophenyl)-tetrahydro-1,3,5-thiadiazin-4-one hydrochloride (compound No. 277):

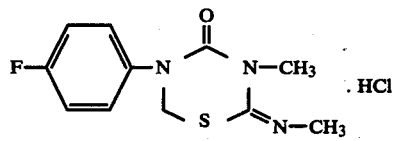

In 50 ml of benzene, were dissolved 1.0 g (0.01 mole) of 1,3-dimethylthiourea and 2.2 g (0.01 mole) of N-chloromethyl-N-(p-fluorophenyl)-carbamoyl chloride. The solution was heated under reflux with stirring for one hour. The oily substance obtained on removal of the benzene by distillation was dissolved in acetone and the precipitated crystals were collected by filtration and washed with acetone to obtain 2.1 g (85% yield) of white crystals of the hydrochloride melting at 221° C. (decomp.). A portion (1 g) of the crystals was dissolved in 20 ml of water, admixed with 5 ml of a 10% sodium hydroxide solution, shaken thoroughly, and extracted with benzene. The benzene layer was dried and concentrated to obtain crystals of free base melting at 105°–106° C.

In a similar manner, 1.7 g (0.01 mole) of 1-isopropyl-3-t-butylthiourea was reacted with 2.2 g (0.01 mole) of N-chloromethyl-N-(p-fluorophenyl)-carbamoyl chloride to obtain 2-t-butylimino-3-isopropyl 5-(p-fluorophenyl)-tetrahydro-1,3,5-thiadiazin-4-one (compound No. 282):

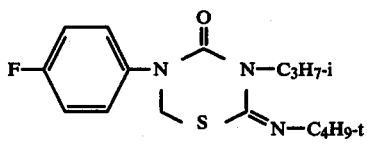

in the form of hydrochloride melting at 160°–195° C. Yield 2.8 g (80%). The crystals were suspended in 20 ml of water and treated in a manner similar to that described above to obtain white crystals of the free base melting at 109°–110° C. (isopropanol). Yield 2.0 g (63%).

EXAMPLE 34

2-Isopropylimino-3-allyl-5-(m-chlorophenyl)-tetrahydro-1,3,5-thiadiazin-4-one (compound No. 217):

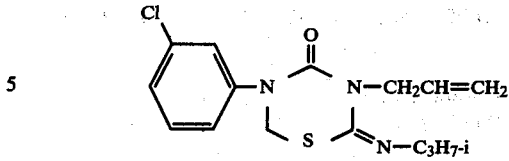

In 50 ml of benzene, were dissolved 2.4 g (0.01 mole) of N-chloromethyl-N-(m-chlorophenyl)-carbamoyl chloride and 1.58 g (0.01 mole) of 1-allyl-3-isopropylthiourea. After addition of 8 ml of a 10% sodium hydroxide solution to the solution, the mixture was allowed to react by heating at 40° to 50° C. with stirring for 4 hours. The reaction mixture was washed with water, dried, and concentrated to obtain a viscous oily substance ($n_D^{19}$ 1.5857) in a yield of 80%.

The above oily substance was dissolved in benzene and gaseous hydrogen chloride was introduced in the solution to obtain hydrochloride melting at 179° C. (decomp.).

EXAMPLE 35

2-t-Butylimino-3-isopropyl-5-(m-chlorophenyl)-tetrahydro-1,3,5-thiadiazin-4-one (compound No. 221):

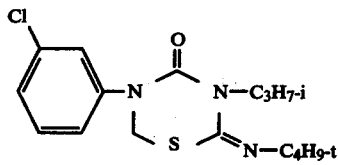

In 50 ml of benzene, were dissolved 2.4 g (0.01 mole) of N-chloromethyl-N-(m-chlorophenyl)-carbamoyl chloride and 1.74 g (0.01 mole) of 1-isopropyl-3-t-butylthiourea. After addition of 8 ml of a 10% sodium hydroxide solution, the mixture was allowed to react by heating at 40° to 50° C. with stirring for 4 hours. The benzene layer was washed with water, dried, and concentrated to obtain a viscous oily substance which was crystallized from isopropyl alcohol to obtain 1.5 g (45% yield) of white crystals having a melting point of 113°–115° C. The crystals were dissolved in benzene and gaseous hydrogen chloride was passed to obtain hydrochloride melting at 152° C. (decomp.).

EXAMPLE 36

2-Cyclohexylimino-3-isopropyl-5-(o-chlorophenyl)-tetrahydro-1,3,5-thiadiazin-4-one (compound No. 252):

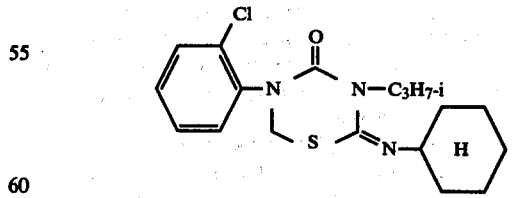

In 50 ml of benzene, were dissolved 2.4 g (0.01 mole) of N-chloromethyl-N-(o-chlorophenyl)-carbamoyl chloride and 2.0 g (0.01 mole) of 1-isopropyl-3-cyclohexylthiourea. After addition of 8 ml of a 10% sodium hydroxide solution, the mixture was allowed to react by heating at 40° to 50° C. with stirring for 4 hours. After completion of the reaction, the benzene layer was washed with water, dried, and concentrated to obtain a viscous oily substance which was crystallized from isopropyl alcohol-n-hexane (1:1) to obtain white crystals melting at 123°–125° C. in a yield of 22.5%.

EXAMPLE 37

2-Ethylimino-3-phenyl-5-(o-chlorophenyl)-tetrahydro-1,3,5-thiadiazin-4-one (compound No. 256):

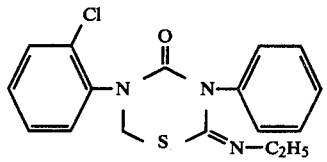

In 50 ml of benzene, were dissolved 2.4 g (0.01 mole) of N-chloromethyl-N-(o-chlorophenyl)-carbamoyl chloride and 1.8 g (0.01 mole) of 1-ethyl-3-phenylthiourea. After addition of 8 ml of a 10% sodium hydroxide solution, the mixture was allowed to react by heating at 40° to 50° C. with stirring for 4 hours. After completion of the reaction, the benzene layer was washed with water, dried, and concentrated to obtain a viscous oily substance which was crystallized from isopropyl alcohol-n-hexane (1:1) to obtain 0.8 g (14% yield) of white crystals melting at 77°–79° C.

EXAMPLE 38

2-Isopropylimino-3-isopropyl-5-(m-trifluoromethylphenyl)-tetrahydro-1,3,5-thiadiazin-4-one (compound No. 265):

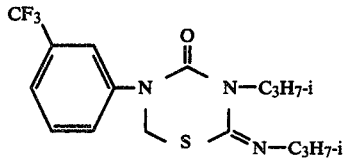

In 50 ml of benzene, were dissolved 2.7 g (0.01 mole) of N-chloromethyl-N-(m-trifluoromethylphenyl)-carbamoyl chloride and 1.6 g (0.01 mole) of 1,3-diisopropylthiourea. After addition of 8 ml of a 10% sodium hydroxide solution, the mixture was allowed to react by heating at 40° to 50° C. with stirring for 4 hours. After completion of the reaction, the benzene layer was washed with water, dried, and concentrated to obtain a viscous oily substance which was crystallized from isopropyl alcohol-n-hexane (1:1) to yield 1.3 g (36% yield) of white crystals melting at 67°–68° C.

EXAMPLE 39

2-t-Butylimino-3-isopropyl-5-(p-tolyl)-tetrahydro-1,3,5-thiadiazin-4-one (compound No. 318):

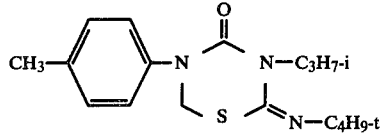

In 10 ml of tetrahydrofuran, was suspended 1.0 g (0.0028 mole) of 1,3,5-tris(p-tolyl)-hexahydro-s-triazine. The resulting suspension was added dropwise with stirring to 5 ml of ice-cooled benzene containing 0.9 g (0.0042 mole) of trichloromethyl chloroformate. After completion of the dropwise addition, the mixture was stirred for one hour at room temperature. To the mixture, was added 20 ml of benzene containing 1.4 g (0.0083 mole) of 1-isopropyl-3-t-butylthiourea. After addition of 7 ml of a 10% sodium hydroxide solution, the mixture was stirred for 4 to 6 hours at 40° to 50° C. The reaction mixture was washed with water, dried, and freed from the benzene by distillation. The crude product thus obtained was recrystallized from isopropyl alcohol to obtain 1.2 g (45% yield) of white crystals melting at 118°–120° C.

NMR(CDCl$_3$)δ: 4.75 (s. 2H), 4.70 (m. 1H), 2.35 (s. 3H), 1.47 (d. 6H), 1.33 (s. 9H)

EXAMPLE 40

2-Benzylimino-3-benzyl-5-(p-tolyl)-tetrahydro-1,3,5-thiadiazin-4-one (compound No. 321):

In 10 ml of tetrahydrofuran, was suspended 1.0 g (0.0028 mole) of 1,3,5-tris(p-tolyl)-hexahydro-s-triazine. The suspension was added dropwise with stirring at room temperature to 5 ml of benzene containing 0.9 g (0.0042 mole) of trichloromethyl chloroformate. Thereafter, the mixture was stirred for one hour at room temperature. To the mixture, was added 2.1 g (0.0083 mole) of 1,3-bis(benzyl)thiourea dissolved in 20 ml of benzene, then followed by 7 ml of a 10% sodium hydroxide solution. The mixture was stirred for 7 hours at room temperature. The reaction mixture was washed with water, dried, and freed from the benzene by distillation to obtain crude crystals which were recrystallized from isopropyl alcohol to yield 1.7 g (51% yield) of white crystals melting at 152°–153° C.

NMR(CDCl$_3$)δ: 7.2 (m. 14H), 5.32 (s. 2H, $$\underset{|}{\overset{|}{N}}-CH_2-),$$

4.78 (s. 2H), 4.50 (s. 2H, =N—CH$_2$—), 2.32 (s. 3H)

EXAMPLE 41

2-Isopropylimino-3-isopropyl-5-(o-tolyl)-tetrahydro-1,3,5-thiadiazin-4-one (compound No. 301):

A solution of 2.4 g (0.0067 mole) of 1,3,5-tris(o-tolyl)-hexahydro-s-triazine in 10 ml of tetrahydrofuran was added dropwise with stirring at room temperature to 10 ml of benzene containing 2.0 g (0.01 mole) of trichloromethyl chloroformate. Thereafter, the mixture was stirred for 30 minutes at 30° C. To the mixture, was added a solution of 3.2 g (0.02 mole) of 1,3-diisopropyl-thiourea in 30 ml of benzene, followed by 16 ml of a 10% sodium hydroxide solution. The mixture was stirred for 4 hours at 40° C., washed with water, dried, and freed from the benzene by distillation. The residual oily substance was admixed with n-hexane and freed from the insoluble matter by filtration. The n-hexane was removed from the filtrate by distillation, leaving behind 3 g (49% yield) of colorless oil substance. $n_D^{20}$ 1.5587

NMR(CDCl$_3$)δ: 4.77 (m. 1H,

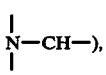

4.52 (s. 2H), 3.48 (m. 1H, =H—CH—), 22.3 (s. 3H), 14.9 (d. 6H), 1.17 (d. 6H)

The above procedure was followed using 1.5 g (0.0042 mole) of 1,3,5-tris(o-tolyl)-hexahydro-s-triazine, 1.3 g (0.0063 mole) of trichloromethyl chloroformate, 3.0 g (0.013 mole) of 1,3-bis(cyclohexyl)-thiourea, and 11 ml of a 10% sodium hydroxide solution to obtain 2.2 g (46% yield) of 2-cyclohexylimino-3-cyclohexyl-5-(o-tolyl)-tetrahydro-1,3,5-thiadiazin-4-one (compound NO. 307) of the formula:

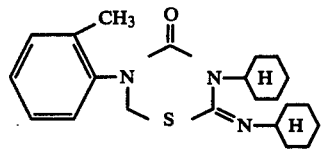

as colorless oily substance ($n_D^{20}$ 1.5568).

In a similar manner, 1.7 g (0.004 mole) of hexahydro-1,3,5-tris(p-ethylphenyl)-s-triazine, 1.3 g (0.006 mole) of trichloromethyl chloroformate, 1.3 g (0.012 mole) of 1,3-dimethylthiourea, and 11 ml of a 10% sodium hydroxide solution were used to obtain 0.8 g (24% yield) of 2-methylimino-3-methyl-5-(p-ethylphenyl)-tetrahydro-1,3,5-thiadiazin-4-one (compound No. 331) of the formula,

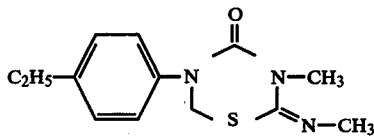

as colorless oily substance ($n_D^{20}$ 1.5992).

Similarly, 1.7 g (0.004 mole) of hexahydro-1,3,5-tris(p-ethylphenyl)-s-triazine, 1.3 g (0.006 mole) of trichloromethyl chloroformate, 2.2 g (0.012 mole) of 1-isopropyl-3-t-butylthiourea, and 11 ml of a 10% sodium hydroxide solution were used to obtain 0.7 g (17% yield) of 2-t-butylimino-3-isopropyl-5-(p-ethylphenyl)-tetrahydro-1,3,5-thiadiazin-4-one (compound No. 133) of the formula,

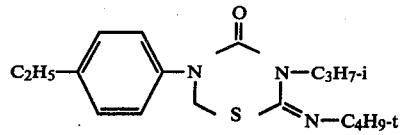

as white crystals (m.p. 70°-72° C.).

Similarly, 2.2 g (0.006 mole) of hexahydro-1,3,5-tris-(o-ethylphenyl)-s-triazine, 1.7 g (0.008 mole) of trichloromethyl chloroformate, 3.1 g (0.0016 mole) of 1-s-butyl-3-butylthiourea, and 15 ml of a 10% sodium hydroxide solution were used to obtain 2.7 g (47% yield) of 2-t-butylimino-3-s-butyl-5-(o-ethylphenyl)-tetrahydro-1,3,5-thiadiazin-4-one (compound No. 339) of the formula,

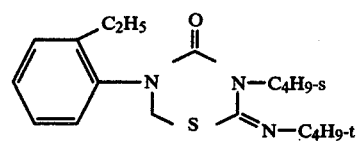

as colorless viscous oily substance ($n_D^{20}$ 1.5401).

EXAMPLE 42

2-t-Butylimino-3-isopropyl-5-(p-methoxyphenyl)tetrahydro-1,3,5-thiadiazin-4-one (compound No. 353):

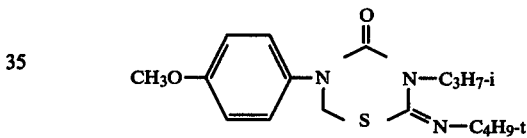

In 20 ml of tetrahydrofuran, was suspended 2.7 g (0.0067 mole) of 1,3,5-tris(p-methoxyphenyl)-hexahydro-s-triazin. The suspension was added dropwise with stirring at room temperature to 10 ml of benzene containing 2.0 g (0.01 mole) of trichloromethyl chloroformate and further stirred for 30 minutes at 30° C. To the mixture, was added a solution of 3.5 g (0.02 mole) of 1-isopropyl-3-t-butylthiourea in 30 ml of benzene, then followed by 16 ml of a 10% sodium hydroxide solution. The mixture was stirred for 4 hours at 40° C., washed with water, dried and freed from the benzene by distillation. The residual oily substance was admixed with n-hexane and freed from the insoluble matter by filtration. The filtrate was freed from the n-hexane by distillation, leaving behind crude crystals which were recrystallized from isopropyl alcohol to yield 3.4 g (51% yield) of white crystals melting at 99°-101.5° C.

NMR(CDCl$_3$)δ: 4.64 (s. 2 H), 4.59 (m. 1 H), 3.75 (s. 3 H), 1.43 (d. 6 H), 1.31 (s. 9 H)

Similarly, 2.7 g (0.0067 mole) of 1,3,5-tris(p-methoxyphenyl)-hexahydro-s-triazine, 2.0 g (0.01 mole) of trichloromethyl chloroformate, 3.8 g (0.02 mole) of 1-s-butyl-3-t-butylthiourea, and 16 ml of a 10% sodium hydroxide solution were used to obtain 1.8 g (26% yield) of 2-t-butylimino-3-s-butyl-5-(p-methoxyphenyl)-tetrahydro-1,3,5-thiadiazin-4-one (compound No. 355) of the formula:

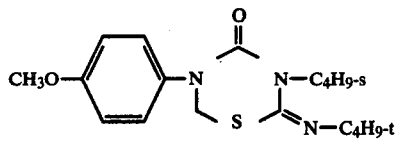

as white crystals melting at 63° C.

NMR(CDCl$_3$)δ: 4.70 (s. 2 H), 4.36 (q. 1 H), 3.75 (s. 3 H), 1.9 (m. 2 H), 1.47 (d. 3 H), 1.32 (s. 9 H), 0.92 (t. 3 H)

Similarly, 1.4 g (0.0033 mole) of 1,3,5-tris(p-methoxyphenyl)-hexahydro-s-triazine, 1 g (0.005 mole) of trichloromethyl chloroformate, 2.1 g (0.01 mole) of 1-isopropyl-3-benzylthiourea, and 9 ml of a 10% sodium hydroxide solution were used to obtain 1.9 g (52% yield) of 2-isopropylimino-3-benzyl-5-(p-methoxyphenyl)tetrahydro-1,3,5-thiadiazin-4-one (compound No. 356) of the formula,

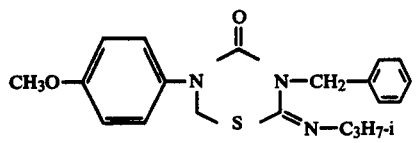

as white crystals melting at 114° C.

NMR(CDCl$_3$): 5.29

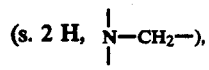

(s. 2 H, N—CH$_2$—), 4.72 (s. 2 H), 3.75 (s. 3 H), 3.52 (m. 1 H), 1.09 (d. 6 H)

EXAMPLE 43

2-t-Butylimino-3-isopropyl-5-(o-isopropyl)-phenyl-tetrahydro-1,3,5-thiadiazin-4-one (compound No. 343):

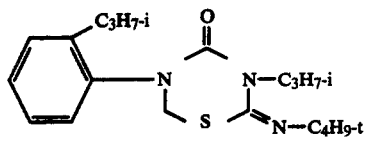

To a solution of 1.4 g (0.003 mole) of 1,3,5-tris(o-isopropyl)phenyl-hexahydro-s-triazine in 20 ml of tetrahydrofuran, was added dropwise with stirring at room temperature 1.0 g of trichloromethyl chloroformate. After 10 minutes of stirring, to the mixture was added a solution of 1.7 g of 1-isopropyl-3-t-butylthiourea in 20 ml of benzene, followed by 8 ml of a 15% potassium hydroxide solution. The mixture was stirred for 3 hours at 40° to 50° C. The reaction mixture was poured into water and extracted with 50 ml of benzene. The benzene layer was dried and freed from the benzene by distillation, leaving behind crude crystals which were recrystallized from isopropyl alcohol to yield 1.7 g (52% yield) of white crystals melting at 108°–109° C.:

EXAMPLE 44

2-Isopropylimino-3-isopropyl-5-(p-bromophenyl)-tetrahydro-1,3,5-thiadiazin-4-one (compound No. 293):

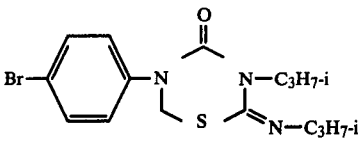

In 50 ml of benzene, were dissolved 2.8 g (0.01 mole) of N-chloromethyl-N-(p-bromophenyl)carbamoyl chloride and 1.6 g of 1,3-diisopropylthiourea. To the solution was added with stirring 4 ml of a 20% sodium hydroxide solution and the mixture was allowed to react at 40° to 50° C. for 4 hours. The reaction mixture was washed with water, dried, and freed from the benzene by distillation to obtain crude crystals which were recrystallized from isopropyl alcohol to yield 1.6 g (45% yield) of white crystals melting at 121°–122° C.

EXAMPLE 45

2-t-Butylimino-3-s-butyl-5-(4-ethoxyphenyl)tetrahydro-1,3,5-thiadiazin-4-one (compound No. 368):

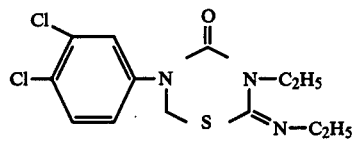

A solution of 1.50 g (0.0033 mole) of hexahydro-1,3,5-tris(4-ethoxyphenyl)-s-triazine in 10 ml of tetrahydrofuran was added dropwise with stirring to 10 ml of benzene containing 1.1 g of phosgene. To the mixture was added 1.88 g of 1-s-butyl-3-t-butylthiourea followed by a 15% potassium hydroxide solution. The mixture was stirred for 4 hours at 40° to 50° C. The reaction mixture was poured into water and extracted with 50 ml of benzene. The benzene layer was washed with water, dried, and concentrated. The crude crystals thus formed was recrystallized from isopropyl alcohol to obtain 1.7 g (46% yield) of white crystals melting at 66°–67° C.

EXAMPLE 46

2-Ethylimino-3-ethyl-5-(3,4-dichlorophenyl)-tetrahydro-1,3,5-thiadiazin-4-one (compound No. 413):

In a conical flask, were placed 2.73 g (0.01 mole) of N-(3,4-dichlorophenyl)-N-chloromethylcarbamoyl chloride, 30 ml of benzene, and 1.32 g (0.01 mole) of 1,3-diethylthiourea to form a homogeneous solution. To the solution, was added 8 ml of a 10% sodium hydroxide solution and the reactant solution was allowed to react with stirring in a water bath at 40° to 50° C. for 4 hours. After completion of the reaction, the benzene layer was washed with water, dried over anhydrous sodium sulfate, and concentrated. The residual oily substance was crystallized from isopropyl alcohol to obtain 1.4 g (43% yield) of white crystals melting at 86°–88° C.

EXAMPLE 47

2-Benzylimino-3-benzyl-5-(3,4-dichlorophenyl)tetrahydro-1,3,5-thiadiazin-4-one (compound No. 423):

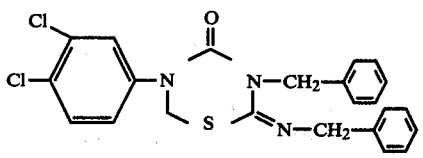

In a reactor, were placed 2.73 g (0.01 mole) of N-(3,4-dichlorophenyl)-N-chloromethylcarbamoyl chloride, 30 ml of benzene, and 2.56 g (0.01 mole) of 1,3-dibenzylthiourea. To the mixture was added tetrahydrofuran to form a homogeneous solution. To the solution was added 8 ml of a 10% aqueous sodium hydroxide solution and the reactant mixture was allowed to react with stirring in a water bath at 40° to 50° C. for 4 hours. After completion of the reaction, the benzene layer was washed with water, dried over anhydrous sodium sulfate, and gaseous hydrogen chloride was introduced in the benzene layer to obtain hydrochloride of the intended compound. The hydrochloride was added to a mixture of 10 ml of a 10% aqueous sodium hydroxide solution and 30 ml of benzene to yield 1.5 g (33% yield) of white crystals of the intended compound in the form of free base melting at 118°–120° C.

EXAMPLE 48

2-t-Butylimino-3-isopropyl-5-(3,4-dichlorophenyl)-tetrahydro-1,3,5-thiadiazin-4-one (compound No. 416):

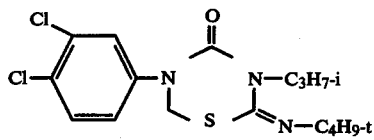

In a reactor, were placed 2.73 g (0.01 mole) of N-(3,4-dichlorophenyl)-N-chloromethylcarbamoyl chloride, 30 ml of benzene, and 1.74 g (0.01 mole) of 1-isopropyl-3-t-butylthiourea. To the mixture was added dropwise 8 ml of a 10% aqueous sodium hydroxide solution. The reactant mixture was allowed to react with stirring in a water bath at 40° to 50° C. for 4 hours. The reaction mixture was treated in a manner similar to that in Example 46 to obtain 0.9 g of white crystals melting at 114.5°–117.5° C.

EXAMPLE 49

2-Isopropylimino-3-benzyl-5-(3,5-dichloro-phenyl)-tetrahydro-1,3,5-thiadiazin-4-one (compound No. 408):

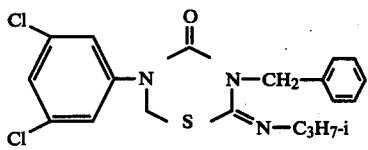

In a reactor, were placed 1.37 g (0.005 mole) of N-(3,5-dichlorophenyl)-N-chloromethylcarbamoyl chloride, 1.04 g (0.005 mole) of 1-benzyl-3-isopropylthiourea, and 20 ml of benzene. After dropwise addition of 4 ml of a 10% aqueous sodium hydroxide solution, the reactant mixture was allowed to react in a water bath at 40° to 50° C. for 2 hours. After completion of the reaction, the benzene layer was washed with water, dried, and gaseous hydrogen chloride was passed through the benzene layer to obtain hydrochloride of the intended compound. The hydrochloride was added to a mixture of 10 ml of a 10% aqueous sodium hydroxide solution and 20 ml of benzene to dissolve the liberated free base in benzene. The benzene layer was concentrated and an oily substance obtained as the residue was crystallized from an isopropyl alcohol-n-hexane (1:1 V/V) mixture to obtain 0.8 g (39% yield) of white crystals melting at 90°–92° C.

EXAMPLE 50

2-Isopropylimino-3-allyl-5-(3,5-dichlorophenyl)-tetrahydro-1,3,5-thiadiazin-4-one (compound No. 412):

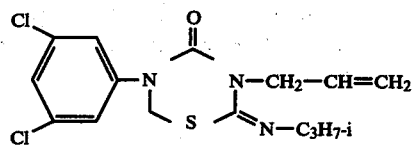

In a reactor, were placed 2.73 g (0.01 mole) of N-(3,5-dichlorophenyl)-N-chloromethylcarbamoyl chloride, 1.58 g of 1-allyl-3-isopropylthiourea, and 30 ml of benzene. To the mixture was added dropwise 8 ml of a 10% aqueous sodium hydroxide solution and the reactant mixture was allowed to react with stirring in a water bath at 40° to 50° C. for 4 hours. After completion of the reaction, the benzene layer was washed with water, dried, and concentrated to leave an oily substance as the residue. The oily substance was purified by silica gel column chromatography to obtain 0.8 g (22.3% yield) of an oil ($n_D^{18.5}$ 1.5962).

EXAMPLE 51

2-t-Butylimino-3-s-butyl-5-(p-ethoxyphenyl)tetrahydro-1,3,5-thiadiazin-4-one (compound No. 368):

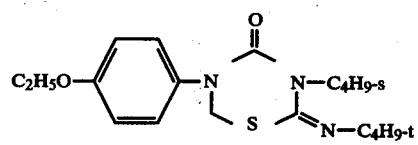

A solution of 2.7 g (0.006 mole) of 1,3,5-tris-(p-ethoxyphenyl)-hexahydro-s-triazine in 10 ml of tetrahydrofuran was added dropwise with stirring at room temperature to 10 ml of benzene containing 1.8 g (0.009 mole) of trichloromethyl chloroformate and the mixture was stirred for further 20 minutes at 40° C. To the mixture was added a suspension of 3.1 g (0.017 mole) of 1-s-butyl-3-t-butylthiourea in 20 ml of benzene, then followed by 15 g of a 10% aqueous sodium hydroxide solution. The reactant mixture was stirred for 3 hours at 40° C. and thereafter the reaction mixture was washed with water, dried, and freed from the benzene by distillation. The residual oily substance was mixed with n-hexane and freed from the insoluble matter by filtration. On removal of the n-hexane from the filtrate by distillation, there were obtained crude crystals which were recrystallized from isopropyl alcohol to yield 3.2 g (53% yield) of white crystals melting at 66°–67° C.

In a similar manner, 2.4 g (0.006 mole) of 1,3,5-tris(2,3-dimethylphenyl)-hexahydro-s-triazine, 1.8 g (0.009 mole) trichloromethyl chloroformate, 3.1 g (0.017 mole) 1-ethyl-3-cyclohexylthiourea, and 15 g of a 10% aqueous sodium hydroxide solution were used to obtain 3.5 g (61% yield) of 2-cyclohexylimino-3-ethyl-5-(2,3-dimethylphenyl)tetrahydro-1,3,5-thiadiazin-4-one (compound No. 382) of the formula,

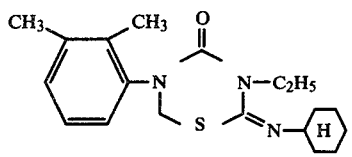

as white crystals melting at 151°–152° C.

Similarly, 2.4 g (0.006 mole) of 1,3,5-tris(2,3-dimethylphenyl)-hexahydro-s-triazine, 1.8 g (0.009 mole) of trichloromethyl chloroformate, 2.9 g (0.017 mole) of 1-isopropyl-3-t-butylthiourea, and 15 g of a 10% aqueous sodium hydroxide solution were used to obtain 2.5 g (45% yield) of 2-t-butylimino-3-isopropyl-5-(2,3-dimethylphenyl)-tetrahydro-1,3,5-thiadiazin-4-one (compound No. 384) of the formula,

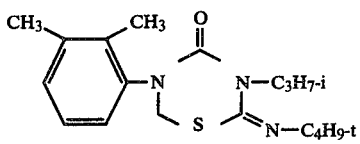

as white crystals melting at 91°–92° C.

Similarly, 1.6 g (0.004 mole) of 1,3,5-tris(2,3-dimethylphenyl)-hexahydro-s-triazine, 1.2 g (0.006 mole) of trichloromethyl chloroformate, 2.7 g (0.012 mole) of 1-benzyl-3-t-butylthiourea, and 11 g of a 10% aqueous sodium hydroxide solution were used to obtain 2.5 g (53% yield) of 2-t-butylimino-3-benzyl-5-(2,3-dimethylphenyl)-tetrahydro-1,3,5-thiadiazin-4-one (compound No. 386) of the formula,

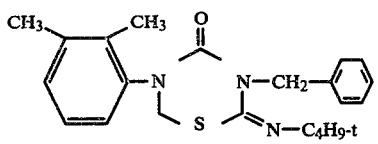

as colorless oily substance ($n_D^{20}$ 1.5769).

EXAMPLE 52

2-Isopropylimino-3-methyl-5-(p-isopropoxyphenyl)-tetrahydro-1,3,5-thiadiazin-4-one (compound No. 370):

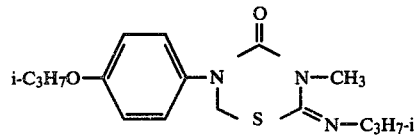

A solution of 2.8 g (0.006 mole) of 1,3,5-tris-(p-isopropoxyphenyl)-hexahydro-s-triazine in 10 ml of tetrahydrofuran was added dropwise at room temperature to 10 ml of benzene containing 1.8 g (0.009 mole) of trichloromethyl chloroformate and the mixture was stirred for 20 minutes at 40° C. To the mixture was added a suspension of 2.2 g (0.017 mole) of 1-methyl-3-isopropylthiourea in 20 ml of benzene, followed by dropwise addition of 15 g of a 10% aqueous sodium hydroxide solution over a period of about one hour. Thereafter, the mixture was stirred for further 2 hours at 50° C. The reaction mixture was washed with water and the remaining benzene layer was intimately mixed with 20 ml of 3N hydrochloric acid to form hydrochloride of the intended compound. The aqueous layer containing the hydrochloride was washed again with fresh benzene, made sufficiently alkaline with an alkali solution, and extracted with benzene. The benzene layer was washed with water, dried, and freed from the benzene by distillation. The residue was recrystallized from isopropyl alcohol to give 1.2 g (23% yield) of white crystals melting at 112°–113° C.

In a similar manner, 2.8 g (0.006 mole) of 1,3,5-tris(p-isopropoxyphenyl)-hexahydro-s-triazine, 1.8 g (0.009 mole) of trichloromethyl chloroformate, 2.6 g (0.016 mole) of 1,3-diisopropylthiourea, and 15 g of a 10% aqueous sodium hydroxide solution were used to obtain 1.4 g (24% yield) of 2-isopropylimino-3-isopropyl-5-(p-isopropoxyphenyl)-tetrahydro-1,3,5-thiadiazin-4-one (compound No. 372) of the formula,

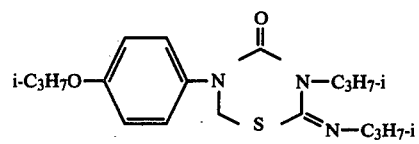

as white crystals melting at 60°–61° C.

Similarly, 2.8 g (0.006 mole) of 1,3,5-tris(p-isopropoxyphenyl)-hexahydro-s-triazine, 1.8 g (0.009 mole) of trichloromethyl chloroformate, 3.0 g (0.016 mole) of 1-s-butyl-3-t-butylthiourea, and 15 g of a 10% aqueous sodium hydroxide solution were used to obtain 1.5 g (25% yield) of 2-t-butylimino-3-s-butyl-5-(p-isopropoxyphenyl)-tetrahydro-1,3,5-thiadiazin-4-one (compound No. 374) of the formula,

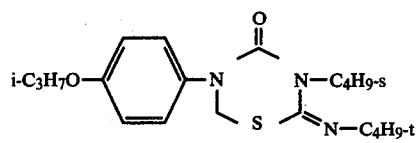

as colorless oily substance ($n_D^{20}$ 1.5402).

Similarly, 2.0 g (0.004 mole) of 1,3,5-tris(p-isopropoxyphenyl)-hexahydro-s-triazine, 1.2 g (0.006 mole) of trichloromethyl chloroformate, 3.1 g (0.012 mole) of 1,3-dibenzylthiourea, and 11 g of a 10% aqueous sodium hydroxide solution were used to obtain 1.5 g (28% yield) of 2-benzylimino-3-benzyl-5-(p-isopropoxyphenyl)-tetrahydro-1,3,5-thiadiazin-4-one (compound No. 375) of the formula,

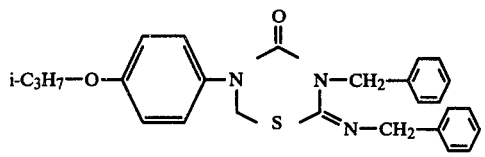

as white crystals melting at 141°–142° C.

EXAMPLE 53

2-Isopropylimino-3-methyl-5-(2,4-dimethyl-phenyl)-tetrahydro-1,3,5-thiadiazin-4-one (compound No. 377):

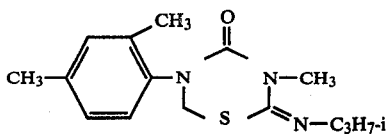

In a manner similar to that in Example 51, the reaction was carried out by using 2.4 g (0.006 mole) of 1,3,5-tris(2,4-dimethylphenyl)-hexahydro-s-triazine, 1.8 g (0.009 mole) of trichloromethyl chloroformate, 2.1 g (0.016 mole) of 1-methyl-3-isopropylthiourea, and 15 g of a 10% aqueous sodium hydroxide solution. After completion of the reaction, the n-hexane-insoluble matter was removed by filtration and the filtrate was freed from the n-hexane by distillation. The residue was dissolved in ether and gaseous hydrogen chloride was passed through the ether solution. An ether-insoluble oily substance immediately separated out and deposited on the bottom. After removal of the solvent, an excess amount of aqueous alkali solution was added to the oily substance and extracted with benzene. The benzene layer was washed with water, dehydrated, and concentrated to give 0.9 g (19% yield) of a colorless oily substance ($n_D^{20}$ 1.5674).

In a similar manner, 2.4 g (0.006 mole) of 1,3,5-tris(2,4-dimethylphenyl)-hexahydro-s-triazine, 1.8 g (0.009 mole) of trichloromethyl chloroformate, 2.5 g (0.0016 mole) of 1,3-diisopropylthiourea, and 15 g of a 10% aqueous sodium hydroxide solution were used to obtain 1.2 g (22% yield) of 2-isopropylimino-3-isopropyl-5-(2,4-dimethylphenyl)-tetrahydro-1,3,5-thiadiazin-4-one (compound No. 378) of the formula,

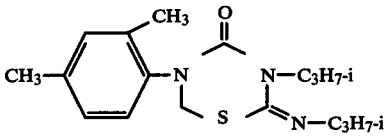

as a light yellow oily substance ($n_D^{20}$ 1.5589).

Similarly, 2.4 g (0.006 mole) of 1,3,5-tris(2,4-dimethylphenyl)-hexahydro-s-triazine, 1.8 g (0.009 mole) of trichloromethyl chloroformate, 2.9 g (0.016 mole) of 1-isopropyl-3-t-butylthiourea, and 15 g of a 10% aqueous sodium hydroxide solution were used to obtain 1.0 g (18% yield) of 2-t-butylimino-3-isopropyl-5-(2,4-dimethylphenyl)-tetrahydro-1,3,5-thiadiazin-4-one (compound No. 379):

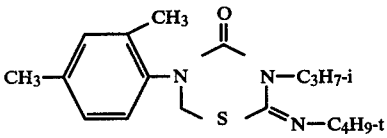

as white crystals melting at 99°–100° C.

In a similar manner, 3.3 g (0.007 mole) of 1,3,5-tris(2-methyl-4-chlorophenyl)-hexahydro-s-triazine, 2.0 g (0.01 mole) of trichloromethyl chloroformate, 3.2 g (0.018 mole) of 1-isopropyl-3-t-butylthiourea, and 18 g of a 10% aqueous sodium hydroxide solution were used to obtain 0.5 g (7% yield) of 2-t-butylimino-3-isopropyl-5-(2-methyl-4-chlorophenyl)-tetrahydro-1,3,5-thiadiazin-4-one (compound No. 387) of the formula,

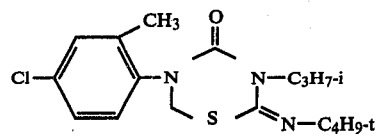

as white crystals melting at 122°–123° C.

Similarly, 2.7 g (0.02 mole) of N-methylene-2,6-dimethylaniline, 2.0 g of trichloromethyl chloroformate, 2.0 g (0.02 mole) of 1,3-dimethylthiourea, and 18 g of a 10% aqueous sodium hydroxide solution were used to obtain 0.6 g (12% yield) of 2-methylimino-3-methyl-5-(2,6-dimethylphenyl)-tetrahydro-1,3,5-thiadiazin-4-one (compound No. 389) of the formula,

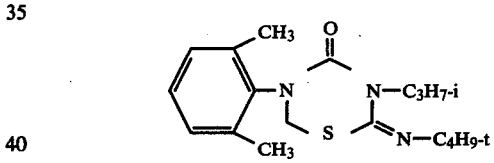

as a colorless oily substance ($n_D^{20}$ 1.5967).

Similarly, 2.7 g (0.02 mole) of N-methylene-2,6-dimethylaniline, 2.0 g (0.01 mole) of trichloromethyl chloroformate, 3.3 g (0.019 mole) of 1-isopropyl-3-t-butylthiourea, and 18 g of a 10% aqueous sodium hydroxide solution were used to obtain 0.3 g (7% yield) of 2-t-butylimino-3-isopropyl-5-(2,6-dimethylphenyl)tetrahydro-1,3,5-thiadiazin-4-one (compound No. 388) of the formula,

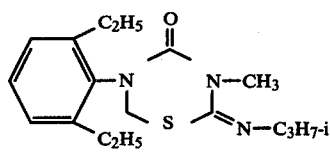

as white crystals melting at 103°–104° C.

EXAMPLE 54

2-Isopropylimino-3-methyl-5-(2,6-diethylphenyl)tetrahydro-1,3,5-thiadiazin-4-one (compound No. 393):

A solution of 1.6 g (0.01 mole) of N-methylene-2,6-diethylaniline in 20 ml of benzene was added dropwise with stirring to 10 ml of a toluene solution containing 1.2 g of phosgene. After 10 minutes of stirring, 1.3 g (0.01 mole) of 1-methyl-3-isopropylthiourea was added to the mixture and heated under reflux for one hour. The reaction mixture was admixed with 100 ml of water and the benzene layer was removed. The aqueous layer was made alkaline with 5 ml of a 30% potassium hydroxide solution and extracted with 100 ml of benzene. The benzene layer was washed with water, dried, and concentrated to obtain a viscous oily substance. The oily substance was recrystallized from isopropyl alcohol to give 1.7 g (56% yield) of white crystals melting at 106°–107° C.

EXAMPLE 55

2-Isopropylimino-3-isopropyl-5-(2,6-diethylphenyl)-tetrahydro-1,3,5-thiadiazin-4-one (compound No. 395):

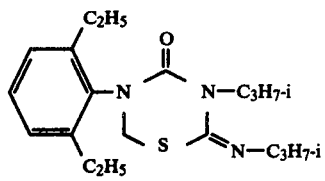

A solution of 1.6 g (0.01 mole) of N-methylene-2,6-diethylaniline in 10 ml of benzene was added with stirring to 10 ml of benzene containing 1.1 g of trichloromethyl chloroformate. After 10 minutes of stirring, a solution of 1.6 g (0.01 mole) of 1,3-diisopropylthiourea in 20 ml of benzene was added to the mixture and heated under reflux with stirring for one hour. The reaction mixture was admixed with 100 ml of water and shaken thoroughly. The aqueous layer was separated and mixed with 5 ml of a 30% aqueous potassium hydroxide solution to deposit an oily substance which was extracted with benzene. The benzene layer was washed with water, dried, and concentrated to a viscous oily substance which was recrystallized from isopropanol-n-hexane (8:2) to give 1.4 g (40% yield) of white crystals melting at 89°–90° C.

NMR(CDCl$_3$)δ: 3.50

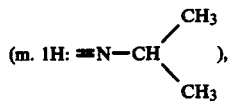

(m. 1H: =N—CH ), 4.50 (s. 2H:

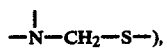

4.84 (m. 1H:

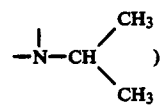

EXAMPLE 56

2-t-Butylimino-3-ethyl-5-phenyl-tetrahydro-1,3,5-thiadiazin-4-one (compound No. 131):

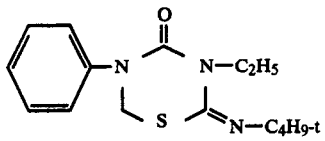

A solution of 46 g of aniline in 250 ml of ethyl alcohol was mixed with 75 ml of 37% formalin and stirred for 30 minutes at room temperature. The precipitated crystals were collected by filtration, washed with ethyl alcohol and recrystallized from hot benzene to obtain 1,3,5-triphenyl-hexahydro-s-triazine melting at 130°–133° C. To a solution of 1.2 g of trichloromethyl chloroformate in 10 ml of benzene, was added dropwise with stirring a solution of 1.0 g (0.0033 mole) of the above 1,3,5-triphenyl-hexahydro-s-triazine in 20 ml of tetrahydrofuran, followed by a solution of 1.6 g of 1-ethyl-3-t-butylthiourea in 20 ml of benzene and then by 8 ml of a 15% aqueous potassium hydroxide solution. The reactant mixture was heated to 40° to 50° C. and stirred for 5 hours. The reaction mixture was poured into water and the separated benzene layer was washed with water and dried. The crude crystals obtained on removal of the benzene by distillation were recrystallized from isopropyl alcohol to give 1.0 g (38% yield) of white crystals melting at 93°–94° C.

In a similar manner, 1.0 g of 1,3,5-triphenylhexahydro-s-triazine, 1.1 g of trichloromethyl chloroformate, and 1.7 g of 1-isopropyl-3-t-butylthiourea were reacted to yield 1.2 g (40% yield) of 2-t-butylimino-3-isopropyl-5-phenyl-tetrahydro-1,3,5-thiadiazin-4-one (compound No. 145) of the formula,

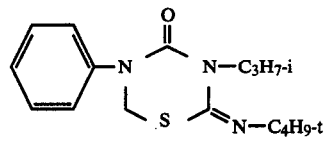

in the form of white crystals melting at 106°–107° C.

The compound of this invention is blended with auxiliary agents into various compositions according to the following formulations. The type and proportion of the compound and auxiliary agents as well as the form of the composition may be varied as required. The technique of blending and the technique of applying the composition are similar to those known in the art. In the following Examples all parts are by weight.

EXAMPLE 57

An emulsifiable concentrate was prepared by uniformly blending the following ingredients:

|  | Parts |
| --- | --- |
| Compound No. 131 | 50 |
| Xylene | 40 |
| Mixture of polyoxyethylene nonylphenyl ether and calcium alkylbenzenesulfonate | 10 |

EXAMPLE 58

A dust composition was prepared by uniformly blending the following ingredients:

|  | Parts |
| --- | --- |
| Compound No. 144 | 3 |
| Powdered clay | 82 |
| Powdered diatomaceous earth | 15 |

EXAMPLE 59

A granule composition was prepared by uniformly blending the following ingredients, then kneading thoroughly with a suitable quantity of water, granulating, and drying.

| | Parts |
|---|---|
| Compound No. 145 | 5 |
| Mixture of powdered bentonite and clay | 90 |
| Calcium ligninsulfonate | 5 |

EXAMPLE 60

A wettable powder was prepared by uniformly mixing the following ingredients:

| | Parts |
|---|---|
| Compound No. 144 | 20 |
| Mixture of powdered clay and synthetic high-dispersion silicic acid | 75 |
| Mixture of polyoxyethylene nonylphenyl ether and calcium alkylbenzenesulfonate | 5 |

EXAMPLE 61

An oil spray composition was prepared by mixing the following ingredients:

| | Parts |
|---|---|
| Compound No. 115 | 2 |
| Kerosene | 98 |

EXAMPLE 62

A granule composition was prepared by dissolving the following ingredients in a suitable solvent and spraying over 95 parts of granular clay (10–48 mesh Tyler standard sieve in granule size) and drying.

| | Parts |
|---|---|
| Compound No. 62 | 3 |
| 0,0-diethyl 0-(2-isopropyl-4-methylpyrimidyl-6)thiophosphonate | 2 |

EXAMPLE 63

An emulsifiable concentrate was prepared by uniformly mixing the following ingredients:

| | Parts |
|---|---|
| Compound No. 18 | 50 |
| Xylene | 40 |
| Mixture of polyoxyethylene nonylphenyl ether and calcium alkylbenzenesulfonate | 10 |

EXAMPLE 64

A dust composition was prepared by uniformly blending the following ingredients:

| | Parts |
|---|---|
| Compound No. 25 | 3 |
| Powdered clay | 82 |
| Powdered diatomaceous earth | 15 |

EXAMPLE 65

A granule composition was prepared by uniformly mixing the following ingredients, kneading thoroughly with a suitable quantity of water, granulating, and drying.

| | Parts |
|---|---|
| Compound No. 42 | 5 |
| Mixture of powdered bentonite and powdered clay | 90 |
| Calcium ligninsulfonate | 5 |

EXAMPLE 66

A wettable powder was prepared by uniformly mixing the following ingredients:

| | Parts |
|---|---|
| Compound No. 48 | 20 |
| Mixture of powdered kaolin and synthetic fine-dispersion silicic acid | 75 |
| Mixture of polyoxyethylene nonylphenyl ether and calcium alkylbenzenesulfonate | 5 |

EXAMPLE 67

An oil spray composition was prepared by mixing the following ingredients:

| | Parts |
|---|---|
| Compound No. 66 | 2 |
| Kerosene | 98 |

EXAMPLE 68

A solution of 3 parts of the compound No. 87 in a suitable solvent was sprayed over 97 parts of granular clay (10–48 mesh Tyler standard sieve in particle size) and dried to give a granule composition.

EXAMPLE 69

An emulsifiable concentrate was prepared by uniformly mixing the following ingredients:

| | Parts |
|---|---|
| A compound of this invention | 50 |
| Xylene | 40 |
| Polyoxyethylene nonylphenyl ether admixed with calcium alkylbenzenesulfonate | 10 |

EXAMPLE 70

A dust composition was prepared by uniformly mixing the following ingredients:

| | Parts |
|---|---|
| Compound No. 318 | 3 |
| Powdered clay | 82 |
| Powdered diatomaceous earth | 15 |

EXAMPLE 71

A granule composition was prepared by uniformly mixing the following ingredients, kneading sufficiently with a suitable quantity of water, granulating, and drying.

|  | Parts |
|---|---|
| Compound No. 195 | 5 |
| Powdered mixture of bentonite and clay | 90 |
| Calcium ligninsulfonate | 5 |

EXAMPLE 72

A wettable powder was prepared by uniformly mixing the following ingredients:

|  | Parts |
|---|---|
| Compound No. 241 | 20 |
| Powdered mixture of kaolin and synthetic high-dispersion silicic acid | 75 |
| Mixture of polyoxyethylene nonylphenyl ether and calcium alkylbenzenesulfonate | 5 |

EXAMPLE 73

An oil spray composition was prepared by mixing the following ingredients:

|  | Parts |
|---|---|
| Compound No. 302 | 2 |
| Kerosene | 98 |

EXAMPLE 74

A granule composition was prepared by dissolving the following ingredients in a suitable solvent and spraying over 95 parts of granular clay (10–48 mesh Tyler standard sieve in particle size) and drying.

|  | Parts |
|---|---|
| Compound No. 316 | 3 |
| O,O-diethyl O-(2-isopropyl-4-methylpyrimidyl-6) thiophosphate | 2 |

TEST EXAMPLE 1

Insecticidal activity against larvae of brown planthopper (*Nilaparvata lugens* Stahl).

Testing method: Five rice seedlings of the 1.5 leaf age were dipped in a test composition of 400 ppm concentration for 30 seconds. After air-drying, the seedlings were placed in a glass tube containing 1 ml of water and infested with five third-instar larvae of brown planthopper. The glass tube was left standing in a constant temperature cabinet at 25° C. and 5 or 7 days after the treatment, dead-and-survival was observed. Mortality was calculated from the results of 3-replication test.

The results obtained were as shown in Table 1.

Table 1*

| Compound No. | Mortality (%) | Compound No. | Mortality (%) | Compound No. | Mortality (%) |
|---|---|---|---|---|---|
| 2 | 100 | 53 | 80 | 131 | 100 |
| 6 | 100 | 56 | 80 | 134 | 100 |
| 8 | 100 | 59 | 100 | 135 | 100 |
| 9 | 100 | 63 | 100 | 136 | 80 |
| 10 | 100 | 65 | 100 | 137 | 80 |
| 14 | 80 | 66 | 100 | 139 | 100 |
| 16 | 100 | 68 | 100 | 140 | 100 |
| 18 | 100 | 69 | 100 | 141 | 100 |
| 23 | 100 | 71 | 80 | 142 | 100 |
| 25 | 100 | 72 | 80 | 147 | 100 |
| 27 | 100 | 75 | 100 | 148 | 100 |
| 29 | 100 | 80 | 100 | 149 | 100 |
| 31 | 80 | 82 | 100 | 150 | 100 |
| 32 | 100 | 83 | 100 | 151 | 100 |
| 33 | 100 | 87 | 100 | 152 | 100 |
| 35 | 100 | 88 | 100 | (155 | 50) |
| 37 | 100 | 123 | 100 | 156 | 100 |
| 42 | 100 | 126 | 100 | 157 | 100 |
| 48 | 100 | 127 | 100 | 159 | 80 |
| 51 | 100 | 129 | 80 | 162 | 100 |
| 167 | 70 | 241 | 100 | 293 | 100 |
| 179 | 90 | 242 | 100 | 294 | 100 |
| 182 | 70 | 243 | 100 | 295 | 100 |
| 188 | 100 | 244 | 100 | 297 | 100 |
| 194 | 100 | 245 | 100 | 299 | 100 |
| 196 | 100 | 247 | 90 | 300 | 100 |
| 197 | 100 | 248 | 100 | 301 | 100 |
| 198 | 100 | 249 | 100 | 302 | 100 |
| 213 | 100 | 252 | 100 | 303 | 100 |
| 216 | 100 | 253 | 80 | 304 | 100 |
| 217 | 100 | 255 | 100 | 305 | 95 |
| 218 | 100 | 258 | 100 | 307 | 70 |
| 219 | 100 | 259 | 60 | 308 | 60 |
| 220 | 100 | 260 | 60 | 312 | 100 |
| 221 | 100 | 269 | 80 | 314 | 100 |
| 222 | 100 | 270 | 60 | 315 | 100 |
| 223 | 100 | 274 | 100 | 316 | 100 |
| 224 | 100 | 275 | 100 | 317 | 100 |
| 225 | 100 | 276 | 100 | 318 | 100 |
| 228 | 100 | 280 | 100 | 319 | 100 |
| 229 | 100 | 282 | 100 | 320 | 100 |
| 232 | 70 | 283 | 100 | 321 | 85 |
| 233 | 100 | 284 | 100 | 324 | 100 |
| 234 | 100 | 285 | 100 | 325 | 100 |
| 236 | 80 | 289 | 100 | 326 | 100 |
| 237 | 100 | 291 | 100 | 327 | 100 |
| 328 | 90 | 377 | 100 | 418 | 60 |
| 332 | 100 | 378 | 100 | 421 | 60 |
| 333 | 100 | 379 | 100 | 422 | 60 |
| 334 | 100 | 380 | 100 | 425 | 60 |
| 335 | 80 | 381 | 60 | 426 | 70 |
| 336 | 100 | 382 | 80 | 427 | 100 |
| 337 | 100 | 383 | 100 | 428 | 100 |
| 338 | 100 | 384 | 100 |  |  |
| 339 | 100 | 385 | 100 |  |  |
| 342 | 100 | 387 | 100 |  |  |
| 343 | 100 | 388 | 100 |  |  |
| 344 | 100 | 390 | 60 |  |  |
| 350 | 100 | 394 | 70 |  |  |
| 352 | 100 | 395 | 100 |  |  |
| 353 | 100 | 398 | 100 |  |  |
| 354 | 100 | 399 | 100 |  |  |
| 355 | 100 | 400 | 100 |  |  |
| 360 | 100 | 401 | 100 |  |  |
| 364 | 100 | 402 | 80 |  |  |
| 367 | 80 | 406 | 80 |  |  |
| 368 | 80 | 407 | 100 |  |  |
| 371 | 75 | 409 | 60 |  |  |
| 372 | 60 | 411 | 60 |  |  |
| 373 | 80 | 412 | 100 |  |  |
| 374 | 80 | 415 | 100 |  |  |
| 376 | 60 | 416 | 100 |  |  |

*Compound No. 2–No. 88: Data of 7 days after treatment
Compound No. 126–No. 428: Data of 5 days after treatment

TEST EXAMPLE 2

Insecticidal activity against larvae of white-backed planthopper (*Sogatella furcifera* Horvath).

Testing method: Five rice seedlings of the 1.5 leaf age were dipped in a test composition of 400 ppm concentration for 30 seconds. After air-drying, the seedlings were placed in a glass tube containing 1 ml of water and infested with five first-instar larvae of white-backed planthopper. The glass tube was left standing in a constant temperature cabinet at 25° C. and seven days after the treatment, dead-and-survival was observed. Mortality was calculated from the results of 3-replication test.

The results obtained were as shown in Table 2.

Table 2

| Compound No. | Mortality (%) | Compound No. | Mortality (%) | Compound No. | Mortality (%) |
|---|---|---|---|---|---|
| 2 | 100 | 66 | 100 | 283 | 100 |
| 6 | 100 | 68 | 100 | 284 | 100 |
| 8 | 100 | 69 | 100 | 285 | 100 |
| 9 | 100 | 71 | 80 | 291 | 100 |
| 10 | 100 | 72 | 100 | 302 | 100 |
| 14 | 100 | 75 | 100 | 303 | 100 |
| 16 | 100 | 80 | 100 | 316 | 100 |
| 18 | 100 | 82 | 100 | 318 | 100 |
| 23 | 100 | 83 | 100 | 319 | 100 |
| 25 | 100 | 87 | 100 | 325 | 100 |
| 27 | 100 | 88 | 100 | 326 | 100 |
| 29 | 100 | 144 | 100 | 327 | 100 |
| 31 | 100 | 145 | 100 | 328 | 100 |
| 32 | 100 | 251 | 100 | 333 | 100 |
| 33 | 100 | 152 | 100 | 352 | 100 |
| 35 | 100 | 196 | 90 | 353 | 100 |
| 37 | 100 | 197 | 90 | 355 | 100 |
| 42 | 100 | 198 | 100 | 395 | 90 |
| 48 | 100 | 220 | 100 | | |
| 51 | 100 | 221 | 100 | | |
| 53 | 80 | 224 | 100 | | |
| 56 | 80 | 225 | 100 | | |
| 59 | 100 | 244 | 100 | | |
| 63 | 100 | 245 | 100 | | |
| 65 | 100 | 282 | 100 | | |

TEST EXAMPLE 3

Activity to two-spotted spider mite (*Tetranychus urticae* Koch).

Testing method: Two-spotted spider mites were set free on the pot-planted soybean in a greenhouse. On the next day, a test composition of 1,000 ppm concentration was sprayed over the soybean by means of a spray gun. Two days or five days after the treatment, dead-and-survival was inspected to calculate the mortality.

The results obtained were as shown in Table 3.

Table 3*

| Compound No. | Mortality (%) | Compound No. | Mortality (%) | Compound No. | Mortality (%) |
|---|---|---|---|---|---|
| 2 | 100 | 59 | 100 | 218 | 100 |
| 6 | 100 | 63 | 80 | 219 | 70 |
| 8 | 100 | 65 | 100 | 221 | 100 |
| 9 | 80 | 66 | 100 | 222 | 80 |
| 10 | 100 | 68 | 100 | 223 | 70 |
| 14 | 100 | 69 | 100 | 224 | 100 |
| 16 | 100 | 71 | 100 | 225 | 100 |
| 18 | 80 | 72 | 100 | 233 | 100 |
| 23 | 100 | 75 | 80 | 237 | 100 |
| 25 | 100 | 80 | 80 | 241 | 70 |
| 27 | 80 | 82 | 100 | 242 | 70 |
| 29 | 100 | 83 | 100 | 244 | 70 |
| 31 | 100 | 87 | 100 | 245 | 100 |
| 32 | 100 | 88 | 100 | 247 | 70 |
| 33 | 100 | 188 | 90 | 248 | 100 |
| 35 | 100 | 194 | 100 | 249 | 70 |
| 37 | 100 | 196 | 100 | 255 | 100 |
| 42 | 100 | 197 | 80 | 258 | 100 |
| 48 | 100 | 198 | 100 | 259 | 100 |
| 51 | 100 | 213 | 100 | 260 | 100 |
| 53 | 100 | 216 | 70 | 270 | 70 |
| 56 | 100 | 217 | 100 | 274 | 100 |
| 280 | 80 | 317 | 100 | 379 | 100 |
| 282 | 80 | 318 | 100 | 380 | 100 |
| 283 | 70 | 319 | 100 | 381 | 70 |
| 284 | 100 | 320 | 70 | 382 | 100 |
| 285 | 100 | 321 | 70 | 383 | 100 |
| 289 | 100 | 327 | 100 | 384 | 100 |
| 291 | 100 | 328 | 100 | 385 | 100 |
| 293 | 100 | 336 | 100 | 387 | 100 |
| 294 | 100 | 337 | 100 | 388 | 100 |
| 295 | 100 | 350 | 100 | 390 | 80 |
| 297 | 100 | 353 | 100 | 394 | 80 |
| 298 | 100 | 354 | 100 | 395 | 80 |
| 299 | 100 | 355 | 100 | 398 | 80 |
| 300 | 90 | 359 | 100 | 399 | 80 |
| 301 | 100 | 364 | 60 | 400 | 70 |
| 302 | 70 | 367 | 100 | 401 | 70 |
| 303 | 80 | 368 | 100 | 402 | 100 |
| 304 | 100 | 370 | 100 | 404 | 100 |
| 305 | 70 | 371 | 100 | 406 | 60 |
| 307 | 70 | 372 | 100 | 407 | 100 |
| 308 | 100 | 373 | 100 | 408 | 100 |
| 312 | 100 | 374 | 100 | 409 | 100 |
| 314 | 100 | 376 | 100 | 411 | 100 |
| 315 | 100 | 377 | 100 | 412 | 100 |
| 316 | 100 | 378 | 100 | 415 | 100 |
| 416 | 100 | 421 | 70 | 426 | 100 |
| 418 | 70 | 422 | 100 | 427 | 100 |
| 419 | 100 | 425 | 100 | 428 | 100 |

*Compound No. 2–No. 88: Data of 2 days after treatment
Compound No. 188–No. 428: Data of 5 days after treatment

TEST EXAMPLE 4

Activity to cirrus red mite (*Panonychus citri* McGregor).

Testing method: The test was performed by Rothamstead method. A test composition was sprayed by means of a spray gun over grapefruit leaves infested with citrus red mites. After air-drying the grapefruit was left standing in a constant temperature cabinet at 25° C. Two days after the treatment, the number of survived mites was counted to calculate the mortality.

The results obtained were as shown in Table 4.

Table 4

| Compound No. | Mortality (%) | Compound No. | Mortality (%) | Compound No. | Mortality (%) |
|---|---|---|---|---|---|
| 2 | 50 | 66 | 50 | 309 | 100 |
| 6 | 80 | 68 | 50 | 310 | 100 |
| 8 | 80 | 69 | 80 | 316 | 100 |
| 9 | 50 | 71 | 50 | 319 | 100 |
| 10 | 80 | 72 | 80 | 368 | 100 |
| 14 | 50 | 75 | 50 | | |
| 16 | 100 | 80 | 100 | | |
| 18 | 100 | 82 | 100 | | |
| 23 | 80 | 83 | 50 | | |
| 25 | 80 | 87 | 100 | | |
| 27 | 100 | 88 | 100 | | |
| 29 | 100 | 115 | 100 | | |
| 31 | 100 | 118 | 100 | | |
| 32 | 100 | 123 | 100 | | |
| 33 | 100 | 124 | 100 | | |
| 35 | 100 | 131 | 100 | | |
| 37 | 100 | 135 | 100 | | |
| 42 | 100 | 145 | 100 | | |
| 48 | 100 | 148 | 100 | | |

Table 4-continued

| Compound No. | Mortality (%) | Compound No. | Mortality (%) | Compound No. | Mortality (%) |
|---|---|---|---|---|---|
| 51 | 50 | 153 | 100 | | |
| 53 | 100 | 161 | 100 | | |
| 56 | 100 | 218 | 100 | | |
| 59 | 100 | 219 | 100 | | |
| 63 | 50 | 249 | 100 | | |
| 65 | 100 | 281 | 100 | | |

TEST EXAMPLE 5

Activity against larvae of green rice leafhopper (*Nephotettix cincticeps* Uhler).

Testing method: Five rice seedlings of the 1.5 leaf age were dipped in a test composition of 400 ppm concentration for 30 seconds. After air-drying, the seedlings were placed in a glass tube containing 1 ml of water and infested with five second-instar larvae of green rice leafhopper. The glass tube was left standing in a constant temperature cabinet at 25° C. Seven days after the treatment, dead-and-survival was inspected to calculate the mortality (3-replication test).

The results obtained were as shown in Table 5.

Table 5

| Compound No. | Mortality (%) | Compound No. | Mortality (%) | Compound No. | Mortality (%) |
|---|---|---|---|---|---|
| 2 | 50 | 66 | 80 | 194 | 100 |
| 6 | 80 | 68 | 50 | 198 | 100 |
| 8 | 80 | 69 | 100 | 220 | 100 |
| 9 | 100 | 71 | 50 | 221 | 100 |
| 10 | 100 | 72 | 80 | 224 | 100 |
| 14 | 100 | 75 | 50 | 225 | 90 |
| 16 | 100 | 80 | 50 | 244 | 100 |
| 18 | 100 | 82 | 80 | 245 | 100 |
| 23 | 80 | 83 | 80 | 248 | 100 |
| 25 | 100 | 87 | 80 | 249 | 100 |
| 27 | 80 | 88 | 80 | 282 | 100 |
| 29 | 80 | 130 | 100 | 283 | 90 |
| 31 | 50 | 131 | 100 | 284 | 100 |
| 32 | 50 | 140 | 100 | 285 | 100 |
| 33 | 100 | 141 | 100 | 291 | 100 |
| 35 | 50 | 142 | 100 | 302 | 100 |
| 37 | 50 | 143 | 100 | 303 | 100 |
| 42 | 80 | 144 | 100 | 318 | 100 |
| 48 | 80 | 145 | 100 | 319 | 100 |
| 51 | 50 | 150 | 90 | 325 | 100 |
| 53 | 50 | 151 | 100 | 326 | 100 |
| 56 | 50 | 152 | 100 | 327 | 100 |
| 59 | 100 | 153 | 100 | 328 | 100 |
| 63 | 80 | 156 | 100 | 333 | 100 |
| 65 | 50 | 188 | 100 | 352 | 100 |
| | | | | 353 | 100 |
| 355 | 100 | | | | |
| 395 | 100 | | | | |

TEST EXAMPLE 6

Insecticidal activity to larvae of house mosquito (*Culex pipiens pallens* Coquillett).

Test method: In a 200-ml beaker, was placed together with a feed 100 ml of a test composition diluted with deionized water to 10 ppm concentration. The test composition was infested with 20 first-instar larvae of house mosquito and the beaker was covered with a sheet of Japanese paper. The beaker was kept in a constant temperature cabinet at 25° C. Five days after the treatment, the dead-and-survival was inspected to calculate the mortality.

The results obtained were as shown in Table 6.

Table 6

| Compound No. | Mortality (%) | Compound No. | Mortality (%) | Compound No. | Mortality (%) |
|---|---|---|---|---|---|
| 125 | 80 | 157 | 100 | 282 | 90 |
| 126 | 100 | 162 | 100 | 283 | 70 |
| 127 | 100 | 188 | 100 | 284 | 100 |
| 129 | 100 | 194 | 80 | 285 | 100 |
| 131 | 100 | 197 | 100 | 291 | 70 |
| 134 | 80 | 198 | 100 | 301 | 90 |
| 135 | 100 | 213 | 100 | 302 | 100 |
| 136 | 100 | 218 | 100 | 307 | 100 |
| 137 | 100 | 220 | 80 | 308 | 100 |
| 139 | 100 | 221 | 100 | 310 | 100 |
| 140 | 100 | 223 | 100 | 312 | 100 |
| 141 | 100 | 224 | 100 | 314 | 100 |
| 142 | 100 | 225 | 100 | 315 | 100 |
| 143 | 80 | 244 | 100 | 316 | 70 |
| 144 | 100 | 245 | 100 | 317 | 100 |
| 145 | 100 | 247 | 100 | 318 | 90 |
| 146 | 100 | 248 | 90 | 319 | 100 |
| 147 | 100 | 249 | 100 | 320 | 70 |
| 149 | 100 | 259 | 100 | 321 | 70 |
| 150 | 100 | 265 | 100 | 325 | 100 |
| 151 | 100 | 269 | 100 | 326 | 100 |
| 152 | 100 | 270 | 100 | 327 | 90 |
| 155 | 100 | 274 | 100 | 328 | 100 |
| 156 | 100 | 280 | 90 | 333 | 100 |

| Compound No. | Mortality (%) |
|---|---|
| 352 | 100 |
| 353 | 100 |
| 355 | 90 |
| 395 | 100 |

TEST EXAMPLE 7

Insecticidal activity to adult rust-red-flour beetle (*Tribolium castaneum* Herbst).

Testing method: Into a 9-cm Petri dish covered on the bottom with a piece of filter paper, was introduced 7 ml of a test composition of 400 ppm concentration. Ten adult rust-red flour beetles were released in the Petri dish and left standing in a constant temperature cabinet at 25° C. After 24 hours, the dead-and-survival was inspected to calculate the mortality.

The results obtained were as shown in Table 7.

Table 7

| Compound No. | Mortality (%) |
|---|---|
| 213 | 100 |
| 216 | 100 |
| 217 | 100 |
| 218 | 100 |
| 219 | 100 |
| 222 | 100 |
| 223 | 100 |
| 224 | 100 |

TEST EXAMPLE 8

Insecticidal activity against larvae of 28-spotted lady beetle (*Epilachna vigintioctopunctana* Fabricius).

Testing method: Leaflets of tomato grown in a greenhouse were dipped in a test composition of 100 ppm concentration for 30 seconds and after that the leaflets were dried by air. In a Petri dish covered on the bottom with a piece of filter paper, were introduced 1 ml of water and three treated tomato leaflets. After having been infested with seven second-instar larvae of 28-spotted lady beetle, the Petri dish was left standing in a constant temperature cabinet at 25° C. Five days after the treatment, the dead-and-survival was inspected to calculate the mortality (2-replication test).

The results obtained were as shown in Table 8.

Table 8

| Compound No. | Mortality (%) | Compound No. | Mortality (%) | Compound No. | Mortality (%) |
|---|---|---|---|---|---|
| 126 | 80 | 155 | 100 | 325 | 100 |
| 127 | 80 | 156 | 90 | 326 | 100 |
| 131 | 100 | 157 | 100 | 327 | 100 |
| 134 | 80 | 162 | 50 | 328 | 100 |
| 135 | 100 | 163 | 60 | 352 | 100 |
| 136 | 50 | 198 | 100 | 353 | 100 |
| 137 | 50 | 220 | 100 | 355 | 100 |
| 139 | 100 | 221 | 90 | 364 | 80 |
| 140 | 50 | 244 | 90 | 398 | 80 |
| 141 | 100 | 245 | 90 | 399 | 100 |
| 142 | 100 | 249 | 100 | 404 | 90 |
| 143 | 100 | 283 | 90 | 405 | 90 |
| 144 | 100 | 284 | 100 | 411 | 100 |
| 145 | 100 | 285 | 80 | 412 | 100 |
| 146 | 100 | 291 | 100 | 418 | 70 |
| 147 | 100 | 302 | 80 | 422 | 90 |
| 148 | 100 | 303 | 100 | | |
| 149 | 100 | 314 | 100 | | |
| 150 | 80 | 316 | 100 | | |
| 151 | 100 | 318 | 100 | | |
| 152 | 100 | 319 | 100 | | |

TEST EXAMPLE 9

Insecticidal activity against larvae of bug. (*Togo hemipterus* Scott).

Test method: Into a glass tube (1.6 cm in internal diameter and 9 cm in length), was added 1 ml of a test composition in 10 ppm concentration just to moisten the absorbent cotton. Five rice seeds and five first-instar larvae were introduced into the glass tube and the tube end was covered with a piece of Japanese paper. The glass tube was kept in a constant temperature cabinet at 25° C. Five days after treatment, the dead-and-survival was inspected to calculate the mortality (3-replication test).

The results obtained were as shown in Table 9.

Table 9

| Compound No. | Mortality (%) | Compound No. | Mortality (%) | Compound No. | Mortality (%) |
|---|---|---|---|---|---|
| 118 | 100 | 139 | 100 | 151 | 80 |
| 126 | 100 | 140 | 50 | 152 | 100 |
| 127 | 100 | 141 | 80 | 155 | 100 |
| 129 | 100 | 142 | 100 | 156 | 50 |
| 131 | 100 | 143 | 100 | 157 | 100 |
| 134 | 80 | 144 | 100 | 162 | 50 |
| 135 | 100 | 145 | 100 | 216 | 100 |
| 136 | 100 | 149 | 50 | 217 | 100 |
| 137 | 50 | 150 | 50 | 222 | 100 |

TEST EXAMPLE 10

Insecticidal activity against larvae of diamond-back moth (*Plutilla xylostella* Linn'e). Testing method: A test composition of 400 ppm concentration was sprayed over the pot-planted chinese cabbage in a greenhouse by means of a spray gun. After air-drying, the chinese cabbage was infested with 10 first-instar larvae of diamond-back moth and was left standing in the greenhouse. Three days after the treatment, the dead-and-survival was inspected to calculate the mortality (3-replication test).

The results obtained were as shown in Table 10.

Table 10

| Compound No. | Mortality (%) | Compound No. | Mortality (%) | Compound No. | Mortality (%) |
|---|---|---|---|---|---|
| 207 | 100 | 232 | 70 | 329 | 100 |
| 208 | 80 | 236 | 100 | 331 | 100 |
| 219 | 80 | 324 | 100 | 333 | 100 |
| 228 | 100 | 326 | 100 | 366 | 100 |
| 230 | 100 | 327 | 100 | | |

What is claimed is:

1. A tetrahydro-1,3,5-thiadiazin-4-one represented by the formula,

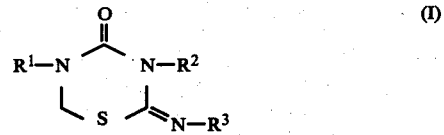

(wherein $R^1$, $R^2$ and $R^3$, which may be the same or different, represent each an alkyl group of $C_1$ to $C_8$, allyl group, cycloalkyl group of $C_3$ to $C_6$, alkoxyalkyl group having a total of 3 to 6 carbon atoms, benzyl group, phenyl group or substituted phenyl group having as substituents one or two members selected from the group consisting of alkyl groups of $C_1$ to $C_4$, nitro group, halogen atoms, alkoxy groups of $C_1$ to $C_4$ and trifluoromethyl group and $R^2$ and $R^3$ may also represent hydrogen atoms) or an acid addition salt thereof.

2. A tetrahydro-1,3,5-thiadiazin-4-one or an acid addition salt thereof according to claim 1, wherein $R^2$ and $R^3$, which may be the same or different, are alkyl groups of $C_1$ to $C_8$.

3. A tetrahydro-1,3,5-thiadiazin-4-one or an acid addition salt thereof according to claim 1 or 2, wherein $R^1$ is phenyl group.

4. A tetrahydro-1,3,5-thiadiazin-4-one or an acid addition salt thereof according to claim 1 or 2, wherein $R^1$ is a substituted phenyl group having as substituents one or two members selected from the group consisting of alkyl groups of $C_1$ to $C_4$, nitro group, halogen atoms, and alkoxy groups of $C_1$ to $C_4$.

5. 2-t-Butylimino-3-isopropyl-5-phenyl-tetrahydro-1,3,5-thiadiazin-4-one or an acid addition salt thereof.

6. 2-t-Butylimino-3-isopropyl-5-(4-tolyl)-tetrahydro-1,3,5-thiadiazin-4-one or an acid addition salt thereof.

7. 2-t-Butylimino-3-isopropyl-5-(3-chlorophenyl)-tetrahydro-1,3,5-thiadiazin-4-one or an acid addition salt thereof.

8. 2-t-Butylimino-3-isopropyl-5-(3-tolyl)-tetrahydro-1,3,5-thiadiazin-4-one or an acid addition salt thereof.

9. 2-t-Butylimino-3-sec-butyl-5-(2,4-dimethylphenyl)-tetrahydro-1,3,5-thiadiazin-4-one or an acid addition salt thereof.

10. 2-t-Butylimino-3-isopropyl-5-(2-chlorophenyl)-tetrahydro-1,3,5-thiadiazin-4-one or an acid addition salt thereof.

11. 2-t-Butylimino-3-isopropyl-5-(4-methoxyphenyl)-tetrahydro-1,3,5-thiadiazin-4-one or an acid addition salt thereof.

12. 2-t-Butylimino-3-sec-butyl-5-(4-methoxyphenyl)-tetrahydro-1,3,5-thiadiazin-4-one or an acid addition salt thereof.

13. An acid addition salt of a tetrahydro-1,3,5-thiadiazin-4-one according to claim 1, wherein the acid is an inorganic acid.

14. An insecticidal and miticidal composition comprising a tetrahydro-1,3,5-thiadiazin-4-one represented by the formula,

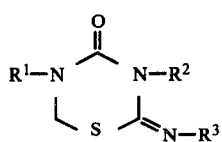

(wherein $R^1$, $R^2$ and $R^3$, which may be the same or different, represent each an alkyl group of $C_1$ to $C_8$, allyl group, cycloalkyl group of $C_3$ to $C_6$, alkoxyalkyl group having a total of 3 to 6 carbon atoms, benzyl group, phenyl group or substituted phenyl group having as substituents one or two members selected from the group consisting of alkyl groups of $C_1$ to $C_4$, nitro group, halogen atoms, alkoxy groups of $C_1$ to $C_4$, and trifluoromethyl group and $R^2$ and $R^3$ may also represent hydrogen atoms) or an acid addition salt thereof and an inert diluent.

15. A composition according to claim 14 for use in controlling insects and mites injurious to agricultural crops.

16. A composition according to any of claims 14 and 15 for use in controlling planthoppers and leafhoppers.

17. A composition according to claim 14 wherein $R^2$ and $R^3$ in the formula (I), which may be the same or different, represent each an alkyl group of $C_1$ to $C_8$.

18. A composition according to claim 17, wherein $R^1$ in the formula (I) represents phenyl group.

19. A composition according to claim 17, wherein $R^1$ in the formula (I) represents a substituted phenyl group having as substituents one or two members selected from the group consisting of alkyl groups of $C_1$ to $C_4$, nitro group, halogen atoms, and alkoxy groups of $C_1$ to $C_4$.

20. A composition according to claim 14, wherein the composition contains 2-t-butylimino-3-isopropyl-5-phenyltetrahydro-1,3,5-thiadiazin-4-one or an acid addition salt thereof.

21. A composition according to claim 14, wherein the composition contains 2-t-butylimino-3-isopropyl-5-(p-tolyl)-tetrahydro-1,3,5-thiadiazin-4-one or an acid addition salt thereof.

22. A composition according to claim 14 wherein $R^1$ in the formula (I) represents the phenyl group.

23. A composition according to claim 14 wherein $R^1$ in the formula (I) represents a substituted phenyl group having as substituents one or two members selected from the group consisting of alkyl groups of $C_1$ to $C_4$, nitro group, halogen atoms, and alkoxy groups of $C_1$ to $C_4$.

24. A method for protecting agricultural crops from injurious insects and mites, which comprises applying to the agricultural crops or the soil where the agricultural crops are grown an effective amount of a tetrahydro-1,3,5-thiadiazin-4-one represented by the formula,

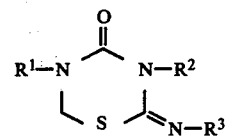

(wherein $R^1$, $R^2$ and $R^3$, which may be the same or different, represent each an alkyl group of $C_1$ to $C_8$, allyl group, cycloalkyl group of $C_3$ to $C_6$, alkoxyalkyl group having a total of 3 to 6 carbon atoms, benzyl group, phenyl group or substituted phenyl group having as substituents one or two members selected from the group consisting of alkyl groups of $C_1$ to $C_4$, nitro group, halogen atoms, alkoxy groups of $C_1$ to $C_4$ and trifluoromethyl group, and $R^2$ and $R^3$ may also represent hydrogen atoms) or an acid addition salt thereof.

* * * * *